(12) United States Patent
Tsai et al.

(10) Patent No.: US 9,005,772 B2
(45) Date of Patent: Apr. 14, 2015

(54) THIOAZOLE AND OXAZOLE CARBENE METAL COMPLEXES AS PHOSPHORESCENT OLED MATERIALS

(75) Inventors: Jui-Yi Tsai, Newtown, PA (US); Zeinab Elshenawy, Holland, PA (US)

(73) Assignee: Universal Display Corporation, Ewing, NJ (US)

( * ) Notice: Subject to any disclaimer, the term of this patent is extended or adjusted under 35 U.S.C. 154(b) by 467 days.

(21) Appl. No.: 13/033,287

(22) Filed: Feb. 23, 2011

(65) Prior Publication Data

US 2012/0212126 A1 Aug. 23, 2012

(51) Int. Cl.
| | |
|---|---|
| *H01L 51/54* | (2006.01) |
| *C09K 11/06* | (2006.01) |
| *H01L 51/00* | (2006.01) |
| *C07F 15/00* | (2006.01) |
| *C07F 9/50* | (2006.01) |
| *C07F 13/00* | (2006.01) |
| *C07F 1/00* | (2006.01) |
| *C07F 1/12* | (2006.01) |
| *C07F 3/00* | (2006.01) |
| *C07F 5/02* | (2006.01) |
| *C07F 5/06* | (2006.01) |
| *C07F 7/08* | (2006.01) |
| *H01L 51/50* | (2006.01) |

(52) U.S. Cl.
CPC ........ *H01L 51/0088* (2013.01); *C07F 15/0086* (2013.01); *H01L 51/0085* (2013.01); *C07F 9/5022* (2013.01); *C07F 13/00* (2013.01); *C07F 15/0093* (2013.01); *C07F 1/005* (2013.01); *C07F 1/12* (2013.01); *C07F 3/003* (2013.01); *C07F 5/02* (2013.01); *C07F 5/069* (2013.01); *C07F 7/0809* (2013.01); *C07F 7/0812* (2013.01); *C07F 9/5045* (2013.01); *H01L 51/5016* (2013.01); *Y10S 428/917* (2013.01)

(58) Field of Classification Search
None
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Baldo et al., "Highly Efficient Phosphorescent Emission from Organic Electroluminescent Devices," Nature, vol. 395, 151-154, (1998).

(Continued)

*Primary Examiner* — Marie R. Yamnitzky
(74) *Attorney, Agent, or Firm* — Duane Morris LLP

(57) ABSTRACT

Compounds are provided that comprise a heterocyclic carbene ligand. In particular, an oxazole or a thioazole carbene are used in place of the traditional imidazole carbene. These compounds may be used in OLEDs to provide devices having improved properties, such as stability and color-tuning. Additionally, a novel methodology to synthesize heterocyclic carbene metal complexes is provided.

25 Claims, 3 Drawing Sheets

(56) References Cited

U.S. PATENT DOCUMENTS

| | | |
|---|---|---|
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0258433 A1 | 11/2005 | Djurovich et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0200686 A1* | 8/2008 | Molt et al. ............... 548/103 |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0092854 A1* | 4/2009 | Walters et al. ............ 428/691 |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2012/0305894 A1* | 12/2012 | Kim et al. ............... 257/40 |
| 2012/0319050 A1* | 12/2012 | Metz et al. ............ 252/301.16 |
| 2013/0032766 A1* | 2/2013 | Molt et al. ............ 252/519.2 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | WO 01/39234 | 5/2001 |
| WO | WO 02/02714 | 1/2002 |
| WO | WO 0215645 | 2/2002 |
| WO | WO 03/040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005/113704 | 12/2005 |
| WO | WO 2005123873 | 12/2005 |
| WO | WO 2006009024 | 1/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2008132085 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008056746 | 5/2008 |
| WO | WO 2008101842 | 8/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009021126 | 2/2009 |
| WO | WO 2009050290 | 4/2009 |
| WO | WO 2009062578 | 5/2009 |
| WO | WO 2009063833 | 5/2009 |
| WO | WO 2009066678 | 5/2009 |
| WO | WO 2009066779 | 5/2009 |
| WO | WO 2009086028 | 7/2009 |
| WO | WO 2009100991 | 8/2009 |

OTHER PUBLICATIONS

Baldo et al., "Very high-efficiency green organic light-emitting devices based on electrophosphorescence," Appl. Phys. Lett., vol. 75, No. 4-6 (1999).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Tung, Yung-Liang et al., "Organic Light-Emitting Diodes Based on Charge-Neutral $Ru^{II}$ PHosphorescent Emitters," Adv. Mater., 17(8):1059-1064 (2005).

Huang, Jinsong et al., "Highly Efficient Red-Emission Polymer Phosphorescent LightEmitting Diodes Based on Two Novel Tris(1-phenylisoquinolinato-C2,N)iridium(III) Derivatives," Adv. Mater., 19:739-743 (2007).

Wong, Wai-Yeung, "Multifunctional Iridium Complexes Based on Carbazole Modules as Highly Efficient Electrophosphors," Angew. Chem. Int. Ed., 45:7800-7803 (2006).

(56) References Cited

OTHER PUBLICATIONS

Tang, C.W. and VanSlyke, S.A., "Organic Electroluminescent Diodes," *Appl. Phys. Lett.*, 51(12):913-915 (1987).
Adachi, Chihaya et al., "Organic Electroluminescent Device Having a Hole Conductor as an Emitting Layer," *Appl. Phys. Lett.*, 55(15):1489-1491 (1989).
Ma, Yuguang et al., "Triplet Luminescent Dinuclear-Gold(*I*) Complex-Based Light-Emitting Diodes with Low Turn-On voltage," *Appl. Phys. Lett.*, 74(10):1361-1363 (1999).
Gao, Zhiqiang et al., "Bright-Blue Electroluminescence From a Silyl-Substituted ter-(phenylene-vinylene) derivative," *Appl. Phys. Lett.*, 74(6):865-867 (1999).
Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).
Hung, L.S. et al., "Anode Modification in Organic Light-Emitting Diodes by Low-Frequency Plasma Polymerization of $CHF_3$," *Appl. Phys. Lett.*, 78(5):673-675 (2001).
Ikai, Masamichi et al., "Highly Efficient Phosphorescence From Organic Light-Emitting Devices with an Exciton-Block Layer," *Appl. Phys. Lett.*, 79(2):156-158 (2001).
Wang, Y. et al., "Highly Efficient Electroluminescent Materials Based on Fluorinated Organometallic Iridium Compounds," *Appl. Phys. Lett.*, 79(4):449-451 (2001).
Kwong, Raymond C. et al., "High Operational Stability of Electrophosphorescent Devices," *Appl. Phys. Lett.*, 81(1):162-164 (2002).
Holmes, R.J. et al., "Blue Organic Electrophosphorescence Using Exothermic Host-Guest Energy Transfer," *Appl. Phys. Lett.*, 82(15):2422-2424 (2003).
Sotoyama, Wataru et al., "Efficient Organic Light-Emitting Diodes with Phosphorescent Platinum Complexes Containing $N^{\wedge}C^{\wedge}$-Coordinating Tridentate Ligand," *Appl. Phys. Lett.*, 86:153505-1-153505-3 (2005).
Okumoto, Kenji et al., "Green Fluorescent Organic Light-Emitting Device with External Quantum Efficiency of Nearly 10%," *Appl. Phys. Lett.*, 89:063504-1-063504-3 (2006).
Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).
Aonuma, Masaki et al., "Material Design of Hole Transport Materials Capable of Thick-Film Formation in Organic Light Emitting Diodes," *Appl. Phys. Lett.*, 90:183503-1-183503-3 (2007).
Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).
Adachi, Chihaya et al., "High-Efficiency Red Electrophosphorescence Devices," *Appl. Phys. Lett.*, 78(11):1622-1624 (2001).
Wong, Keith Man-Chung et al., "A Novel Class of Phosphorescent Gold(III) Alkynyl-Based Organic Light-Emitting Devices with Tunable Colour," *Chem. Commun.*, 2906-2908 (2005).
Hamada, Yuji et al., "High Luminance in Organic Electroluminescent Devices with Bis(10-hydroxybenzo[h]quinolinato)beryllium as an Emitter," *Chem. Lett.*, 905-906 (1993).
Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).
Mi, Bao-Xiu et al., "Thermally Stable Hole-Transporting Material for Organic Light-Emitting Diode: an Isoindole Derivative," *Chem. Mater.*, 15(16):3148-3151 (2003).
Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).
Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).
Takizawa, Shin-ya et al., "Phosphorescent Iridium Complexes Based on 2-Phenylimidazo[1,2- α]pyridine Ligands: Tuning of Emission Color toward the Blue Region and Application to Polymer Light-Emitting Devices," *Inorg. Chem.*, 46(10):4308-4319 (2007).
Lamansky, Sergey et al., "Synthesis and Characterization of Phosphorescent Cyclometalated Iridium Complexes," *Inorg. Chem.*, 40(7):1704-1711 (2001).
Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).
Noda, Tetsuya and Shirota, Yasuhiko, "5,5'-Bis(dimesitylboryl)-2,2'-bithiophene and 5,5''-Bis(dimesitylboryl)-2,2':5',2''-terthiophene as a Novel Family of Electron-Transporting Amorphous Molecular Materials," *J. Am. Chem. Soc.*, 120 (37):9714-9715 (1998).
Sakamoto, Youichi et al., "Synthesis, Characterization, and Electron-Transport Property of Perfluorinated Phenylene Dendrimers," *J. Am. Chem. Soc.*, 122(8):1832-1833 (2000).
Adachi, Chihaya et al., "Nearly 100% Internal Phosphorescence Efficiency in an Organic Light Emitting Device," *J. Appl. Phys.*, 90(10):5048-5051 (2001).
Shirota, Yasuhiko et al., "Starburst Molecules Based on π-Electron Systems as Materials for Organic Electroluminescent Devices," *Journal of Luminescence*, 72-74:985-991 (1997).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).
Kido, Junji et al., "1,2,4-Triazole Derivative as an Electron Transport Layer in Organic Electroluminescent Devices," *Jpn. J. Appl. Phys.*, 32:L917-L920 (1993).
Van Slyke, S. A. et al., "Organic Electroluminescent Devices with Improved Stability," *Appl. Phys. Lett.*, 69(15):2160-2162 (1996).
Guo, Tzung-Fang et al., "Highly Efficient Electrophosphorescent Polymer Light-Emitting Devices," *Organic Electronics*, 1:15-20 (2000).
Palilis, Leonidas C., "High Efficiency Molecular Organic Light-Emitting Diodes Based on Silole Derivatives and Their Exciplexes," *Organic Electronics*, 4:113-121 (2003).
Ikeda, Hisao et al., "P-185: Low-Drive-Voltage OLEDs with a Buffer Layer Having Molybdenum Oxide," *SID Symposium Digest*, 37:923-926 (2006).
T. Östergard et al., "Langmuir-Blodgett Light-Emitting Diodes of Poly(3-Hexylthiophene): Electro-Optical Characteristics Related to Structure," *Synthetic Metals*, 87:171-177 (1997).
Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).
Salbeck, J. et al., "Low Molecular Organic Glasses for Blue Electroluminescence," *Synthetic Metals*, 91:209-215 (1997).
Han et al., "Must an N-Heterocyclic Carbene Be a Terminal Ligand?" *Organometallics* 2010, 29, 2403-2405.
Chien et al., "Stepwise and one-pot syntheses of Ir(III) complexes with imidazolium-based carbene ligands" *Dalton Trans.*, 2008, 916-923.
Stéphane Bellemin-Laponnaz, "Synthesis of N,O-heterocyclic carbene and coordination to rhodium(I) and copper(I)" *Polyhedron* 29 (2010) 30-33.
Galmari Venkatachalam et al: "Synthesis, structural diversity, and ligand-transfer potential of (carbene)copper(I) complexes", Helvetica Chimica Acta, Verlag Helvetica Chimica Acta, Basel, CH, vol. 92, No. 6, Jun. 1, 2009, pp. 1034-1045.
Jered C Garrison et al: "Ag(I) N-heterocyclic carbene complexes: synthesis, structure, and application", Chemical Reviews, American Chemical Society, US, vol. 105, No. 11, Nov. 9, 2005, pp. 3978-4008.
Silvia Diez-Gonzalez et al: "[(NHC)CuX] complexes: synthesis, characterization and catalytic activities in reduction reactions and Click chemistry. On the advantage of using well-defined catalytic systems", Dalton Transactions, Royal Society of Chemistry, United Kingdom, vol . 39, No. 32, Jan. 11, 2010, pp. 7595-7606.
International Search Report in PCT/US2012/026411 application, dated Jun. 1, 2012.

* cited by examiner

THIOAZOLE AND OXAZOLE CARBENE METAL COMPLEXES AS PHOSPHORESCENT OLED MATERIALS

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the present invention is related to heterocyclic carbene metal complexes. These materials may be used in OLEDs to provide improved stability and color-tuning.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure:

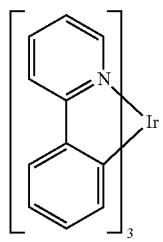

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Heterocyclic carbene metal complexes are provided. The compounds comprise a ligand L having the structure:

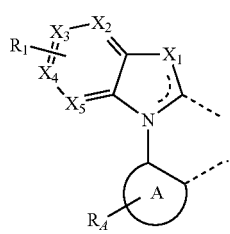

Formula I $X_1$ is S or O. $X_2$, $X_3$, $X_4$, and $X_5$ are independently C or N. At least one of $X_2$, $X_3$, $X_4$, and $X_5$ is N. $R_1$ may represent mono, di, tri or tetra substitutions. $R_1$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_1$ are optionally joined to form a fused ring. $R_A$ may represent mono, di, tri, or tetra substitutions. $R_A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_A$ are optionally joined to form a fused ring. A is a 5-membered or 6-membered carbocyclic or heterocyclic ring. Preferably, A is benzene. The ligand L is coordinated to a transition metal M having an atomic number greater than 40. Preferably, the metal M is Ir or Os. More preferably, the metal M is Ir. Additionally, the metal M is preferably Os. The bidentate ligand L may be linked with other ligands to comprise a tridentate, tetradentate, pentadentate or hexadentate ligand.

In one aspect, the ligand has the formula:

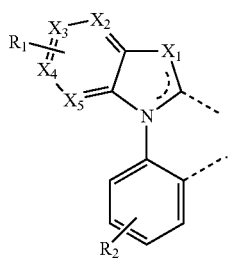

Formula II

At least one of $X_2$, $X_3$, $X_4$, and $X_5$ is N. $R_2$ may represent mono, di, tri or tetra substitutions. $R_2$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_2$ are optionally joined to form a fused ring.

In another aspect, the ligand has the formula:

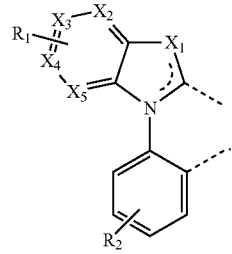

Formula II

At least two of $X_2$, $X_3$, $X_4$, and $X_5$ is N. $R_2$ may represent mono, di, tri or tetra substitutions. $R_2$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_2$ are optionally joined to form a fused ring.

In one aspect, the compound is heteroleptic. In another aspect, the compound is homoleptic. In yet another aspect, the compound has the formula:

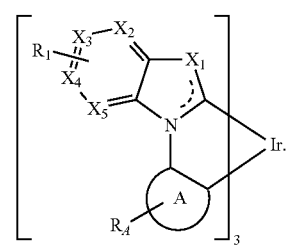

Formula III

Specific examples of the heterocyclic carbene compounds are provided. In one aspect, the compound is selected from the group consisting of:

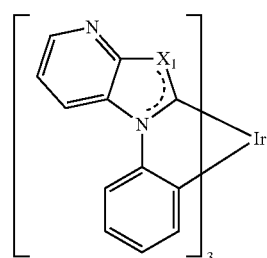

Compound 1G

Compound 2G
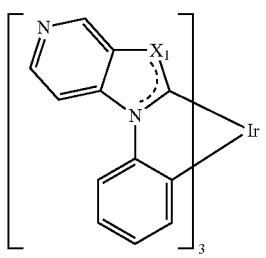
Compound 3G
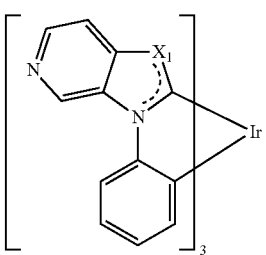
Compound 4G
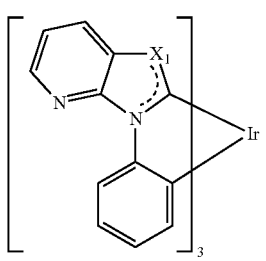
Compound 5G
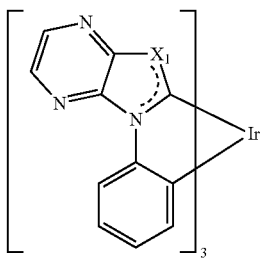
Compound 6G
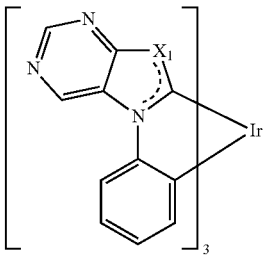
Compound 7G
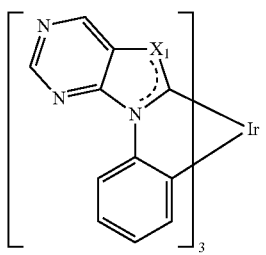
Compound 8G
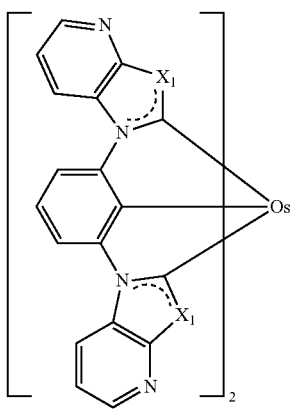
Compound 9G
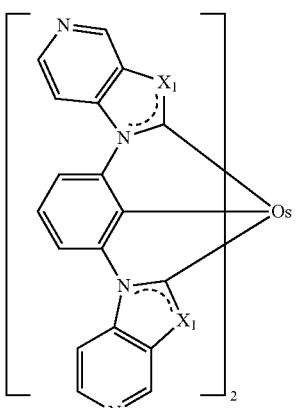
Compound 10G
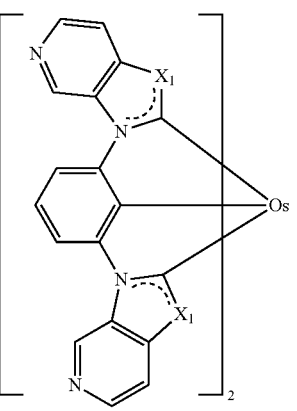
Compound 11G
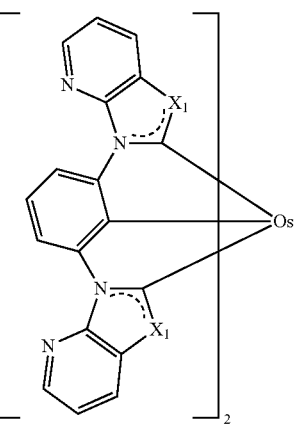

Compound 12G
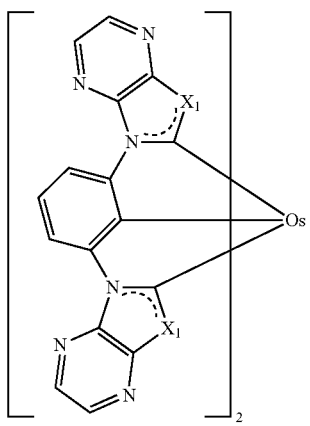
Compound 13G
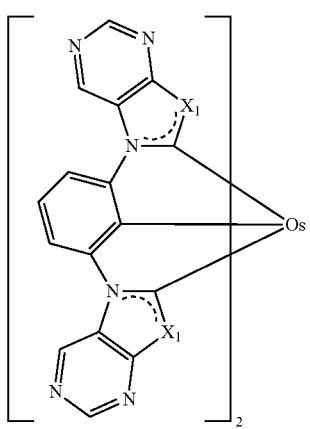
Compound 14G
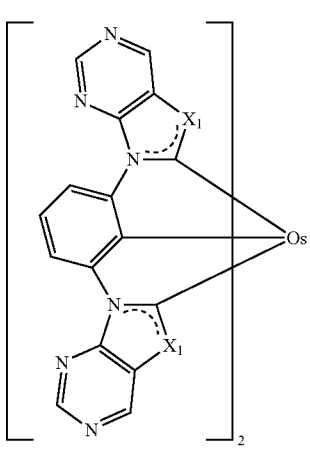
Compound 15G
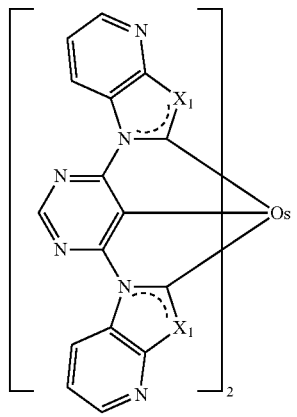
Compound 16G
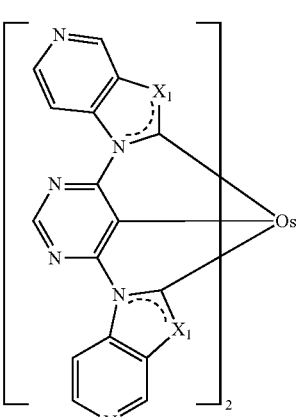
Compound 17G
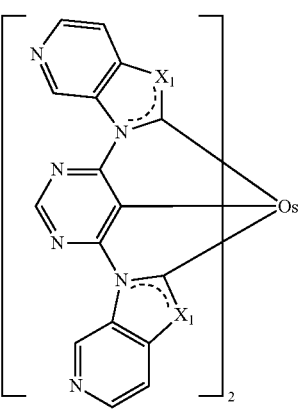
Compound 18G Compound 19G
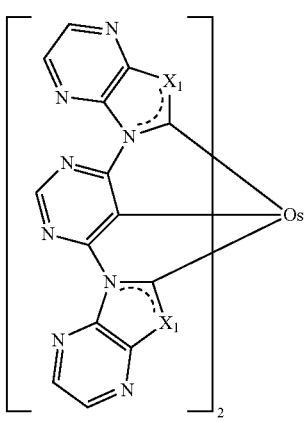
Compound 20G
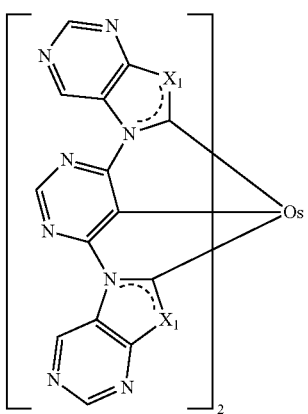
Compound 21G
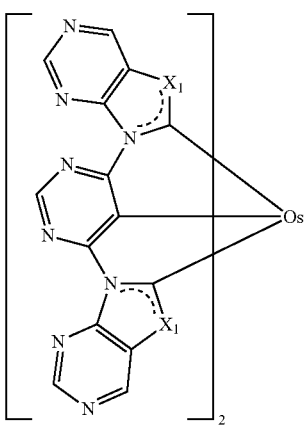
Compound 22G
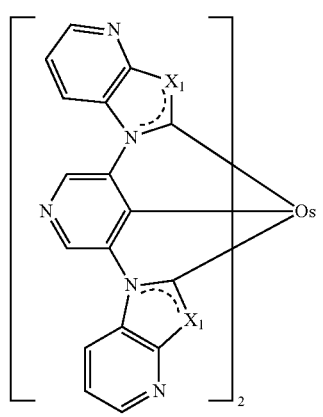
Compound 23G
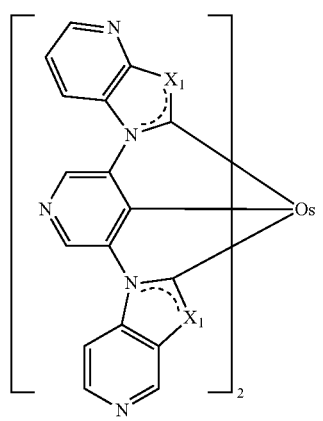
Compound 24G
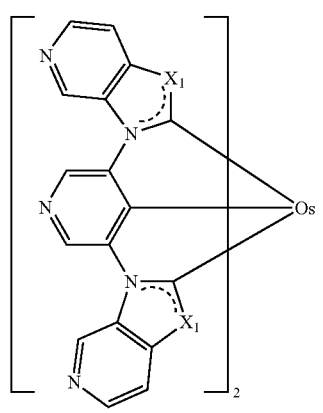
Compound 25G
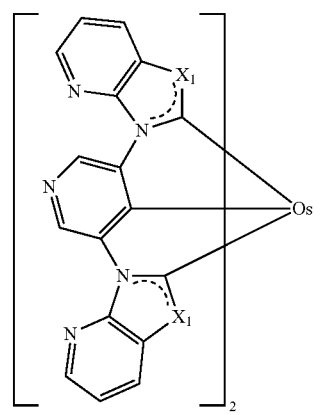

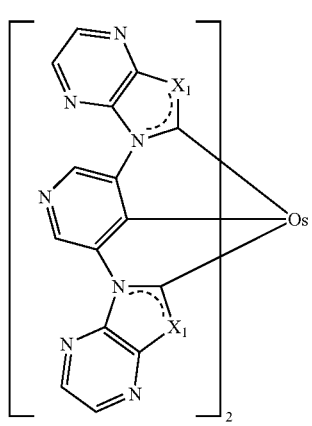
Compound 26G
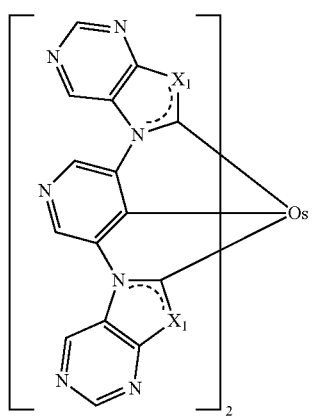
Compound 27G
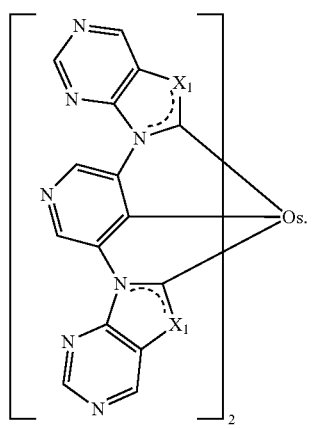
Compound 28G
Each $X_1$ is independently S or O.
Additional specific examples of heterocyclic carbene compounds are provided. In one aspect, the compound is selected from the group consisting of:
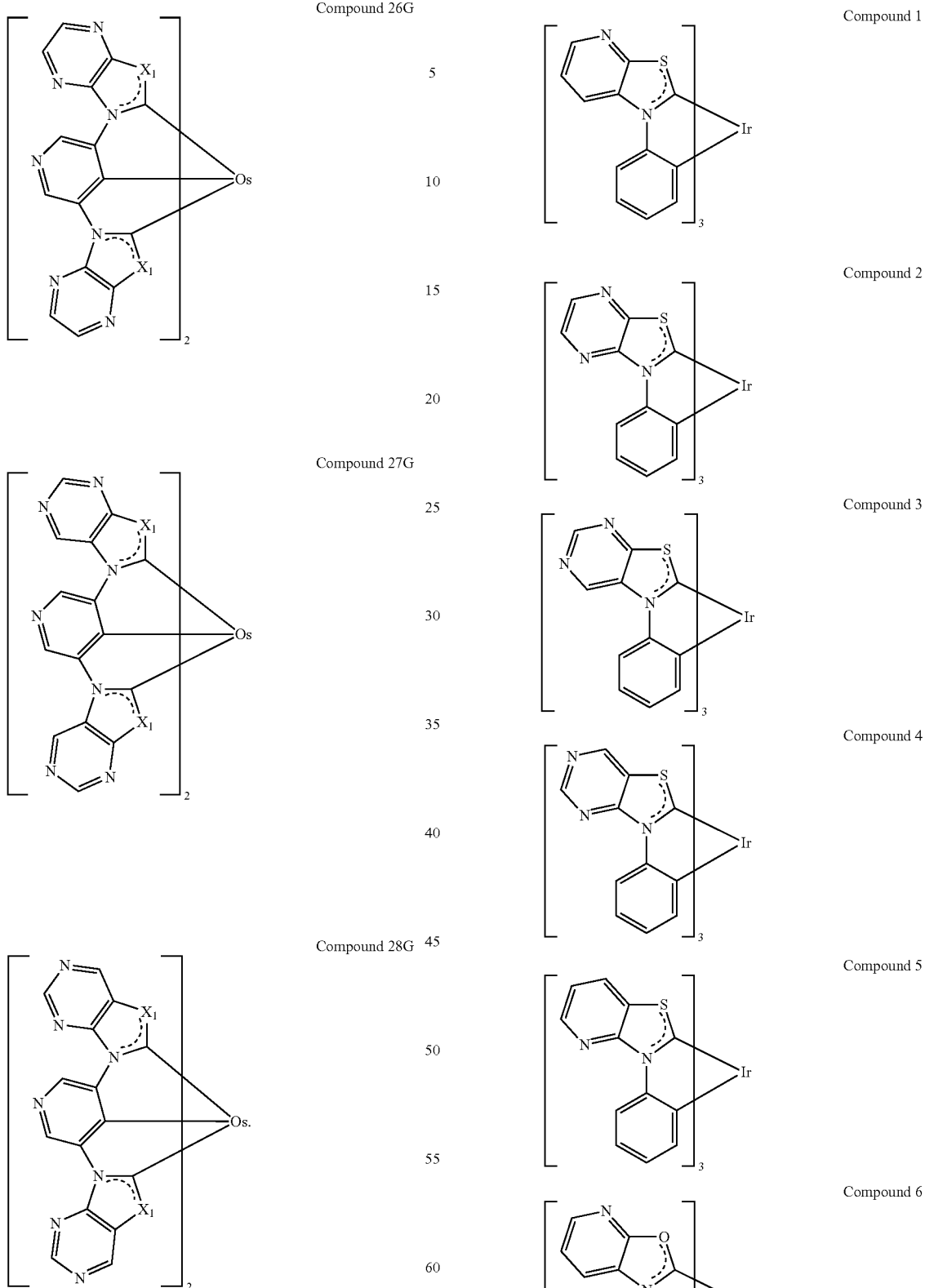
Compound 1
Compound 2
Compound 3
Compound 4
Compound 5
Compound 6

Compound 7
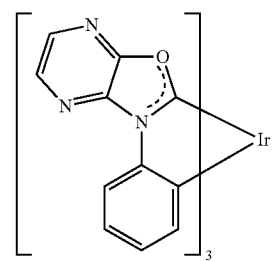
Compound 8
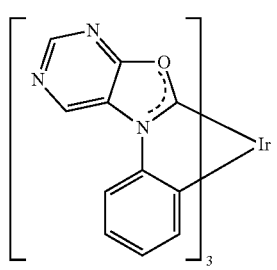
Compound 9
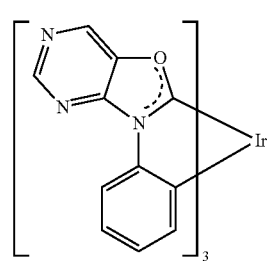
Compound 10
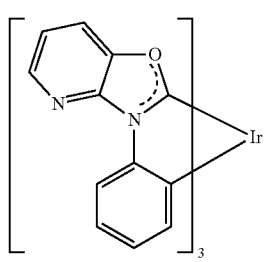
Compound 11
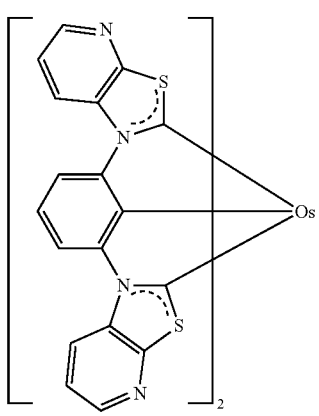
Compound 12
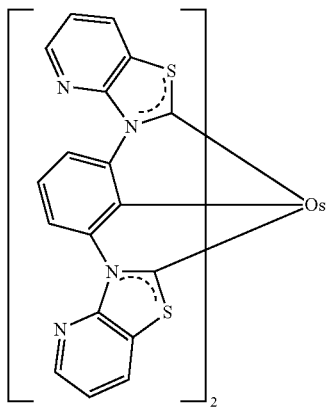
Compound 13
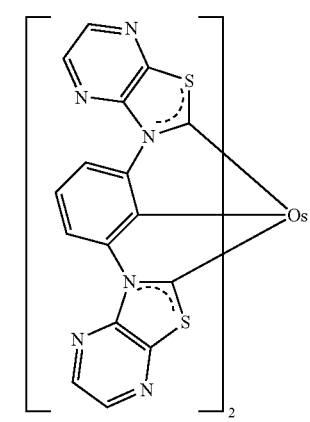
Compound 14
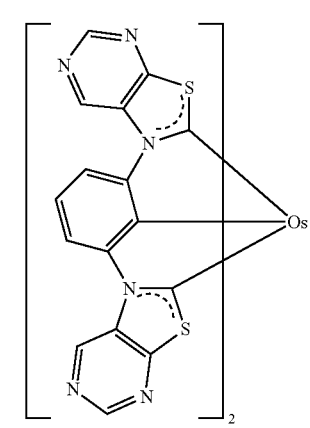
Compound 15
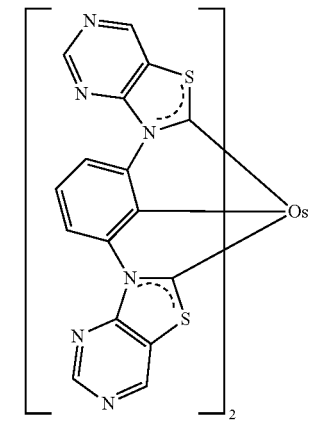

Compound 16

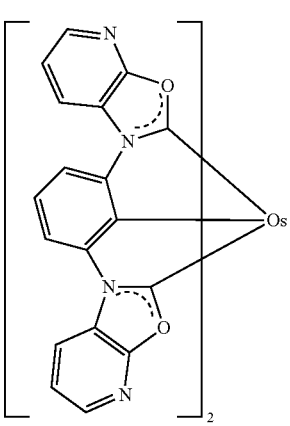

Compound 17

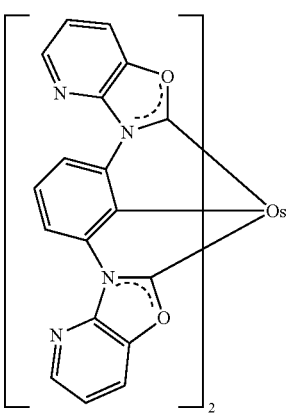

Compound 18

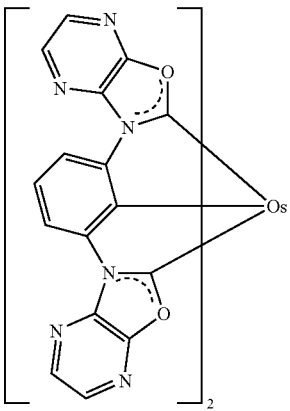

Compound 19

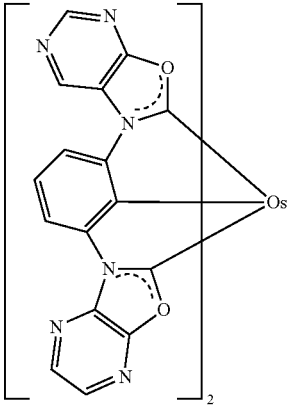

Compound 20

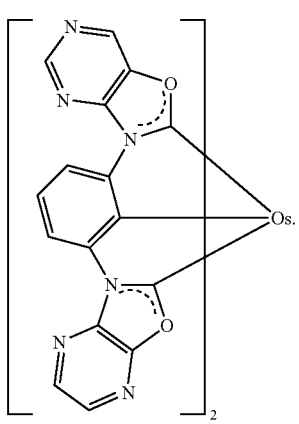

Additionally, a first device comprising an organic light emitting device is provided. The organic light emitting device further comprises an anode, a cathode, and an organic layer, disposed between the anode and the cathode. The organic layer comprises a compound comprising a ligand L having the structure:

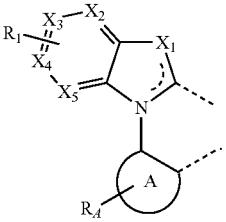

Formula I $X_1$ is S or O. $X_2$, $X_3$, $X_4$, and $X_5$ are independently C or N. At least one of $X_2$, $X_3$, $X_4$, and $X_5$ is N. $R_1$ may represent mono, di, tri or tetra substitutions. $R_1$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_1$ are optionally joined to form a fused ring. $R_A$ may represent mono, di, tri, or tetra substitutions. $R_A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_A$ are optionally joined to form a fused ring. A is a 5-membered or 6-membered carbocyclic or heterocyclic ring. Preferably, A is benzene. The ligand L is coordinated to a transition metal M having an atomic number greater than 40. Preferably, the metal M is Ir or Os. More preferably, the metal M is Os. More preferably, the metal M is Ir. The bidentate ligand may be linked with other ligands to comprise a tridentate, tetradentate, pentadentate or hexadentate ligand.

The various specific aspects discussed above for compounds having Formula I are also applicable to a compound having Formula I when used in the first device. In particular, the various specific aspects of $X_1$, $X_2$, $X_3$, $X_4$, $X_5$, $R_1$, $R_A$, and A of the compound having Formula I, as discussed above, are also applicable to the compound having Formula I that is used in the first device.

Specific examples of compounds that may be used in the device are provided. In one aspect, the compound is selected from the group consisting of Compound 1G-Compound 28G. Each $X_1$ is independently S or O. In another aspect, the compound is selected from the group consisting of Compound 1-Compound 20.

In one aspect, the organic layer is an emissive layer and the compound is an emissive dopant. In another aspect, the organic layer further comprises a host. Preferably, the host is a compound that comprises at least one of the chemical groups selected from the group consisting of:

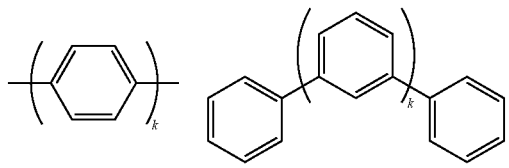

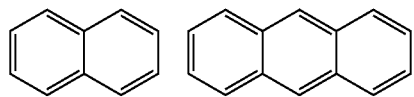

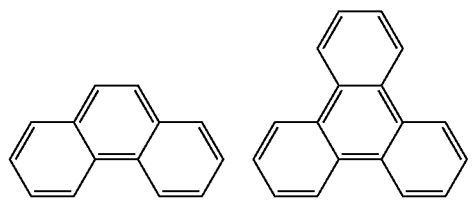

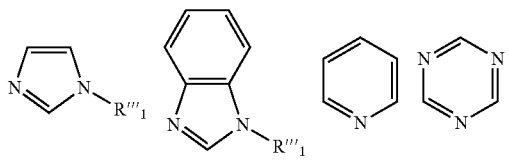

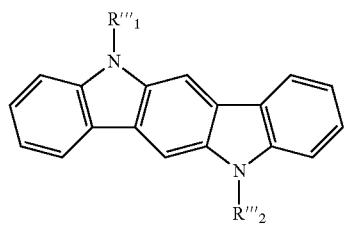

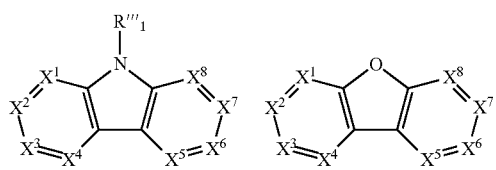

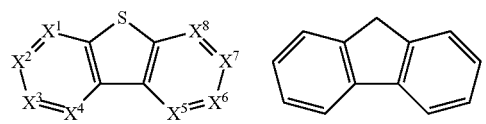

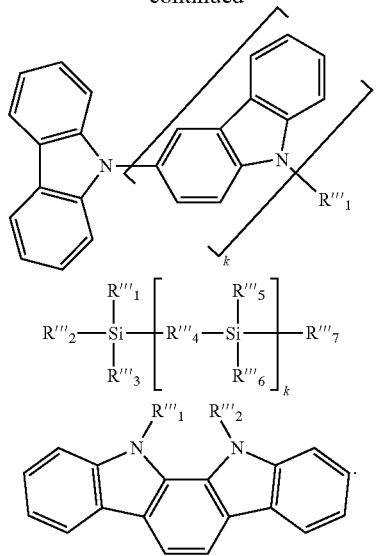

Each of $R'''_1$, $R'''_2$, $R'''_3$, $R'''_4$, $R'''_5$, $R'''_6$ and $R'''_7$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R'''_1$, $R'''_2$, $R'''_3$, $R'''_4$, $R'''_5$, $R'''_6$ and $R'''_7$ are optionally joined to form a fused ring. k is an integer from 0 to 20. Each of $X^1$, $X^2$, $X^3$, $X^4$, $X^5$, $X^6$, $X^7$ and $X^8$ are independently selected from the group consisting of CH and N.

In another aspect, the host is a metal complex. In yet another aspect, the metal complex is selected from the group consisting of:

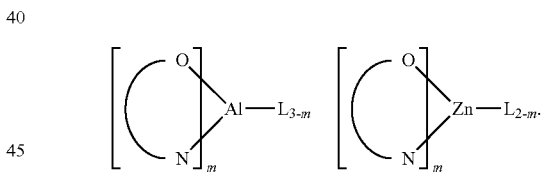

(O—N) is a bidentate ligand having metal coordinated to atoms O and N. L is an ancillary ligand. m is an integer value from 1 to the maximum number of ligands that may be attached to the metal.

In one aspect, the first device is a consumer product. In another aspect, the first device is an organic light emitting device.

A process for making a carbene metal complex is also provided. The process comprises reacting the copper dichloride carbene dimer with a metal precursor to yield the carbene metal complex. In one aspect, the process further comprises reacting a carbene salt with copper-t-butoxide to yield a copper dichloride carbene dimer, prior to reacting the copper dichloride carbene dimer with the metal precursor.

In one aspect, the metal is Ir, Os, Ru or Pt. In another aspect, the metal precursor is selected from the group consisting of [IrCl(COD)]$_2$, OsCl$_2$(DMSO)$_4$, RuCl$_2$(DMSO)$_4$, and PtCl$_2$(SEt$_2$)$_2$.

In one aspect, the carbene metal complex has the formula:

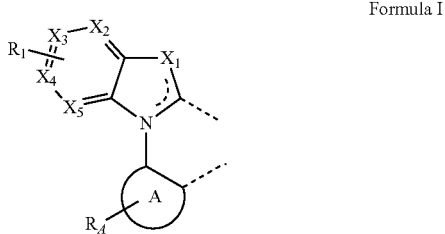

Formula I $X_1$ is $NR_B$, S or O. In one aspect, $X_1$ is $NR_B$. In another aspect, $X_1$ is S. In yet another aspect, $X_1$ is O. $X_2$, $X_3$, $X_4$, and $X_5$ are independently C or N. $R_1$ may represent mono, di, tri or tetra substitutions. $R_1$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof. Two adjacent substituents of $R_1$ are optionally joined to form a fused ring. $R_A$ may represent mono, di, tri, or tetra substitutions. $R_A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_A$ are optionally joined to form a fused ring. A is a 5-membered or 6-membered carbocyclic or heterocyclic ring. $R_B$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. The ligand L is coordinated to a transition metal M having an atomic number greater than 40. The bidentate ligand may be linked with other ligands to comprise a tridentate, tetradentate, pentadentate or hexadentate ligand.

In one aspect, the carbene metal complex is heteroleptic. In another aspect, the carbene metal complex is homoleptic. Preferably, the carbene metal complex is tris configuration.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
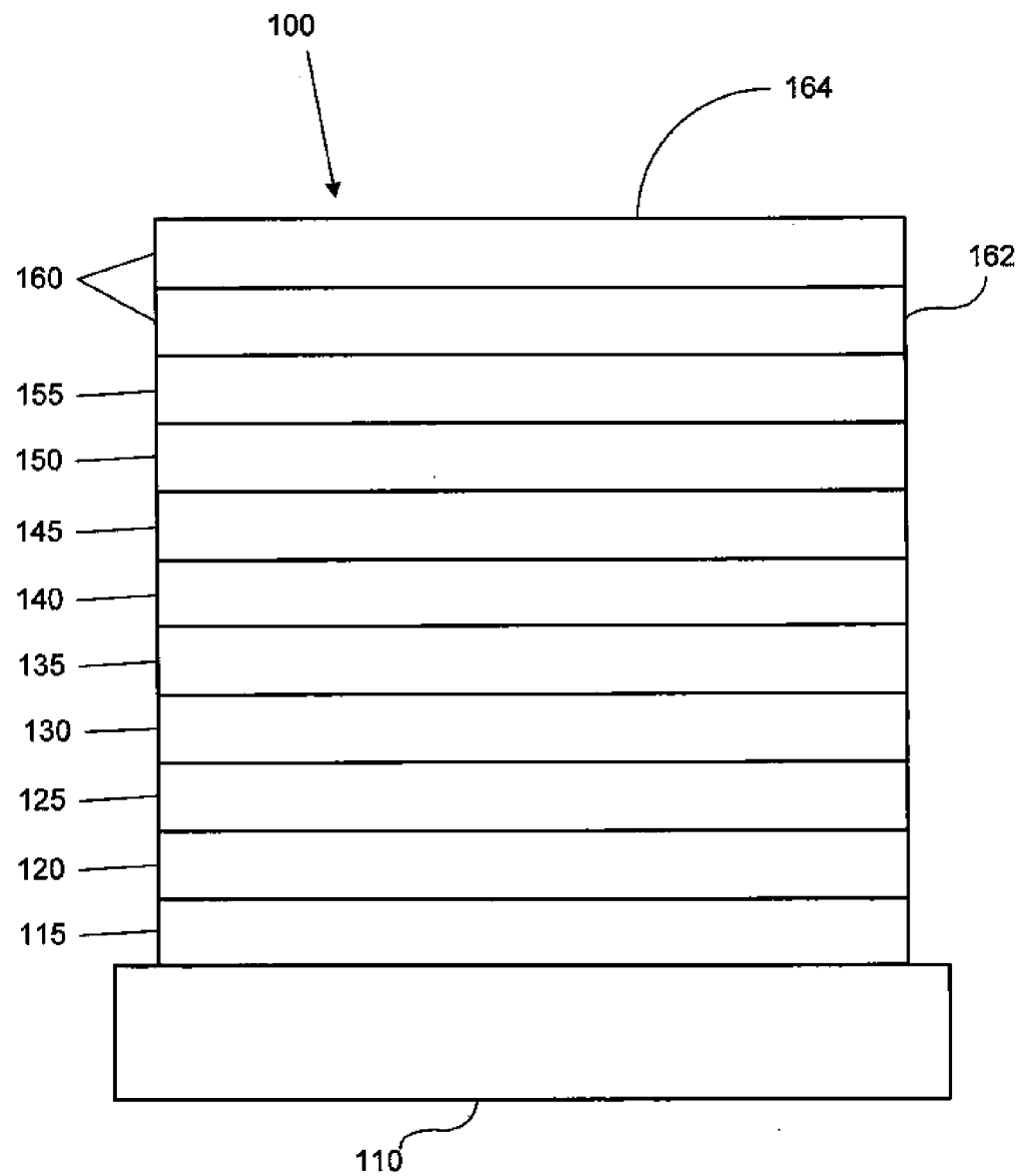
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
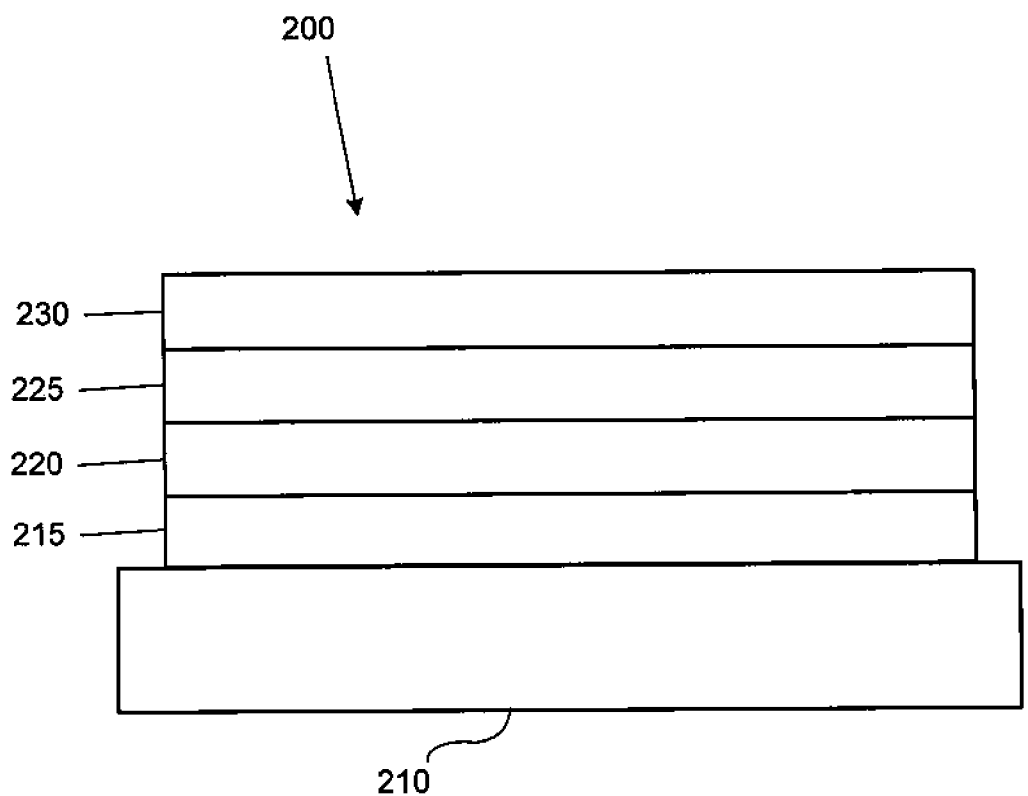
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
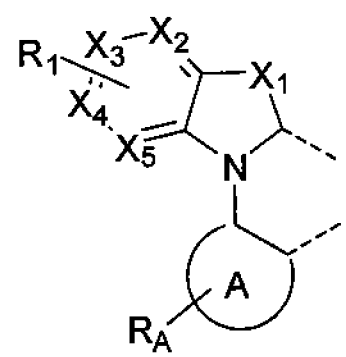
FIG. 3 shows a carbene ligand.

Carbene iridium complexes are new class of phosphorescent dopant materials, which can provide various colors when used as emissive dopants in an OLED device. An overwhelming majority of N heterocyclic carbenes (NHC) ligands are derived from the imidazole ($C_3H_4N_2$) framework. As research in NHC carbene metal complexes in OLEDs continues to advance at a vigorous pace, there is a strong need to develop other heterocyclic systems that can be adapted to the demands of different OLED materials. In particular, compounds in which one of the N atoms in an imidazole is replaced with an O atom to form an oxazole or with an S atom to form a thioazole are provided herein (as illustrated in FIG. 3). Additionally, a novel methodology to synthesize heterocyclic carbene metal complexes is provided. These compounds may lead to unique device properties in OLEDs, including improved stability and improved color-tuning.

There are many beneficial features of the heterocyclic carbene metal complexes provided herein, including a reducible carbene moiety, i.e., reversible reduction, short excited state lifetime and a novel ligation method. First, imidazole-based carbene metal complexes generally do not have reversible reduction by CV measurement. In general, imidazole-based carbenes have a high LUMO that is difficult to reduce. This can lead to extremely high LUMO and electron instability. The oxazole and thioazole heterocyclic-based carbene metal complexes provided herein have reversible reduction and a shallow LUMO. Without being bound by theory, it is believed that the reversible reduction may improve the electron stability of these compounds when used as a dopant. By using the oxazole and thioazole heterocyclic carbenes configuration, the carbene moiety may become more reducible. With a N-containing aromatic ring fused into this heterocyclic carbene ring, the LUMO level may be further reduced. In other words, it may be easier to lower the LUMO of oxazole and thioazole heterocyclic carbenes compared to imidazole-based carbenes, which may allow for better device stability.

Second, iridium carbene complexes generally have a long excited state lifetime due to poor MLCT mixing. The oxazole and thioazole heterocyclic carbene metal complexes provided herein, however, may have shorter excited state lifetimes. Fusion of a N-containing aromatic ring to this heterocyclic carbene ring is not expected to alter the shortened excited state lifetime demonstrated by these compounds.

Third, the traditional ligation method via $Ag_2O$ fails for these heterocyclic based carbene metal complexes. These heterocyclic carbenes are more difficult to attach to metals than their corresponding imidazole carbene counterparts. Therefore, a new ligation method via copper carbene complexes has been developed. The free carbene stability for N, S-based carbenes is worse than conventional imidazole-based carbenes due to the lack of steric protection. Without being bound by theory, it is believed that the conventional transmetallation via $Ag_2O$ was not successful for the oxazole and thioazole heterocyclic carbenes because the oxazole and thioazole free carbene is less stable than imidazole carbene due to less steric protection for the carbene center in the oxazole and thioazole carbenes. The novel method developed for synthesis of these heterocyclic carbene complexes includes reacting a carbene precursor salt with copper-t-butoxide to yield a cooper dichloride carbene dimer, which is then transmetallated to a metal precursor to yield heterocyclic carbene metal complexes. In particular, the method may be used to make tris heterocyclic carbene metal complexes.

Heterocyclic carbene metal complexes are provided. The compounds comprise a ligand L having the structure:

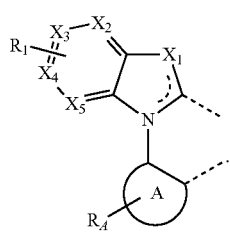

Formula I $X_1$ is S or O. $X_2$, $X_3$, $X_4$, and $X_5$ are independently C or N. At least one of $X_2$, $X_3$, $X_4$, and $X_5$ is N. $R_1$ may represent mono, di, tri or tetra substitutions. $R_1$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_1$ are optionally joined to form a fused ring. $R_A$ may represent mono, di, tri, or tetra substitutions. $R_A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_A$ are optionally joined to form a fused ring. A is a 5-membered or 6-membered carbocyclic or heterocyclic ring. Preferably, A is benzene. The ligand L is coordinated to a transition metal M having an atomic number greater than 40. Preferably, the metal M is Ir or Os. More preferably, the metal M is Ir. Additionally, the metal M is preferably Os. The bidentate ligand L may be linked with other ligands to comprise a tridentate, tetradentate, pentadentate or hexadentate ligand.

In one aspect, the ligand has the formula:

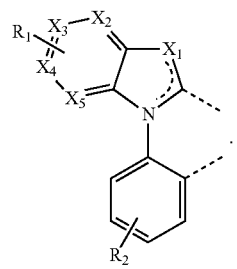

Formula II

At least one of $X_2$, $X_3$, $X_4$, and $X_5$ is N. $R_2$ may represent mono, di, tri or tetra substitutions. $R_2$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof. Two adjacent substituents of $R_2$ are optionally joined to form a fused ring.

In another aspect, the ligand has the formula:

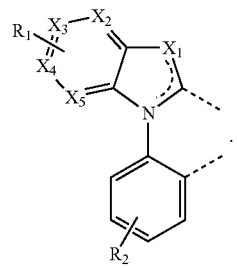

Formula II

At least two of $X_2$, $X_3$, $X_4$, and $X_5$ is N. $R_2$ may represent mono, di, tri or tetra substitutions. $R_2$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_2$ are optionally joined to form a fused ring.

In one aspect, the compound is heteroleptic. In another aspect, the compound is homoleptic. In yet another aspect, the compound has the formula:

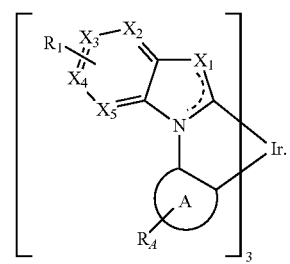

Formula III

Specific examples of the heterocyclic carbene compounds are provided. In one aspect, the compound is selected from the group consisting of:

Compound 1G
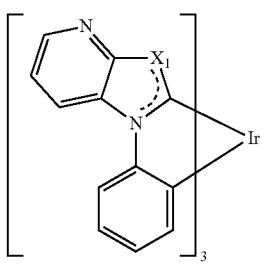
Compound 2G
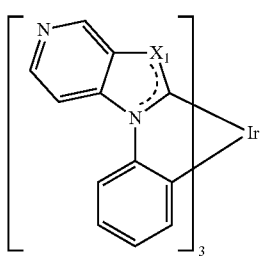
Compound 3G
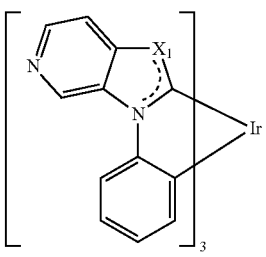
Compound 4G
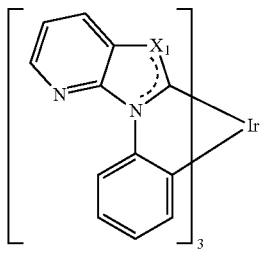
Compound 5G
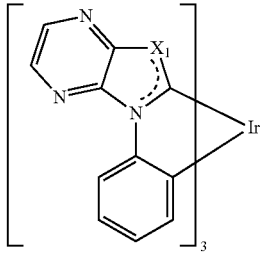
Compound 6G
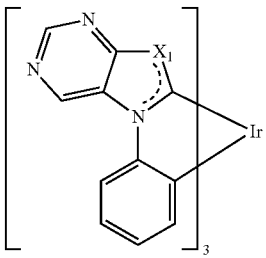
-continued
Compound 7G
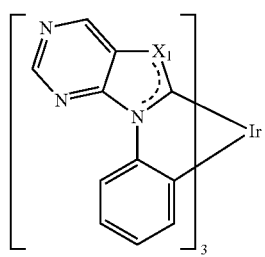
Compound 8G
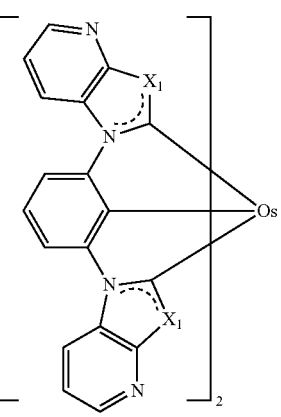
Compound 9G
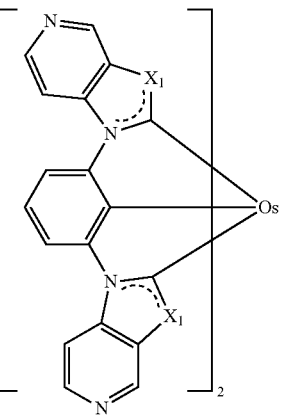
Compound 10G
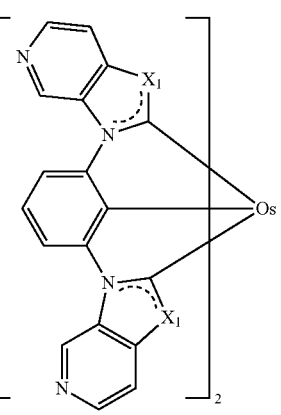

Compound 11G
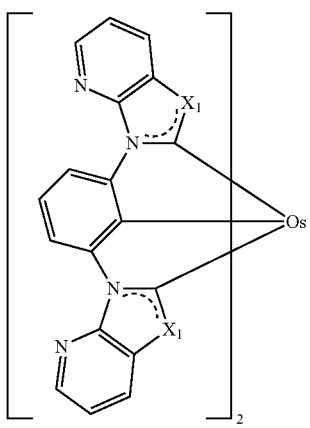
Compound 12G
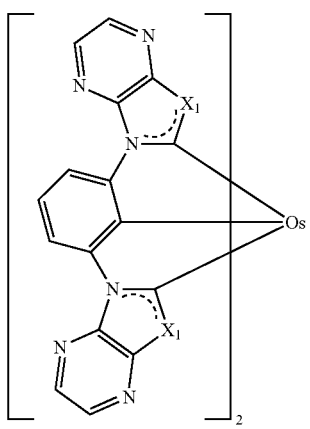
Compound 13G
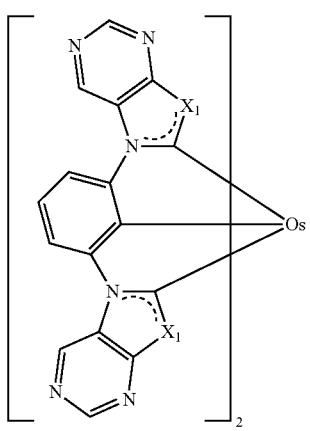
Compound 14G
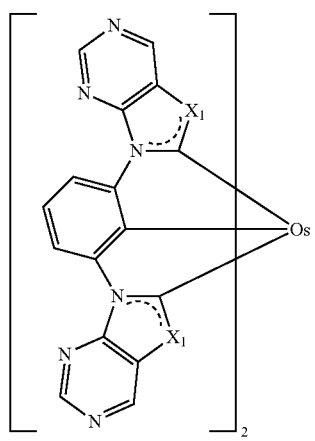
Compound 15G
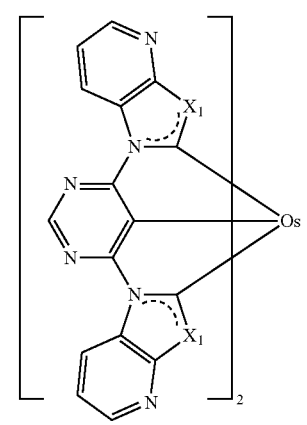
Compound 16G
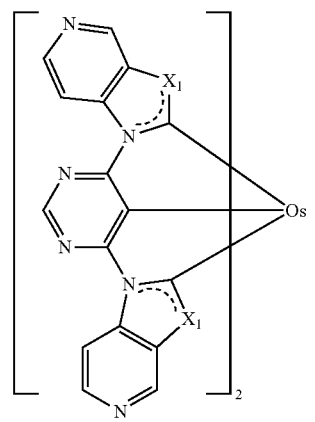

Compound 17G
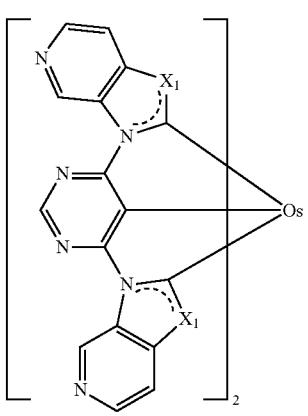
Compound 18G
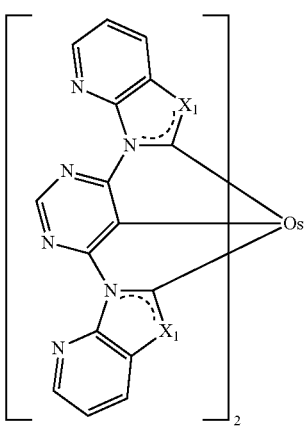
Compound 19G
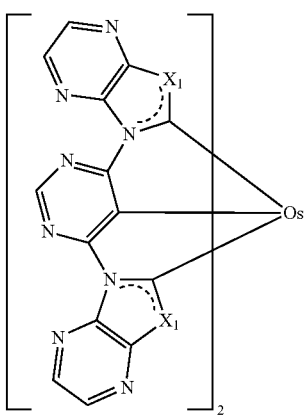
Compound 20G
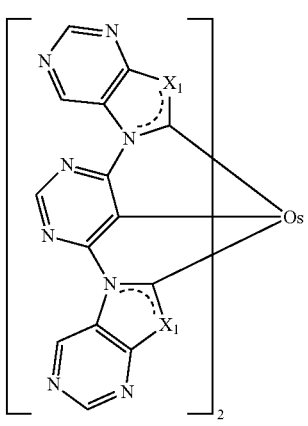
Compound 21G
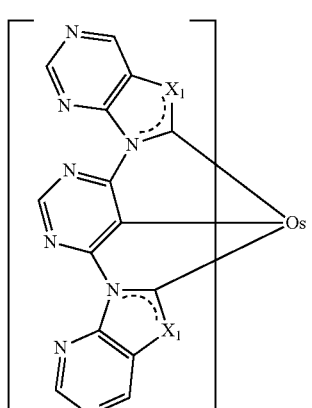
Compound 22G
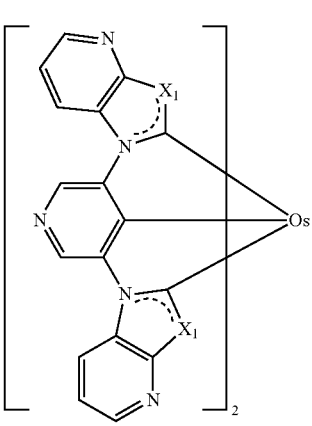
Compound 23G
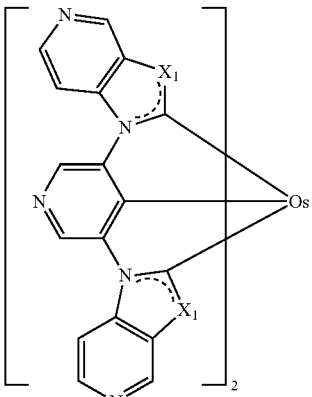
Compound 24G
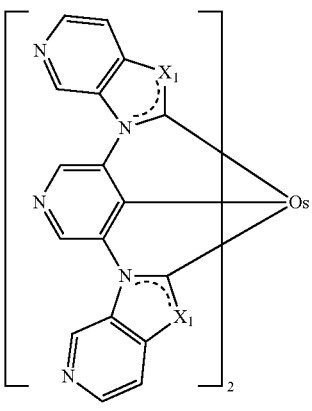

Compound 25G
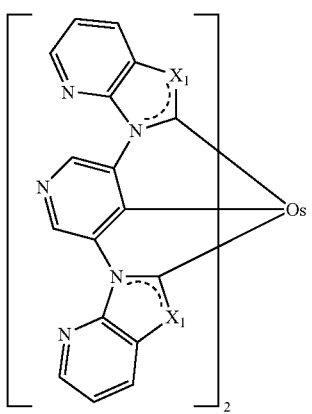
Compound 28G
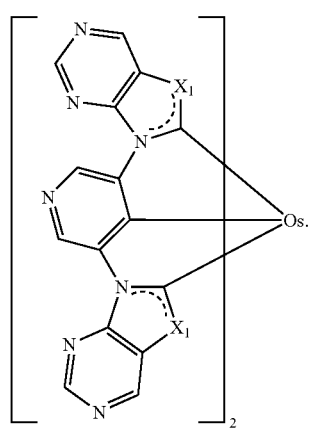
Each $X_1$ is independently S or O.
Additional specific examples of heterocyclic carbene compounds are provided. In one aspect, the compound is selected from the group consisting of:
Compound 26G
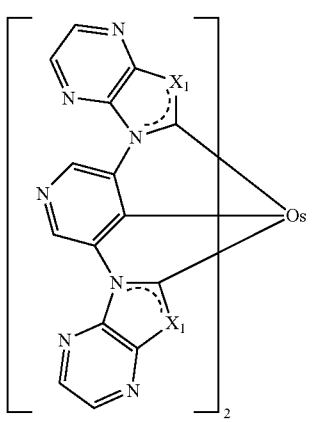
Compound 1
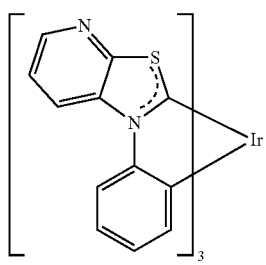
Compound 2
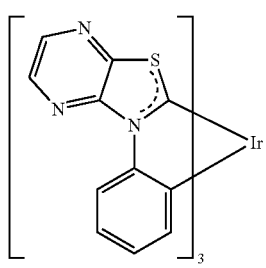
Compound 27G
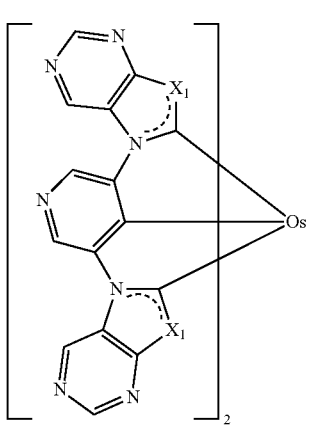
Compound 3
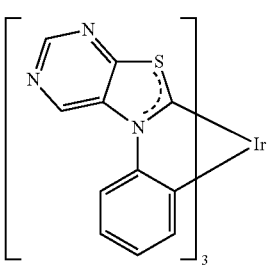

Compound 4
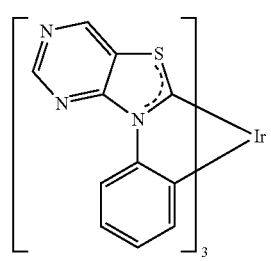
Compound 5
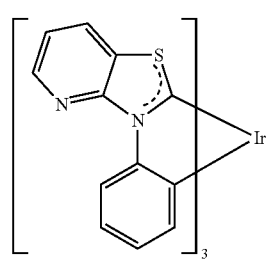
Compound 6
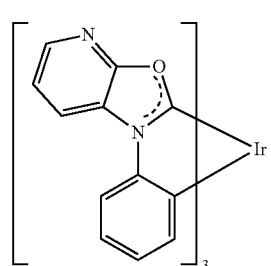
Compound 7
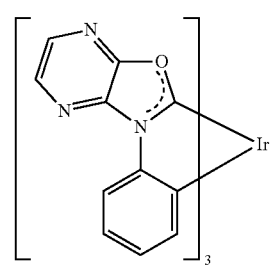
Compound 8
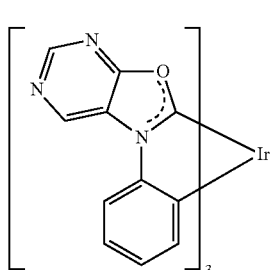
Compound 9
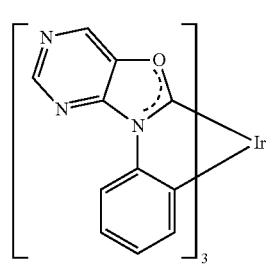
Compound 10
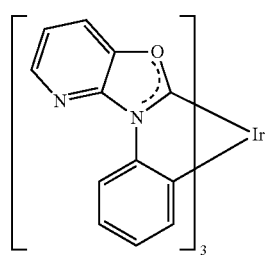
Compound 11
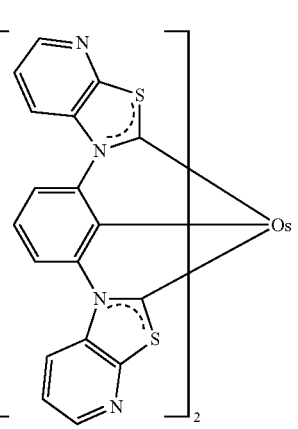
Compound 12
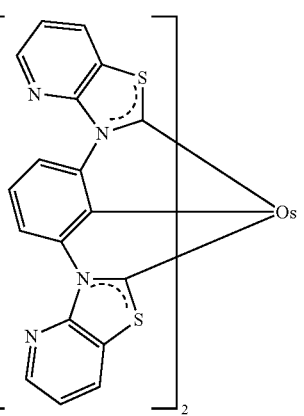
Compound 13
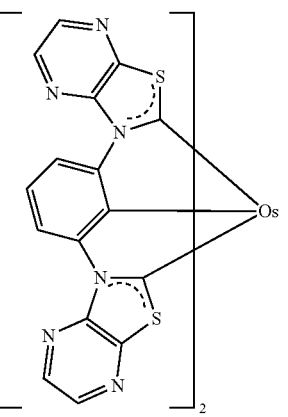

Compound 14

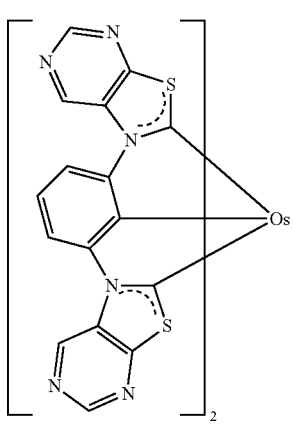

Compound 15

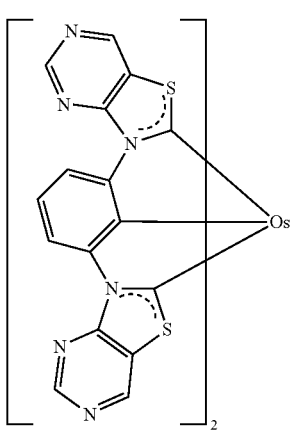

Compound 16

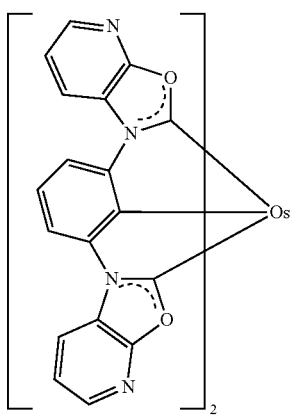

Compound 17

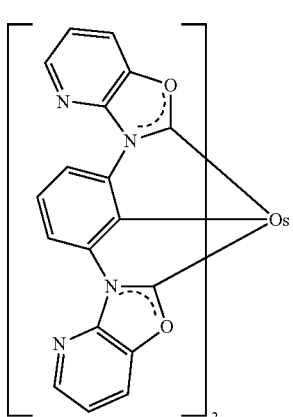

Compound 18

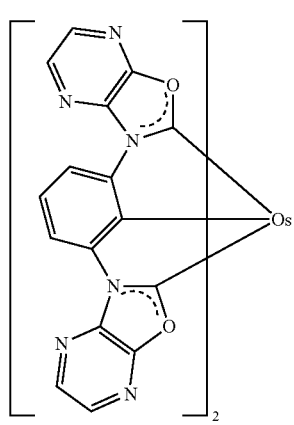

Compound 19

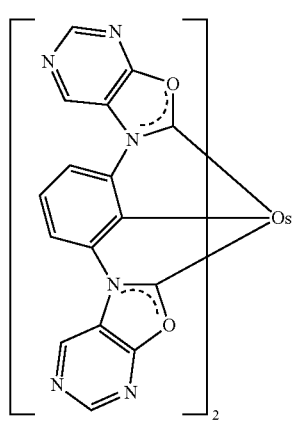

Compound 20

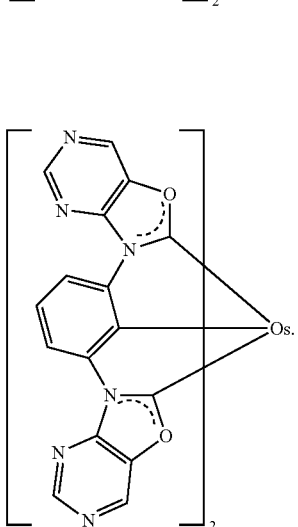

Additionally, a first device comprising an organic light emitting device is provided. The organic light emitting device further comprises an anode, a cathode, and an organic layer, disposed between the anode and the cathode. The organic layer comprises a compound comprising a ligand L having the structure:

Formula I

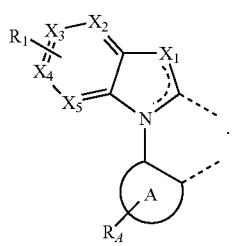

$X_1$ is S or O. $X_2$, $X_3$, $X_4$, and $X_5$ are independently C or N. At least one of $X_2$, $X_3$, $X_4$, and $X_5$ is N. $R_1$ may represent mono, di, tri or tetra substitutions. $R_1$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_1$ are optionally joined to form a fused ring. $R_A$ may represent mono, di, tri, or tetra substitutions. $R_A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_A$ are optionally joined to form a fused ring. A is a 5-membered or 6-membered carbocyclic or heterocyclic ring. Preferably, A is benzene. The ligand L is coordinated to a transition metal M having an atomic number greater than 40. Preferably, the metal M is Ir or Os. More preferably, the metal M is Os. More preferably, the metal M is Ir. The bidentate ligand may be linked with other ligands to comprise a tridentate, tetradentate, pentadentate or hexadentate ligand.

In one aspect, the ligand has the formula:

Formula II

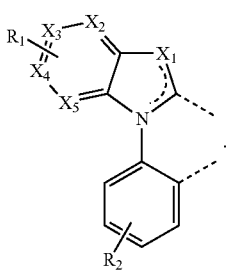

At least one of $X_2$, $X_3$, $X_4$, and $X_5$ is N. $R_2$ may represent mono, di, tri or tetra substitutions. $R_2$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_2$ are optionally joined to form a fused ring.

In another aspect, the ligand has the formula:

Formula II

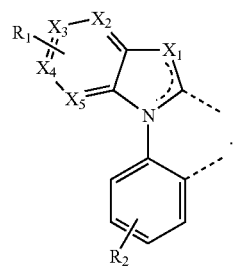

At least two of $X_2$, $X_3$, $X_4$, and $X_5$ is N. $R_2$ may represent mono, di, tri or tetra substitutions. $R_2$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_2$ are optionally joined to form a fused ring.

In one aspect, the compound is heteroleptic. In another aspect, the compound is homoleptic. In yet another aspect, the homoleptic compound has the formula:

Formula III

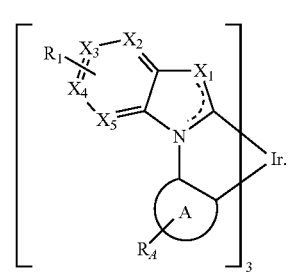

Specific examples of compounds that may be used in the device are provided. In one aspect, the compound is selected from the group consisting of Compound 1G-Compound 28G. Each $X_1$ is independently S or O.

In another aspect, the compound is selected from the group consisting of Compound 1 Compound 20.

In one aspect, the organic layer is an emissive layer and the compound is an emissive dopant. In another aspect, the organic layer further comprises a host. Preferably, the host is a compound that comprises at least one of the chemical groups selected from the group consisting of:

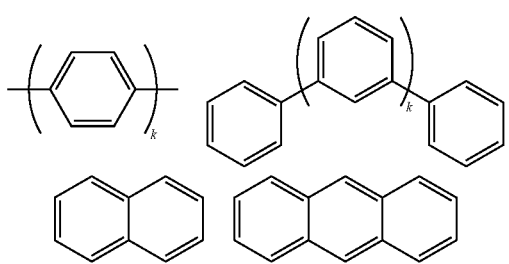

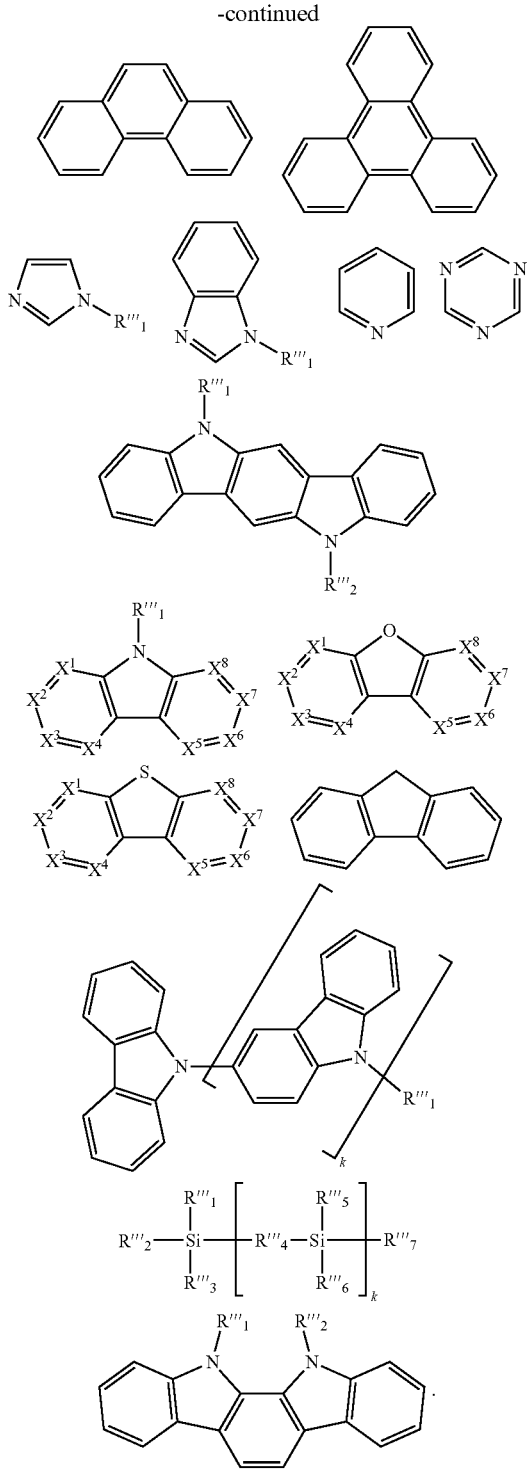

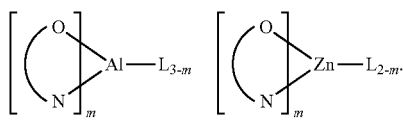

(O—N) is a bidentate ligand having metal coordinated to atoms O and N. L is an ancillary ligand. m is an integer value from 1 to the maximum number of ligands that may be attached to the metal.

In one aspect, the first device is a consumer product. In another aspect, the first device is an organic light emitting device.

A process for making a carbene metal complex is also provided. The process comprises reacting the copper dichloride carbene dimer with a metal precursor to yield the carbene metal complex. In one aspect, the process further comprises reacting a carbene salt with copper-t-butoxide to yield a copper dichloride carbene dimer, prior to reacting the copper dichloride carbene dimer with the metal precursor.

In one aspect, the metal is Ir, Os, Ru or Pt. In another aspect, the metal precursor is selected from the group consisting of [IrCl(COD)]$_2$, OsCl$_2$(DMSO)$_4$, RuCl$_2$(DMSO)$_4$, and PtCl$_2$(SEt$_2$)$_2$.

In one aspect, the carbene metal complex has the formula:

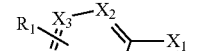

Formula I $X_1$ is $NR_B$, S or O. In one aspect, $X_1$ is $NR_B$. In another aspect, $X_1$ is S. In yet another aspect, $X_1$ is O. $X_2$, $X_3$, $X_4$, and $X_5$ are independently C or N. $R_1$ may represent mono, di, tri or tetra substitutions. $R_1$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, isonitrile, sulfanyl, sulfinyl, sulfonyl, phosphino, and combinations thereof. Two adjacent substituents of $R_1$ are optionally joined to form a fused ring. $R_A$ may represent mono, di, tri, or tetra substitutions. $R_A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_A$ are optionally joined to form a fused ring. A is a 5-membered or 6-membered carbocyclic or heterocyclic ring. $R_B$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. The ligand L is coordinated to a transition metal M having an atomic num- Each of R'''$_1$, R'''$_2$, R'''$_3$, R'''$_4$, R'''$_5$, R''' and R'''$_7$ are independently selected from the group consisting of hydrogen, deuterium, alkyl, alkoxy, amino, alkenyl, alkynyl, arylalkyl, heteroalkyl, aryl and heteroaryl. k is an integer from 0 to 20. Each of X$^1$, X$^2$, X$^3$, X$^4$, X$^5$, X$^6$, X$^7$ and X$^8$ are independently selected from the group consisting of CH and N.

In another aspect, the host is a metal complex. In yet another aspect, the metal complex is selected from the group consisting of:

ber greater than 40. The bidentate ligand may be linked with other ligands to comprise a tridentate, tetradentate, pentadentate or hexadentate ligand.

In one aspect, the carbene metal complex is heteroleptic. In another aspect, the carbene metal complex is homoleptic. Preferably, the carbene metal complex is iris.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and slime derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

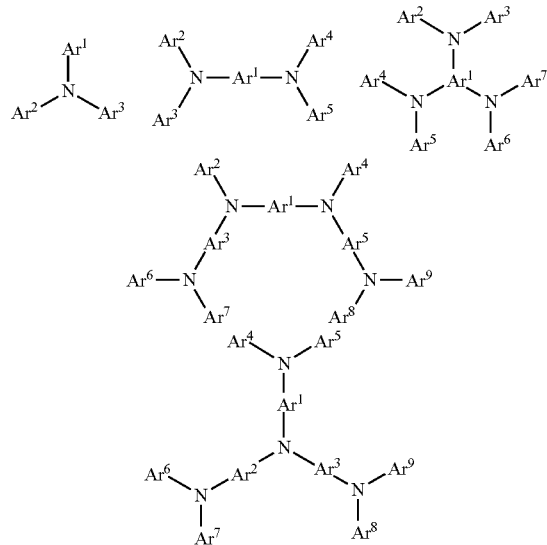

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents are optionally joined to form a fused ring.

In one aspect, $Ar^1$ to $Ar^9$ is independently selected from the group consisting of:

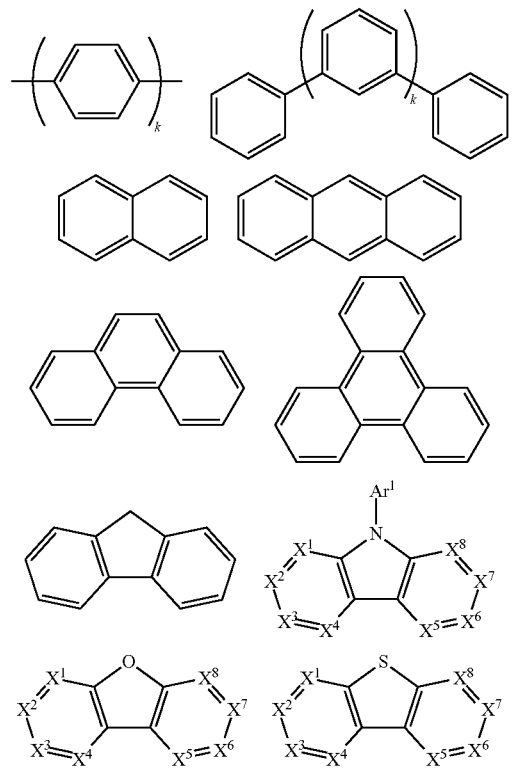

k is an integer from 1 to 20; $X^1$ to $X^8$ is CH or N; $Ar^1$ has the same group defined above.

Examples of metal complexes used in HIL or HTL include, but not limit to the following general formula:

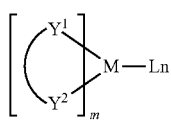

M is a metal, having an atomic weight greater than 40; $(Y^1—Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1—Y^2)$ is a 2-phenylpyridine derivative.

In another aspect, $(Y^1—Y^2)$ is a carbene ligand.

In another aspect, M is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

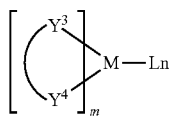

M is a metal; $(Y^3—Y^4)$ is a bidentate ligand, $Y^3$ and $Y^4$ are independently selected from C, N, O, P, and 5; L is an ancillary ligand; m is an integer value from 1 to the maximum number of ligands that may be attached to the metal; and m+n is the maximum number of ligands that may be attached to the metal.

In one aspect, the metal complexes are:

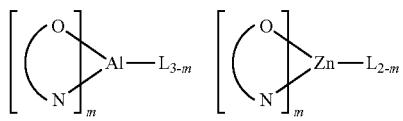

(O—N) is a bidentate ligand, having metal coordinated to atoms O and N.

In another aspect, M is selected from Ir and Pt.

In a further aspect, $(Y^3—Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, triazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents are optionally joined to form a fused ring.

In one aspect, host compound contains at least one of the following groups in the molecule:

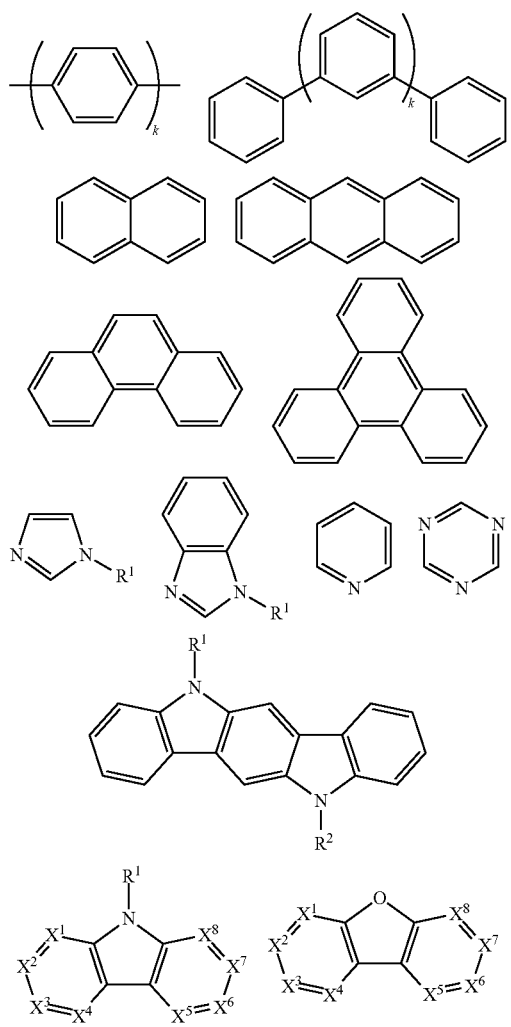

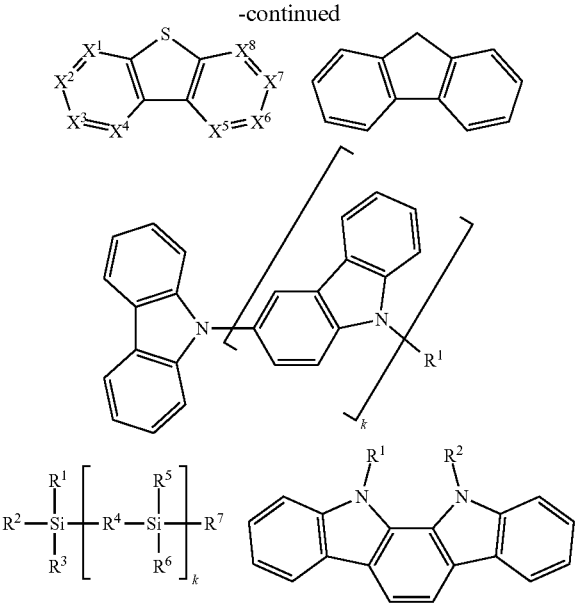

R[1] to R[7] is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents are optionally joined to form a fused ring. When it is aryl or heteroaryl, it has the similar definition as Ar's mentioned above.

k is an integer from 0 to 20.

X[1] to X[8] is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

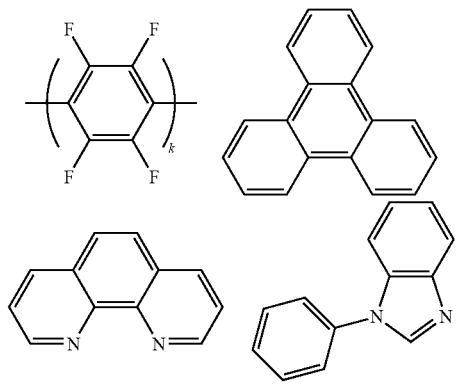

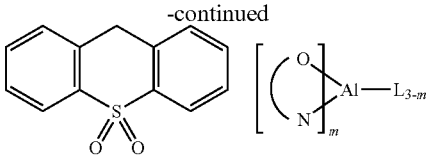

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

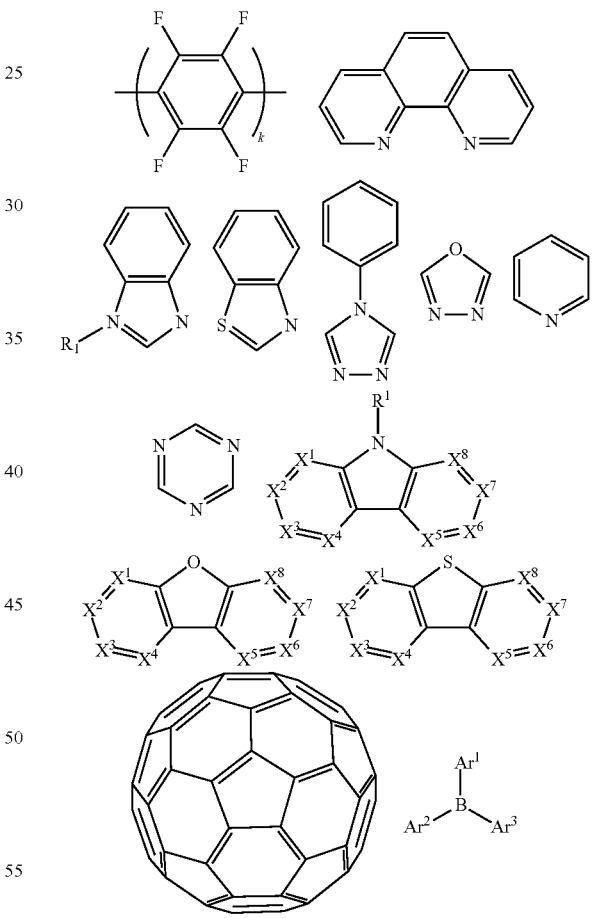

R[1] is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents are optionally joined to form a fused ring. When it is aryl or heteroaryl, it has the similar definition as Ar's mentioned above.

Ar¹ to Ar³ has the similar definition as Ar's mentioned above.

k is an integer from 0 to 20.

X¹ to X⁸ is selected from CH or N.

In another aspect, the metal complexes used in ETL contains, but not limit to the following general formula:

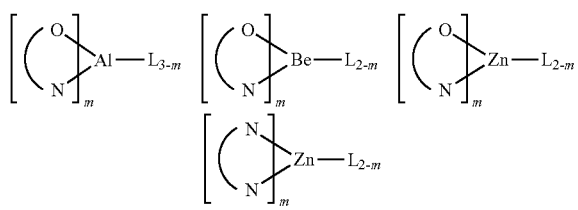

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phthalocyanine and porphryin compounds | | Appl. Phys. Lett. 69, 2160 (1996) |
| Starburst triarylamines | | J. Lumin. 72-74, 985 (1997) |
| CF$_x$ Fluorohydrocarbon polymer | —[CH$_x$F$_y$]$_n$— | Appl. Phys. Lett. 78, 673 (2001) |

TABLE 1-continued
| MATERIAL | EXAMPLES OF MATERIAL | PUBLICATIONS |
| --- | --- | --- |
| Conducting polymers (e.g., PEDOT:PSS, polyaniline, polypthiophene) | 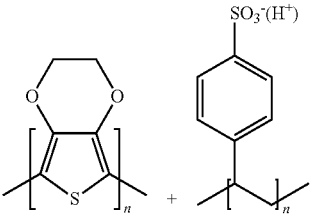 | Synth. Met. 87, 171 (1997)<br>WO2007002683 |
| Phosphonic acid and silane SAMs | 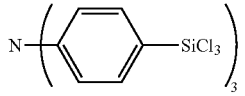 | US20030162053 |
| Triarylamine or polythiophene polymers with conductivity dopants | 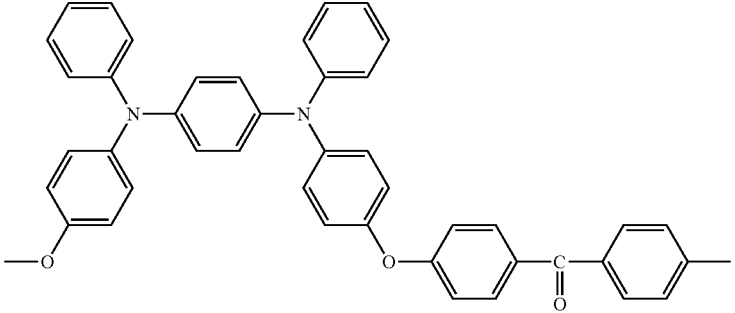<br>and<br>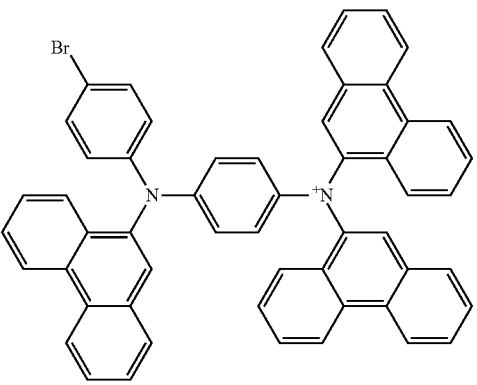 [SMILES: Brc1ccc(N(c2ccc([NH+](c3cc4ccccc4c4ccccc34)c3cc4ccccc4c4ccccc34)cc2)c2cc3ccccc3c3ccccc23)cc1]<br>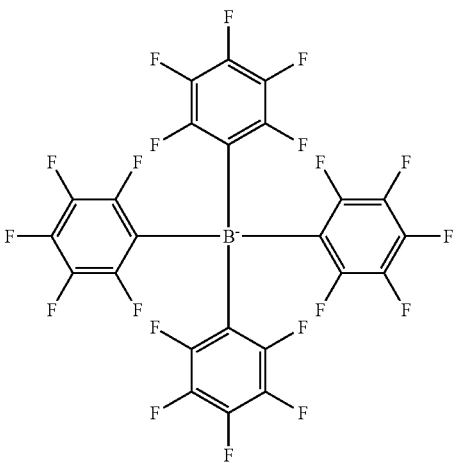 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EA01725079A1 |

TABLE 1-continued
| MATERIAL | EXAMPLES OF MATERIAL | PUBLICATIONS |
|---|---|---|
| Arylamines complexed with metal oxides such as molybdenum and tungsten oxides | 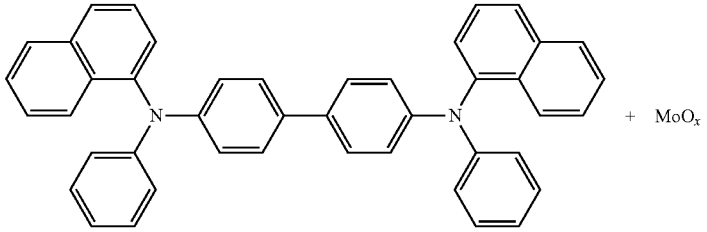 [SMILES: c1ccc(N(c2ccc(-c3ccc(N(c4ccccc4)c4cccc5ccccc45)cc3)cc2)c2cccc3ccccc23)cc1] + MoO$_x$ | SID Symposium Digest, 37, 923 (2006) WO2009018009 |
| Semiconducting organic complexes | 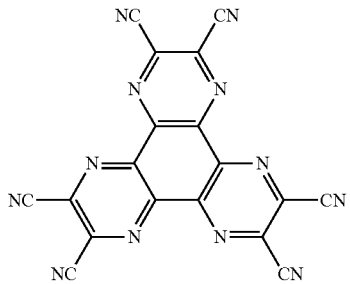 [SMILES: N#Cc1nc2c3nc(C#N)c(C#N)nc3c3nc(C#N)c(C#N)nc3c2nc1C#N] | US20020158242 |
| Metal organometallic complexes | 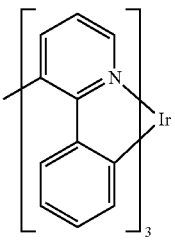 | US20060240279 |
| Cross-linkable compounds | 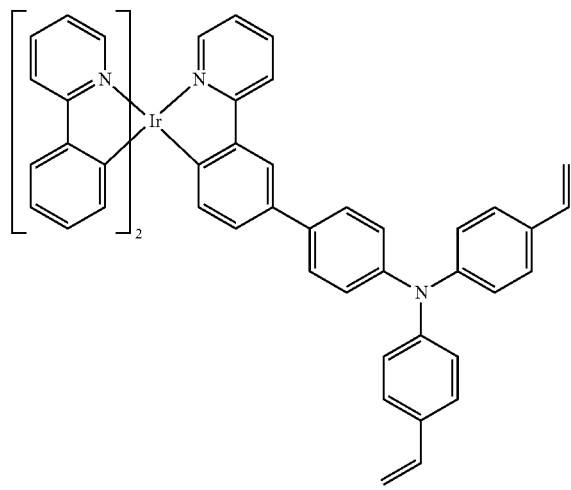 | US20080220265 |
| Hole transporting materials | | |
| Triarylamines (e.g. TPD, α-NPD) | 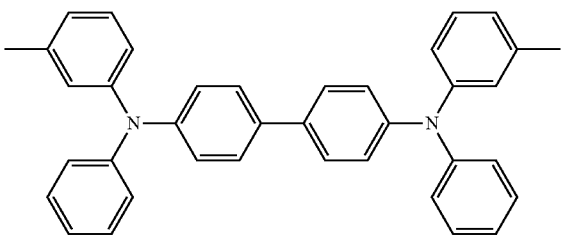 | Appl. Phys. Lett. 51, 913 (1987) |

TABLE 1-continued
| MATERIAL | EXAMPLES OF MATERIAL | PUBLICATIONS |
|---|---|---|
| | 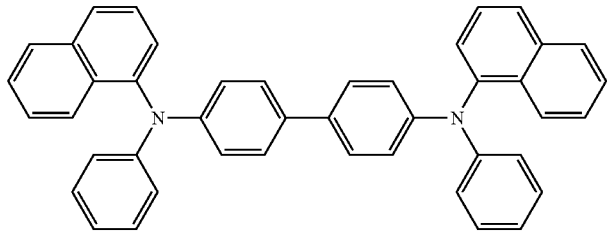 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 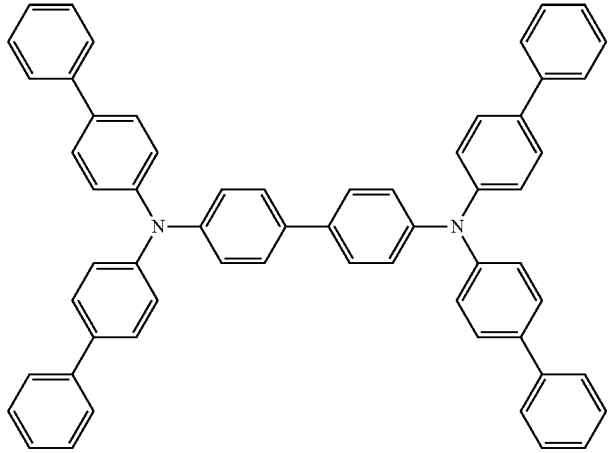 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 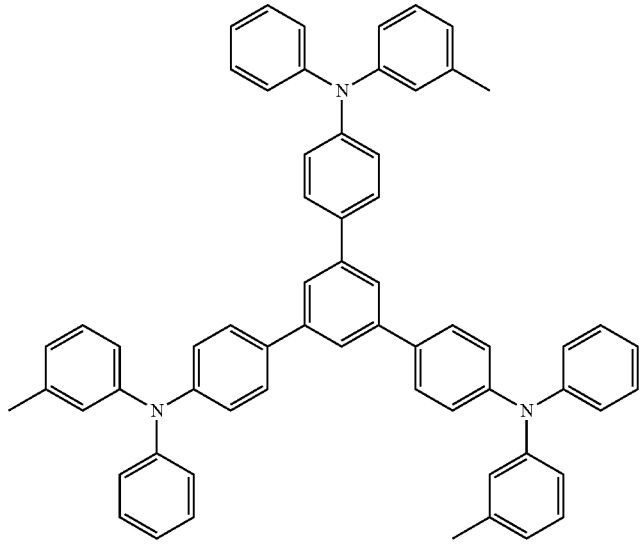 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 1-continued
| MATERIAL | EXAMPLES OF MATERIAL | PUBLICATIONS |
|---|---|---|
| | 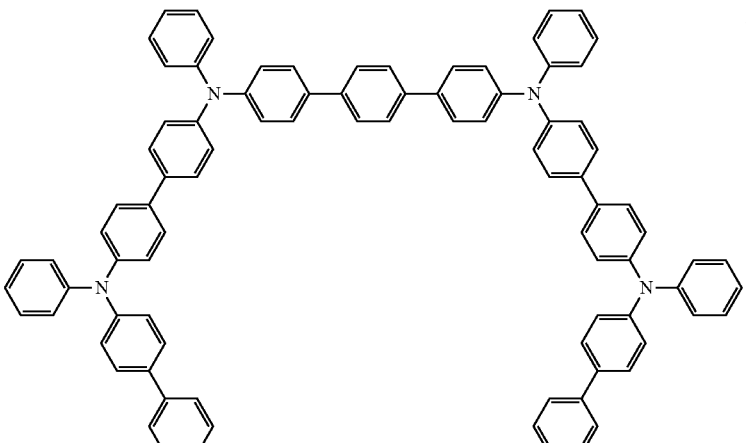 | Appl. Phys. Lett. 90, 183503 (2007) |
| | 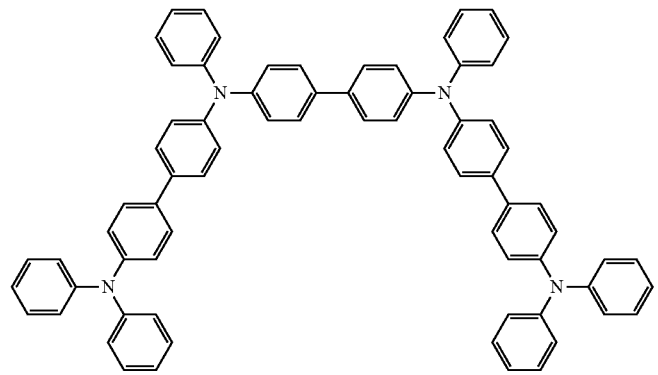 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triarylamine on spirofluorene core | 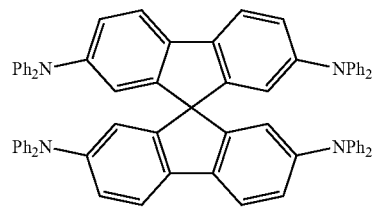 | Synth. Met. 91, 209 (1997) |
| Arylamine carbazole compounds | 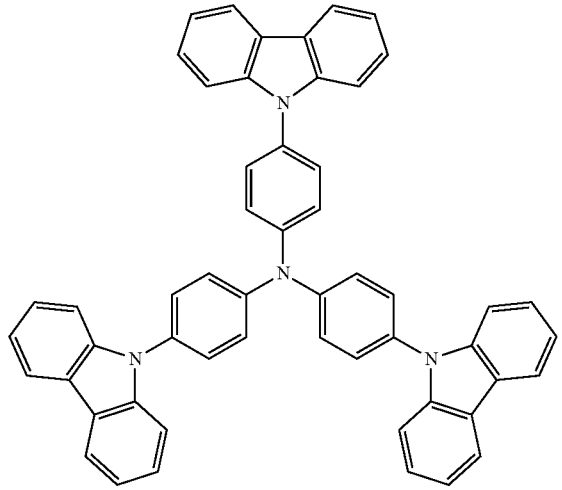 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |

TABLE 1-continued
| MATERIAL | EXAMPLES OF MATERIAL | PUBLICATIONS |
|---|---|---|
| Triarylamine with (di)benzothiophene/ (di)benzofuran | 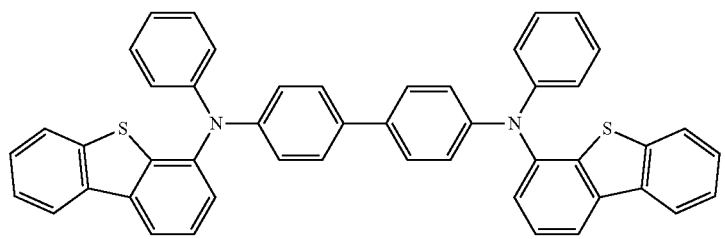 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 |
| Indolocarbazoles | 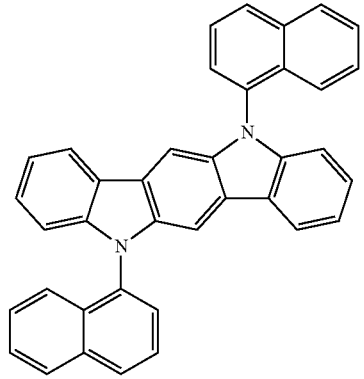 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 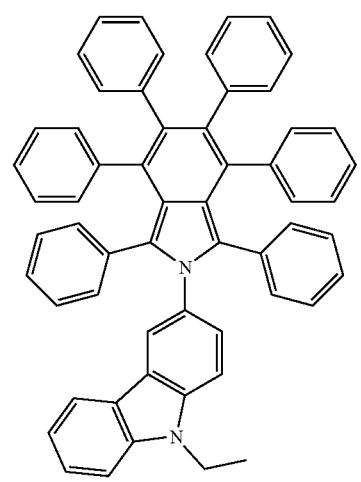 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 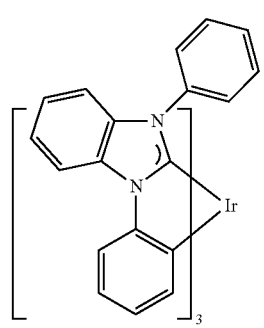 | US20080018221 |

TABLE 1-continued

| MATERIAL | EXAMPLES OF MATERIAL | PUBLICATIONS |
|---|---|---|
| | Phosphorescent OLED host materials | |
| | Red hosts | |
| Arylcarbazoles | | Appl. Phys. Lett. 78, 1622 (2001) |
| Metal 8-hydroxyquinolates (e.g. Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |

TABLE 1-continued

| MATERIAL | EXAMPLES OF MATERIAL | PUBLICATIONS |
| --- | --- | --- |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2009062578 |

Green hosts

| | | |
| --- | --- | --- |
| Arylcarbazoles | | Appl. Phys. Lett. 78, 1622 (2001) |
| | | US20030175553 |
| | | WO2001039234 |

TABLE 1-continued

| MATERIAL | EXAMPLES OF MATERIAL | PUBLICATIONS |
| --- | --- | --- |
| Aryltriphenylene compounds | | US20060280965 |
| | | US20060280965 |
| | | WO2009021126 |
| Donor acceptor type molecules | | WO2008056746 |

TABLE 1-continued
| MATERIAL | EXAMPLES OF MATERIAL | PUBLICATIONS |
|---|---|---|
| Aza-carbazole/DBT/DBF | 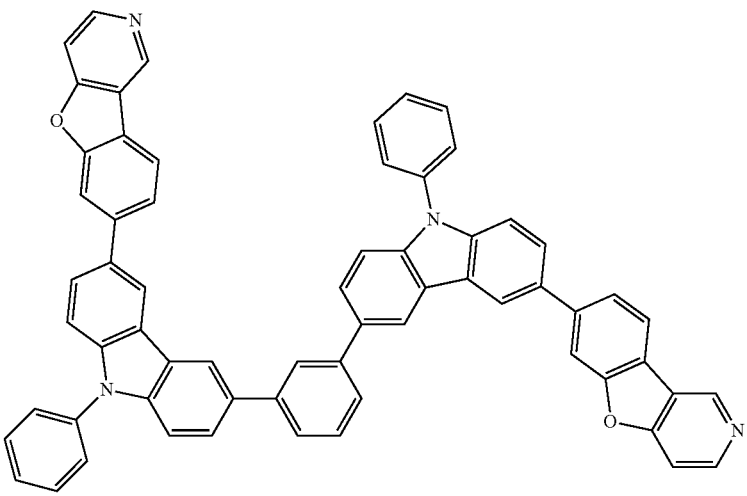 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| Polymers (e.g., PVK) | 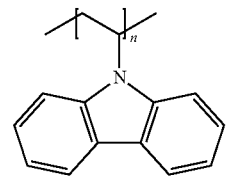 | Appl. Phys. Lett. 77, 2280 (2000) |
| Spirofluorene compounds | 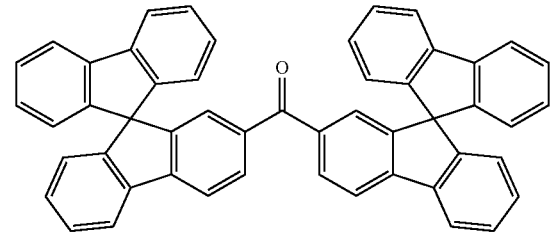 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 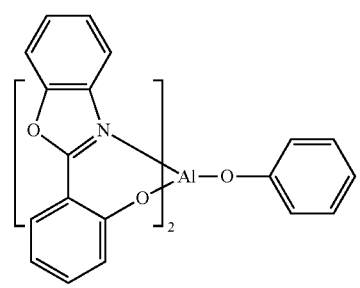 | WO2005089025 |
| | 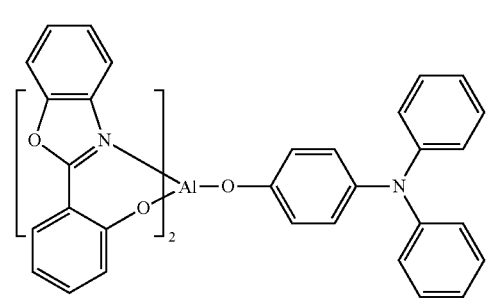 | WO2006132173 |

TABLE 1-continued

| MATERIAL | EXAMPLES OF MATERIAL | PUBLICATIONS |
| --- | --- | --- |
|  |  | JP200511610 |
| Spirofluorene-carbazole compounds |  | JP2007254297 |
|  |  | JP2007254297 |
| Indolocabazoles |  | WO2007063796 |
|  |  | WO2007063754 |

TABLE 1-continued

| MATERIAL | EXAMPLES OF MATERIAL | PUBLICATIONS |
| --- | --- | --- |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |
| Metal phenoxypyridine compounds | | WO2005030900 |
| Metal coordination complexes (e.g., Zn, Al With N^N ligands) | | US20040137268, US20040137267 |

TABLE 1-continued
| MATERIAL | EXAMPLES OF MATERIAL | PUBLICATIONS |
|---|---|---|
| Blue hosts | | |
| Arylcarbazoles | 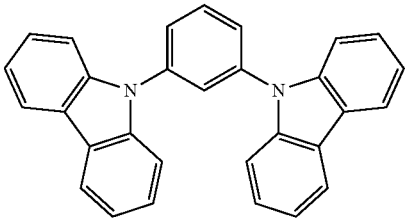 [SMILES: c1cc(-n2c3ccccc3c3ccccc32)cc(-n2c3ccccc3c3ccccc32)c1] | Appl. Phys. Lett, 82, 2422 (2003) |
| | 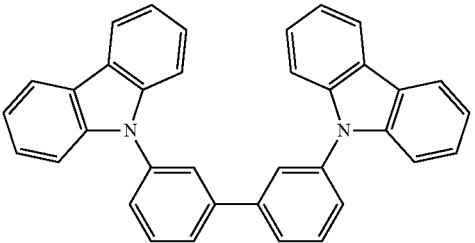 [SMILES: c1cc(-c2cccc(-n3c4ccccc4c4ccccc43)c2)cc(-n2c3ccccc3c3ccccc32)c1] | US20070190359 |
| Dibenzothiophene/Dibenzofuran-carbazole compounds | 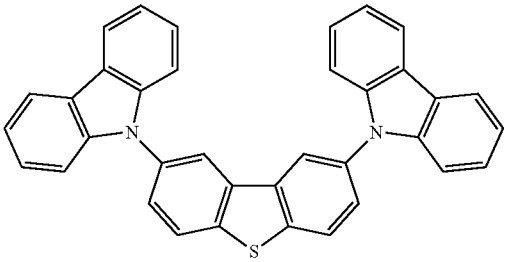 [SMILES: c1ccc2c(c1)c1ccccc1n2-c1ccc2sc3ccc(-n4c5ccccc5c5ccccc54)cc3c2c1] | WO2006114966, US20090167162 |
| | 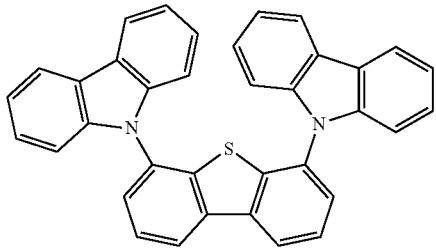 [SMILES: c1cc(-n2c3ccccc3c3ccccc32)c2sc3c(-n4c5ccccc5c5ccccc54)cccc3c2c1] | US20090167162 |
| | 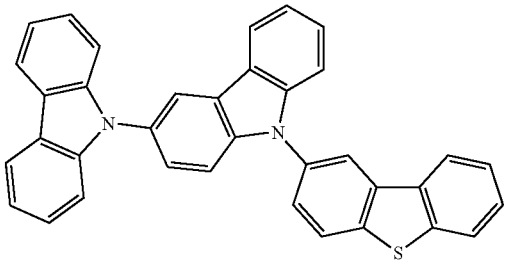 [SMILES: c1ccc2c(c1)sc1ccc(-n3c4ccccc4c4cc(-n5c6ccccc6c6ccccc65)ccc43)cc12] | WO2009086028 |
| | 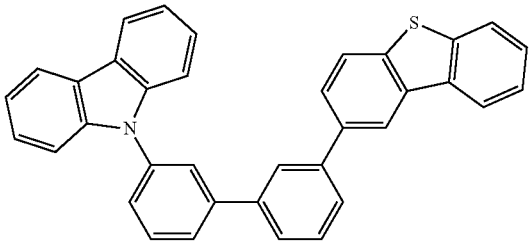 [SMILES: c1cc(-c2cccc(-n3c4ccccc4c4ccccc43)c2)cc(-c2ccc3sc4ccccc4c3c2)c1] | US20090030202, US20090017330 |

TABLE 1-continued
| MATERIAL | EXAMPLES OF MATERIAL | PUBLICATIONS |
|---|---|---|
| Silicon aryl compounds | 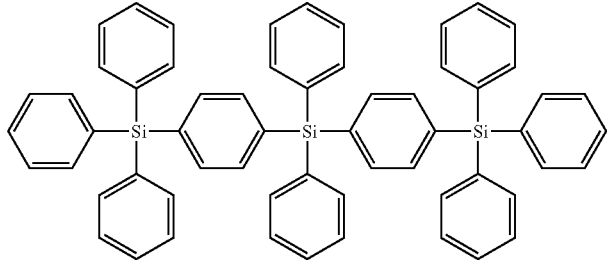 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 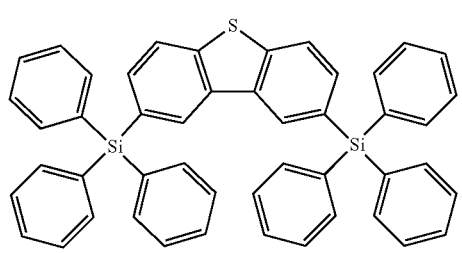 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 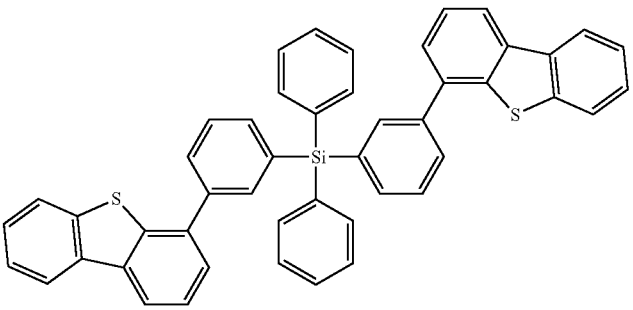 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 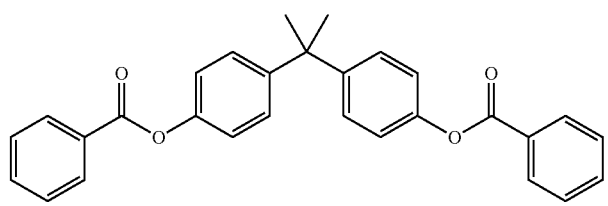 [SMILES: CC(C)(c1ccc(OC(=O)c2ccccc2)cc1)c1ccc(OC(=O)c2ccccc2)cc1] | WO2006100298 |
| High triplet metal organometallic complex | 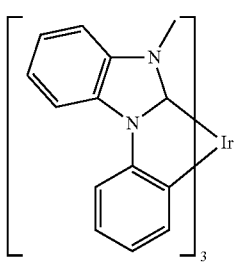 | U.S. Pat. No. 7,154,114 |

TABLE 1-continued

| MATERIAL | EXAMPLES OF MATERIAL | PUBLICATIONS |
| --- | --- | --- |
| | Phosphorescent dopants | |
| | Red dopants | |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |
| | | US20060202194 |

TABLE 1-continued

| MATERIAL | EXAMPLES OF MATERIAL | PUBLICATIONS |
|---|---|---|
| | | US20060202194 |
| | | US20070087321 |
| | | US20070087321 |
| | | Adv. Mater. 19, 739 (2007) |
| | | WO2009100991 |

TABLE 1-continued
| MATERIAL | EXAMPLES OF MATERIAL | PUBLICATIONS |
|---|---|---|
| | 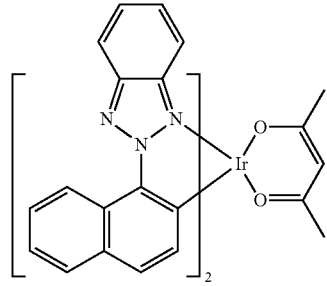 | WO2008101842 |
| Platinum(II) organometallic complexes | 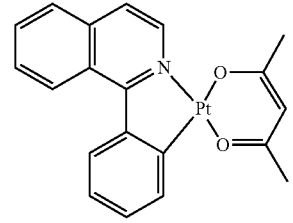 | WO2003040257 |
| Osminum(III) complexes | 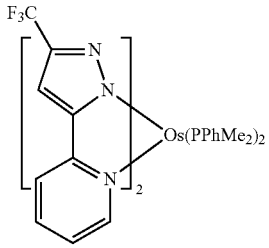 | Chem. Mater. 17, 3532 (2005) |
| Ruthenium(II) complexes | 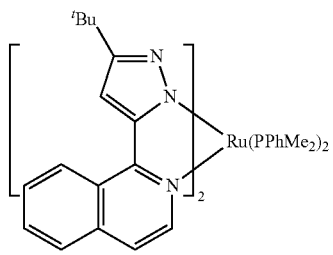 | Adv. Mater. 17, 1059 (2005) |
| Rhenium (I), (II), and (III) complexes | 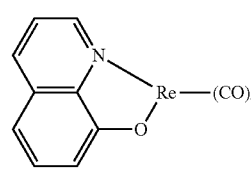 | US20050244673 |

TABLE 1-continued
| MATERIAL | EXAMPLES OF MATERIAL | PUBLICATIONS |
| --- | --- | --- |
| | Green dopants | |
| Iridium(III) organometallic complexes | 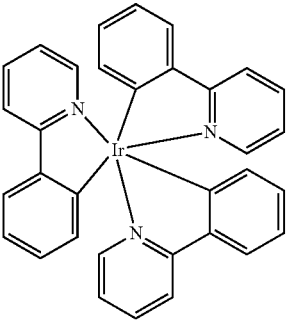<br>and its derivative | Inorg. Chem. 40, 1704 (2001) |
| | 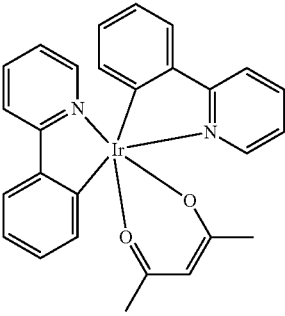 | US20020034656 |
| | 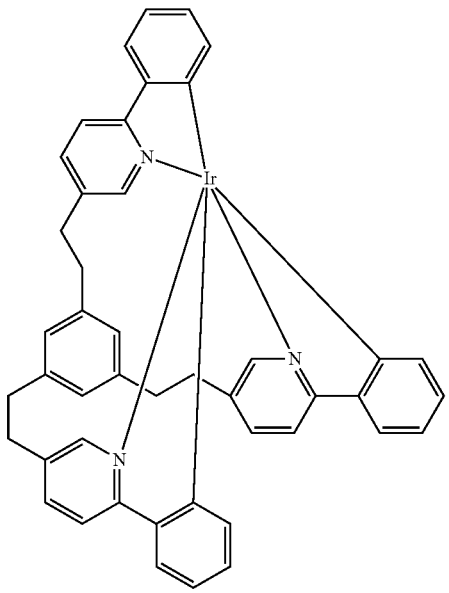 | U.S. Pat. No. 7,332,232 |

TABLE 1-continued

| MATERIAL | EXAMPLES OF MATERIAL | PUBLICATIONS |
|---|---|---|
| | | US20090108737 |
| | | US20090039776 |
| | | U.S. Pat. No. 6,921,915 |
| | | U.S. Pat. No. 6,687,266 |
| | | Chem. Mater. 16, 2480 (2004) |

TABLE 1-continued

| MATERIAL | EXAMPLES OF MATERIAL | PUBLICATIONS |
|---|---|---|
| | | US20070190359 |
| | | US 20060008670<br>JP2007123392 |
| | | Adv. Mater. 16, 2003 (2004) |
| | | Angew. Chem. Int. Ed. 2006, 45, 7800 |
| | | WO2009050290 |
| | | US20090165846 |

TABLE 1-continued
| MATERIAL | EXAMPLES OF MATERIAL | PUBLICATIONS |
|---|---|---|
| | 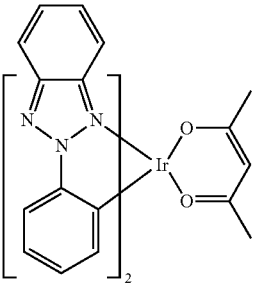 | US20080015355 |
| Monomer for polymeric metal organometallic compounds | 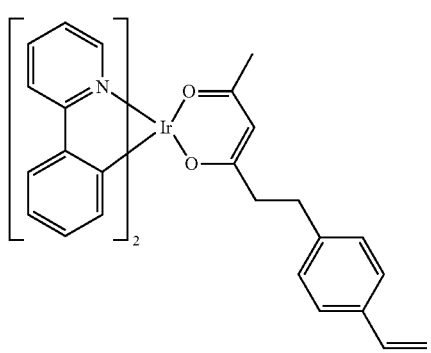 | U.S. Pat. No. 7,250,226, U.S. Pat. No. 7,396,598 |
| Pt(II) organometallic complexes, including polydentated ligands | 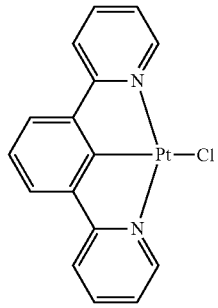 | Appl. Phys. Lett. 86, 153505 (2005) |
| | 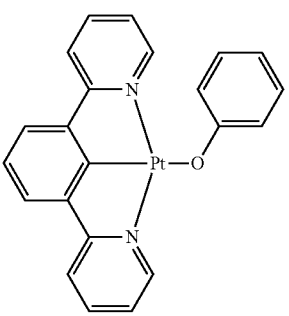 | Appl. Phys. Lett. 86, 153505 (2005) |

TABLE 1-continued

| MATERIAL | EXAMPLES OF MATERIAL | PUBLICATIONS |
|---|---|---|
| | | Chem. Lett. 34, 592 (2005) |
| | | WO2002015645 |
| | | US20060263635 |
| Cu complexes | | WO2009000673 |
| Gold complexes | | Chem. Commun. 2906 (2005) |

TABLE 1-continued
| MATERIAL | EXAMPLES OF MATERIAL | PUBLICATIONS |
|---|---|---|
| Rhenium(III) complexes | 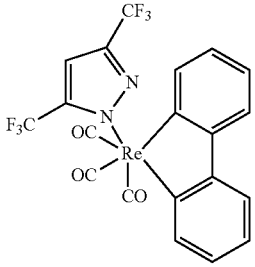 | Inorg. Chem. 42, 1248 (2003) |
| Deuterated organometallic complexes | 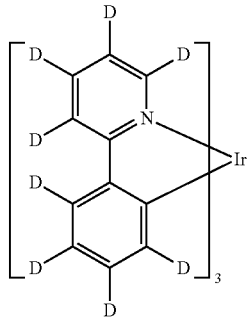 | US20030138657 |
| Organometallic complexes with two or more metal centers | 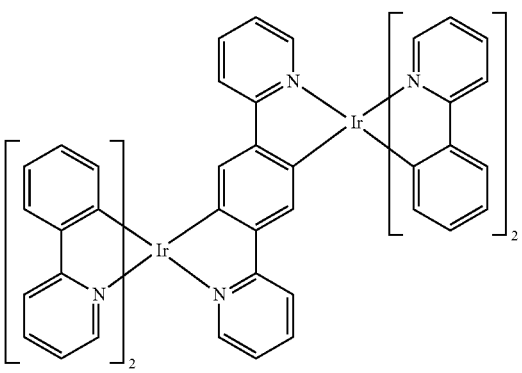 | US20030152802 |
|  | 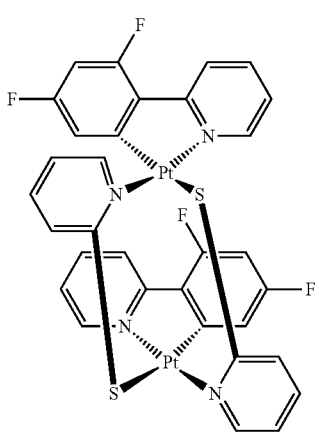 | U.S. Pat. No. 7,090,928 |

TABLE 1-continued

| MATERIAL | EXAMPLES OF MATERIAL | PUBLICATIONS |
| --- | --- | --- |
| Blue dopants | | |
| Iridium(III) organometallic complexes | | WO2002002714 |
| | | WO2006009024 |
| | | US20060251923 |
| | | U.S. Pat. No. 7,393,599, WO2006056418, US20050260441, WO2005019373 |
| | | U.S. Pat. No. 7,534,505 |
| | | U.S. Pat. No. 7,445,855 |

TABLE 1-continued

| MATERIAL | EXAMPLES OF MATERIAL | PUBLICATIONS |
|---|---|---|
| | | US20070190359, US20080297033 |
| | | U.S. Pat. No. 7,338,722 |
| | | US20020134984 |
| | | Angew. Chem. Int. Ed. 47, 1 (2008) |
| | | Chem. Mater. 18, 5119 (2006) |

TABLE 1-continued

| MATERIAL | EXAMPLES OF MATERIAL | PUBLICATIONS |
|---|---|---|
| | | Inorg. Chem. 46, 4308 (2007) |
| | | WO2005123873 |
| | | WO2005123873 |
| | | WO2007004380 |
| | | WO2006082742 |

TABLE 1-continued
| MATERIAL | EXAMPLES OF MATERIAL | PUBLICATIONS |
|---|---|---|
| Osmium(II) complexes | 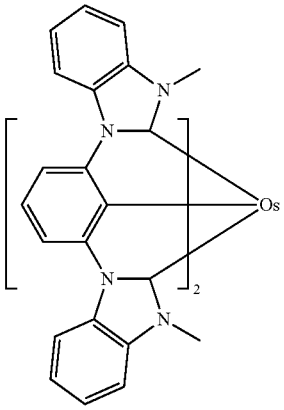 | U.S. Pat. No. 7,279,704 |
| | 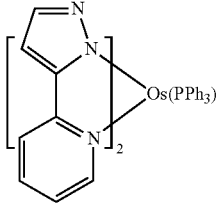 | Organometallics 23, 3745 (2004) |
| Gold complexes | 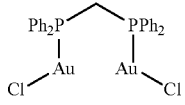 | Appl. Phys. Lett. 74, 1361 (1999) |
| Platinum(II) complexes | 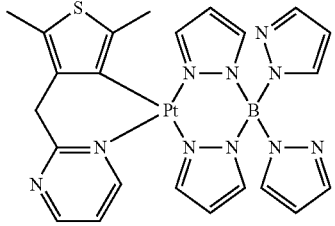 | WO2006098120, WO2006103874 |
| Exciton/hole blocking layer materials | | |
| Bathocuprine compounds (e.g., BCP, BPhen) | 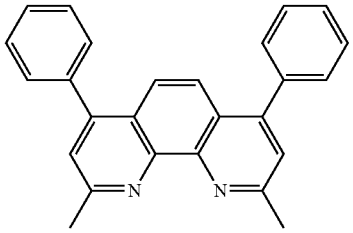 [SMILES: Cc1cc(-c2ccccc2)c2ccc3c(-c4ccccc4)cc(C)nc3c2n1] | Appl. Phys. Lett. 75, 4 (1999) |
| | 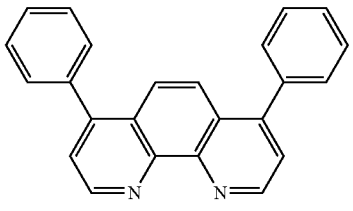 [SMILES: c1ccc(-c2ccnc3c2ccc2c(-c4ccccc4)ccnc23)cc1] | Appl. Phys. Lett. 79, 449 (2001) |

TABLE 1-continued

| MATERIAL | EXAMPLES OF MATERIAL | PUBLICATIONS |
|---|---|---|
| Metal 8-hydroxyquinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |
| Triphenylene compounds | | US20050025993 |

TABLE 1-continued
| MATERIAL | EXAMPLES OF MATERIAL | PUBLICATIONS |
|---|---|---|
| Fluorinated aromatic compounds | 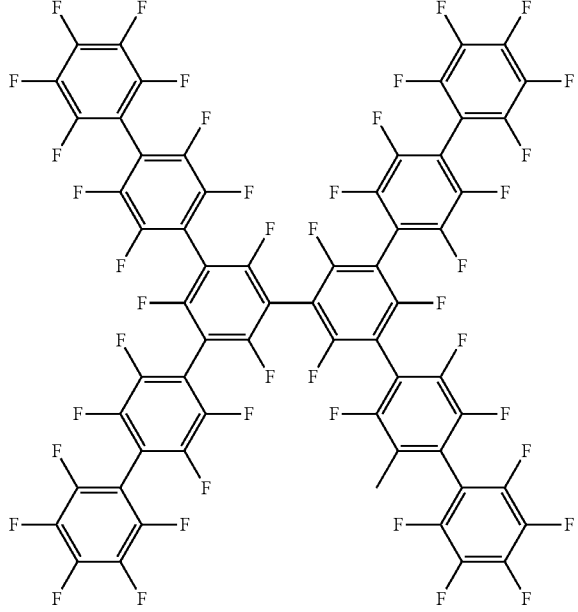 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 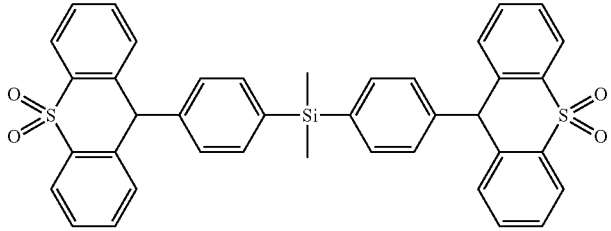 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Electron transporting materials | | |
| Anthracene-benzoimidazole compounds | 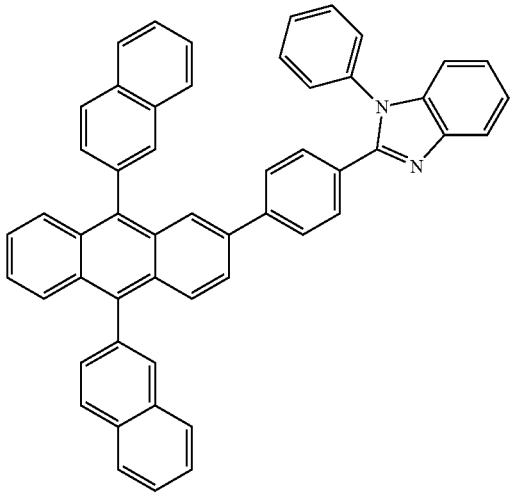 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |

TABLE 1-continued

| MATERIAL | EXAMPLES OF MATERIAL | PUBLICATIONS |
|---|---|---|
| | | US20090179554 |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987)<br>U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |

TABLE 1-continued
| MATERIAL | EXAMPLES OF MATERIAL | PUBLICATIONS |
|---|---|---|
| | 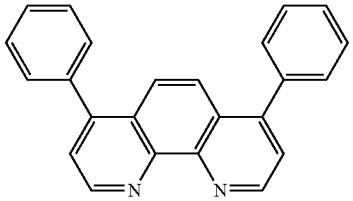 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g., triazole, oxadiazole, imidazole, benzoimidazole) | 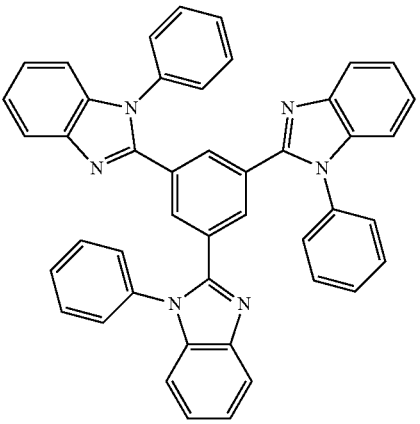 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 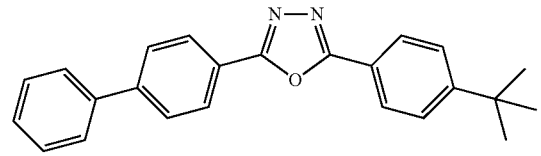 [SMILES: CC(C)(C)c1ccc(-c2nnc(-c3ccc(-c4ccccc4)cc3)o2)cc1] | Appl. Phys. Lett. 55, 1489 (1989) |
| | 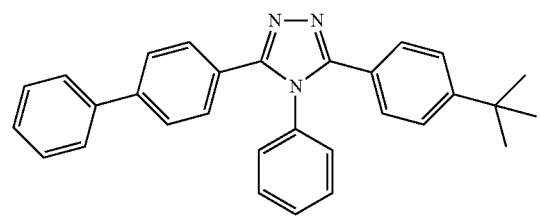 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 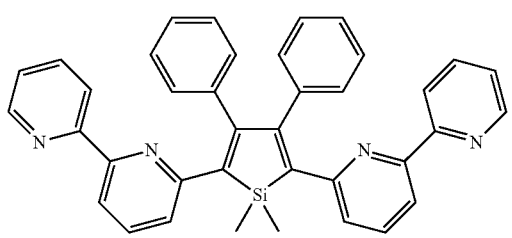 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 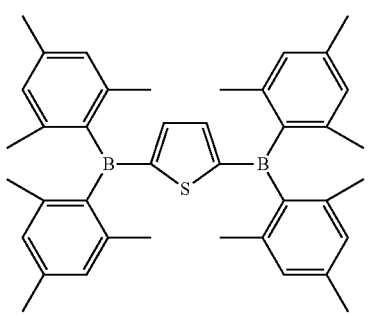 | J. Am. Chem. Soc. 120, 9714 (1998) |

TABLE 1-continued

| MATERIAL | EXAMPLES OF MATERIAL | PUBLICATIONS |
|---|---|---|
| Fluorinated aromatic compounds | | J. Am. Chem. Soc. 122, 1832 (2000) |
| Fullerene (e.g., C60) | | US20090101870 |
| Triazine complexes | | US20040036077 |
| Zn (N^N) complexes | | U.S. Pat. No. 6,528,187 |

EXPERIMENTAL

Compound Examples

Example 1

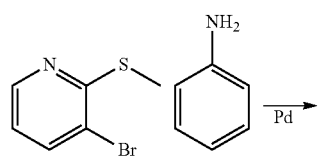

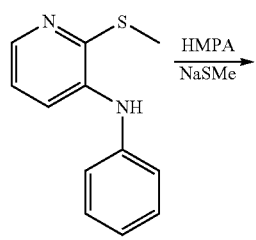

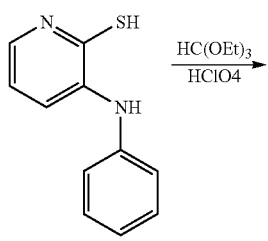

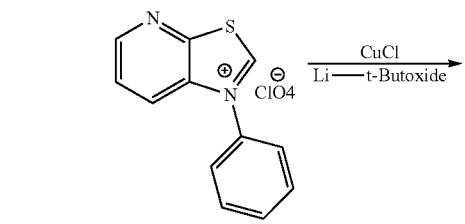

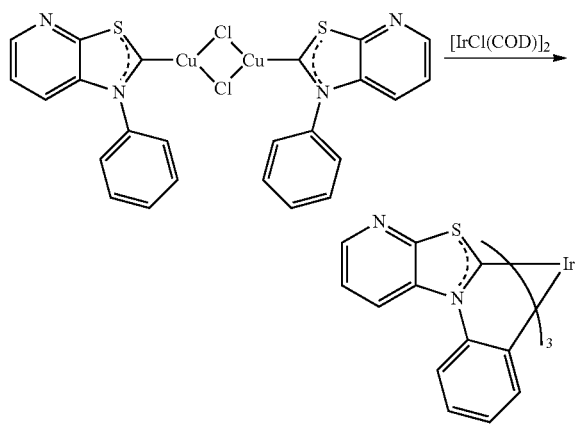

Synthesis of 2-(methylthio)-N-Phenylpyridine-3-amino

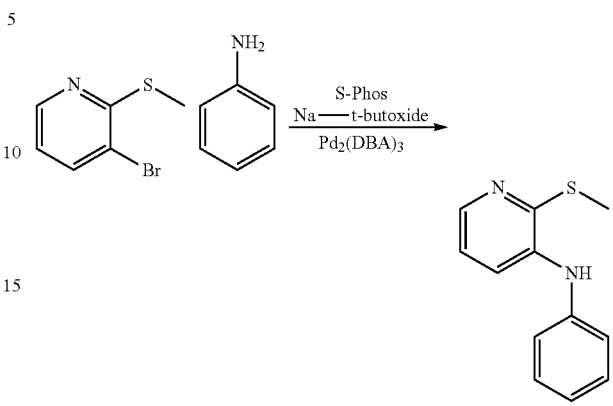

3-bromo-2(methylthio)pyridine (25 g, 123 mmol), Pd$_2$dba$_3$ (6.75 g, 7.38 mmol), S-Phos (6.06 g, 14.77 mmol) and sodium butan-1-olate (17.74 g, 185 mmol) are placed in dry 3-neck flask under N$_2$. The reaction mixture is vacuumed and charged with N$_2$ a total of three times. Aniline (22.93 g, 246 mmol) and 500 mL toluene are added to the reaction mixture. The reaction mixture is refluxed for 18 h. The crude reaction mixture is run through silica gel plug and eluted with toluene. The toluene portion is concentrated down and subjected to silica gel column using 3-5% DCM in Hexane to yield the desired product.

Synthesis of 3-(phenylamino)pyridine-2-thiol

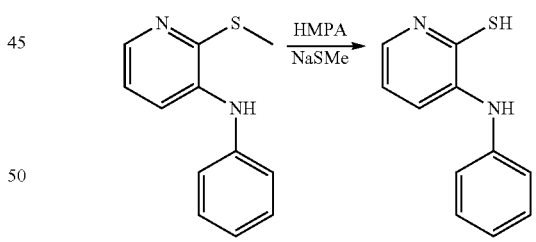

A 250 mL round bottom flask is charged with sodium methanethiolate (5.18 g, 73.8 mmol), 2-(methylthio)-N-Phenylpyridine-3-amino (13.25 g, 61.5 mmol) and Hexamethyl phosphoramide (HMPA) (100 mL). The reaction mixture is heated up to 100° C. for 7 h. The reaction is cooled to room temperature, and 100 mL of 1N HCl is added. The reaction mixture is extracted with 3×100 mL ethyl acetate. The organic portion is washed with 3×50 mL Brien, and then dried over sodium sulfate and evaporated to yield the desired compound.

Synthesis of Benzothioazole Carbene Ligand Precursor

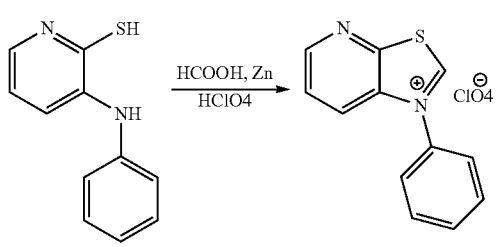

A 250 mL round bottom flask was charged with zinc dust (2.339 g, 35.8 mmol), 3-(phenylamino)pyridine-2-thiol (12 g, 59.6 mmol) and Formic Acid (100 mL). The reaction mixture is refluxed under $N_2$ for 6 h. The reaction mixture is filtered off to get rid of insoluble material. Hypochloric acid (35.9 mL, 59.9 mmol) is added to the filtrate and stirred for 20 minutes. 200 mL of water is added and the precipitation is collected. The precipitation is washed with $H_2O$ and Ether to yield the desired product.

Synthesis of Dichloro Copper Dimer

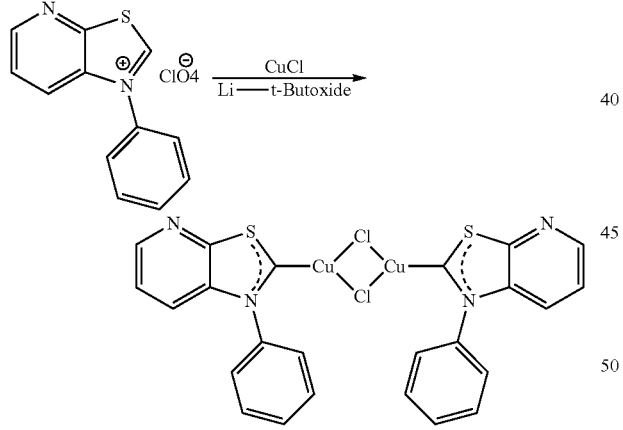

A 500 mL round bottom flask is charged with CuCl (3.9 g, 39.4 mmol), Lithium tert-butoxide (3.15 g, 39.4 mmol) and anhydrous. THF (400 mL). The reaction mixture is stirred inside the glove box overnight. Perchloride salt (2.31 g, 7.41 mmol) is added into the reaction mixture and stirred overnight. The reaction mixture is removed from glove box and filtered. The filtrate is concentrated to dryness, and re-suspended in dichloromethane. The suspension is filtered, and the filtrate is concentrated to dryness to yield the desired compound.

Synthesis of Benzothioazole Iridium Tris Complex

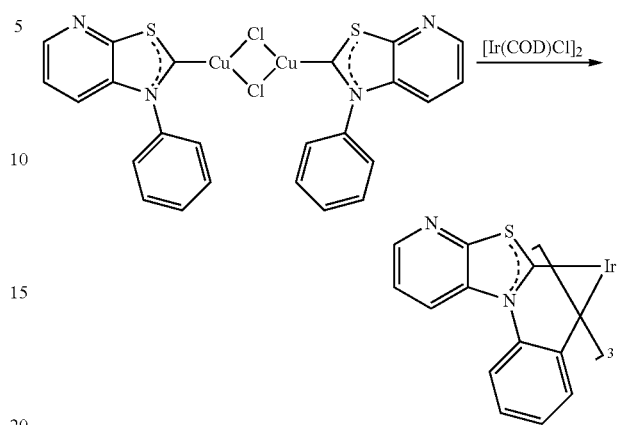

A 500 mL round bottom flask is charged with copper dichloride bridge dimer (1.68 g, 2.71 mmol), Iridium COD dimer (0.568 g, 0.846 mmol) and chlorobenzene (300 mL) to give an orange suspension. The reaction mixture is vacuumed and back filled with $N_2$ a total of three times. Then, the reaction mixture is heated to reflux overnight. The reaction mixture is filtered, and the filtrate is concentrated to dryness. The residue is subjected to column chromatography ($SiO_2$, 100% DCM) to yield the desired compound.

Example 2

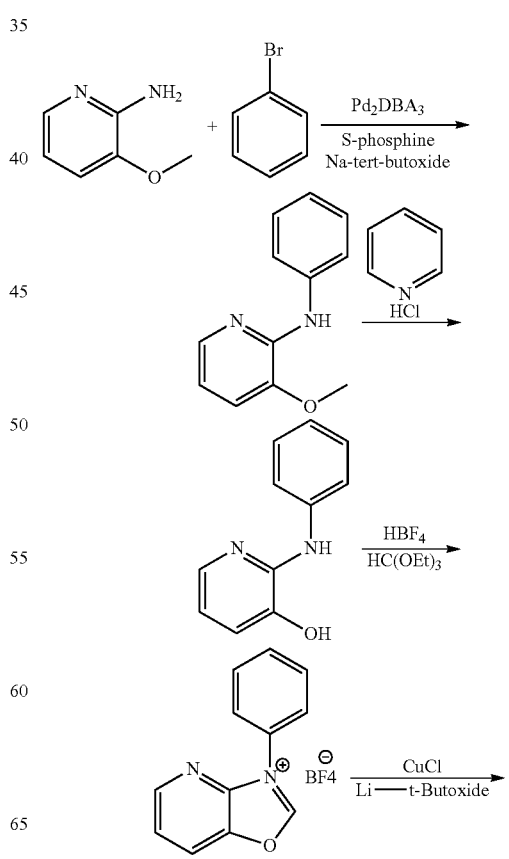

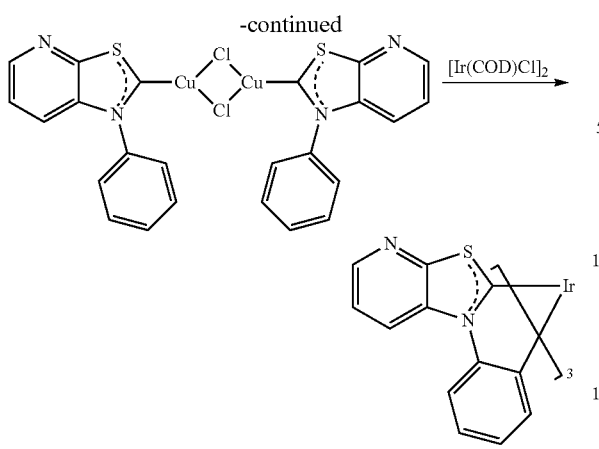

Synthesis of 3-methoxy-N-phenylpyridine-gamine

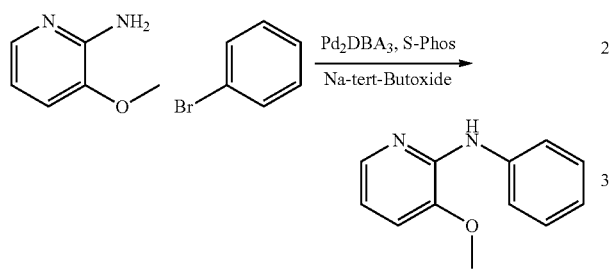

A 1 L 3-neck flask is charged with 3-methoxypyridine-2-amine (17.65 g, 143 mmol), bromobenzene (15 g, 96 mmol), Pd₂DBA₃ (1.75 g, 1.91 mmol), Sodium tert-butoxide (18.36 g, 101 mmol), S-Phos (1.56 g, 3.82 mmole) and 400 mL of xylene. The reaction mixture is refluxed for 4 h. The product is isolated by column chromatography (5% EtoAc in Hexs) to yield the desired product.

Synthesis of 2-(phenylamino)pyridine-3-ol

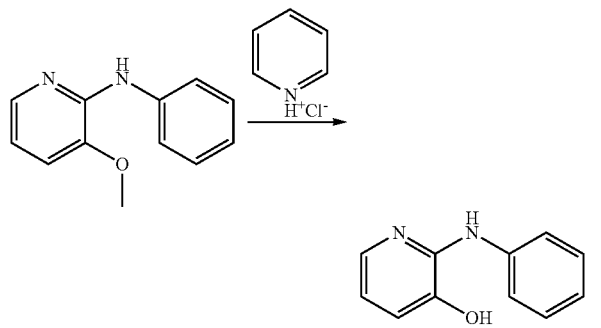

1 L 3-neck flask is charged with Pyridinium chloride (52.2 g, 452 mmol) and 3-methoxy-N-phenylpyridine-2-amine (9 g, 45.2 mmol). The reaction mixture is heated to 200° C. for 4 h. The reaction mixture is dumped into 5% HCl (200 mL), and extracted with 3×300 mL ETOAC. The organic portion is combined and purified by column chromatography (100% DCM) to yield the desired product.

Synthesis of Benzooxoazok Carbene Ligand Precursor

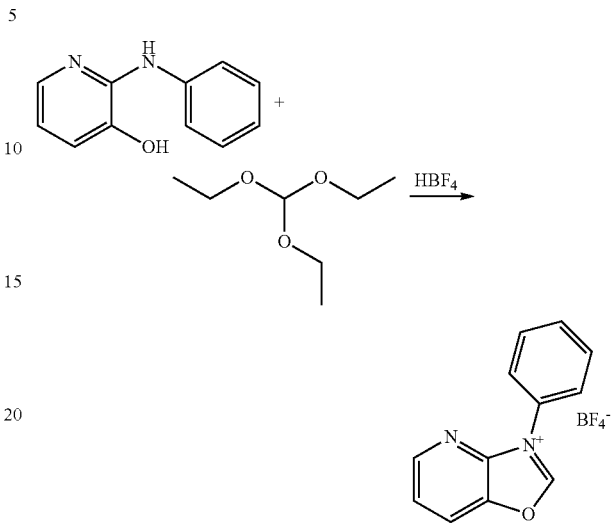

Hydrogen tetrafluoroborate (6.79 mL, 48% w/w) is added drop-wise to a solution of 2-(phenylamino)pyridine-3-ol (9 g, 48.6 mmol) in 30 mL Methanol. After 30 minutes of stirring, the solvent is removed under vacuum and 30 mL (EtO)₃CH is added. The resulting solution is stirred at room temperature under N₂ overnight to give a white suspension. The solid is filtered, and then washed with diethyl ether to give the product.

Synthesis of Benzooxazole Iridium Tris Complex

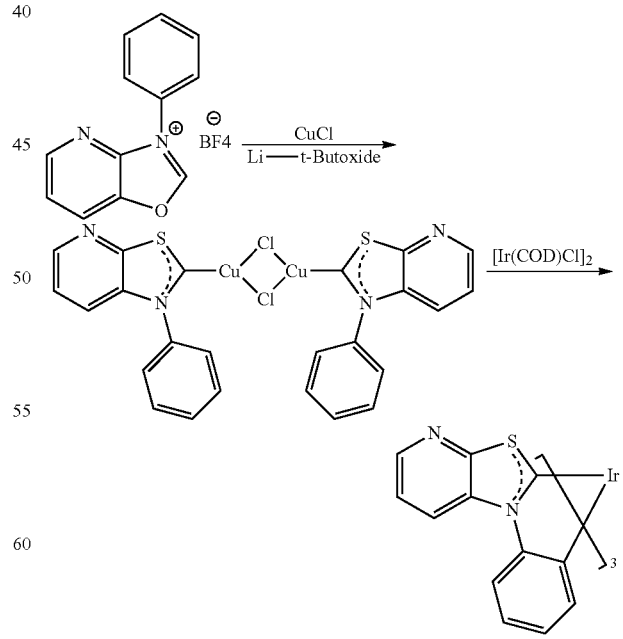

For synthesis of benzooxazole iridium tris complex, please refer to the benzothioazole example.

Example 3

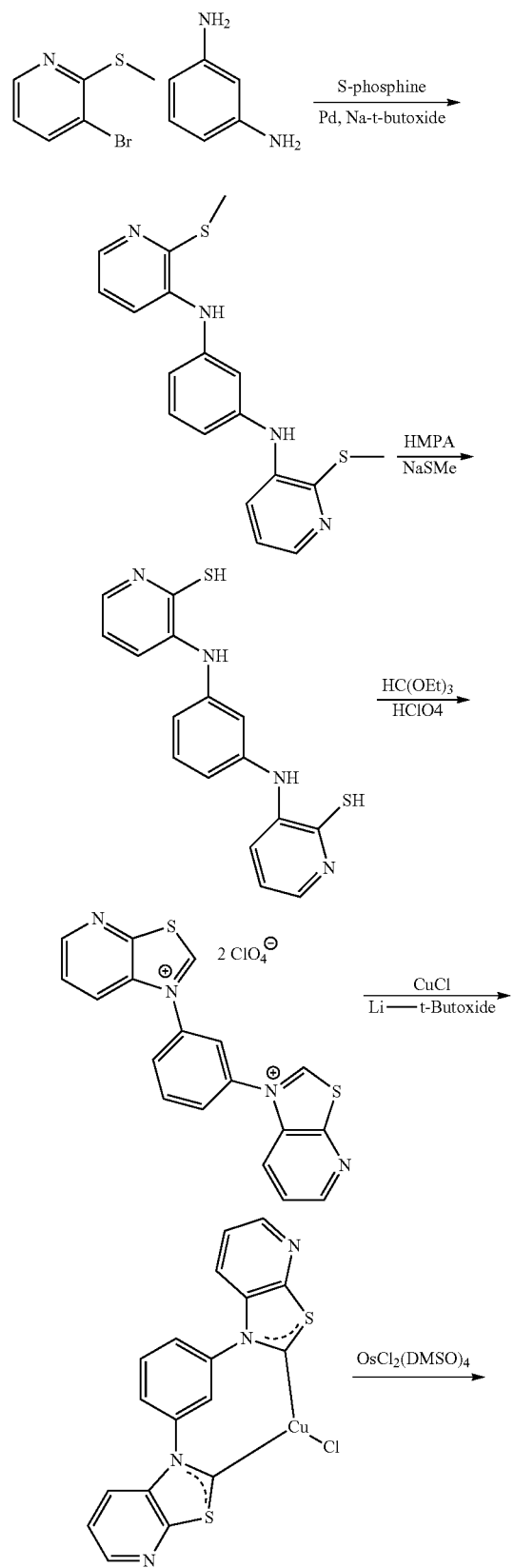

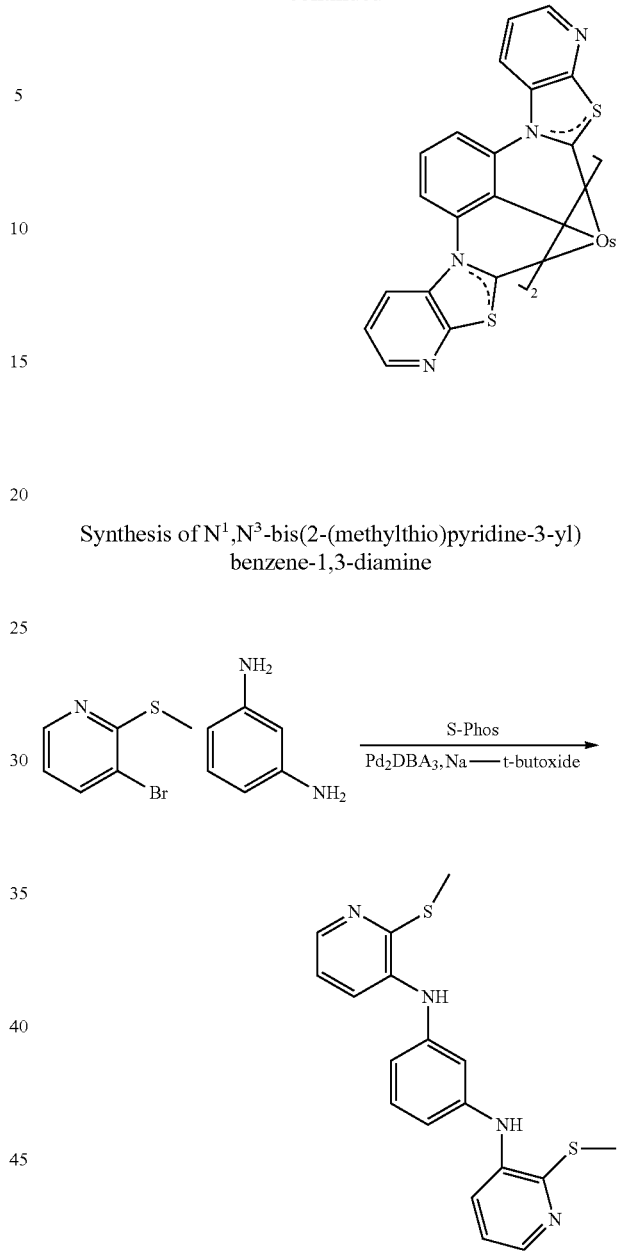

Synthesis of N¹,N³-bis(2-(methylthio)pyridine-3-yl)benzene-1,3-diamine 3-bromo-2(methylthio)pyridine (25 g, 123 mmol), $Pd_2dba_3$ (6.75 g, 7.38 mmol), S-Phos (6.06 g, 14.77 mmole) and sodium butan-1-plate (17.74 g, 185 mmol) are placed in dry 3-neck flask under $N_2$. The reaction mixture is vacuumed, and charged with $N_2$ for a total of three times. 1,3-diaminobenzene (6.64 g, 61.5 mmol) and 500 mL toluene are added to the reaction mixture. The reaction mixture is refluxed for 18 h. The crude reaction mixture is run through a silica gel plug and eluted with toluene. The toluene portion is concentrated down and subjected to a silica gel column using 3-5% DCM in Hexane to yield the desired product.

Synthesis of 3,3'-(1,3-phenylenebis(azanediyl))bis(pyridine-2-thiol)

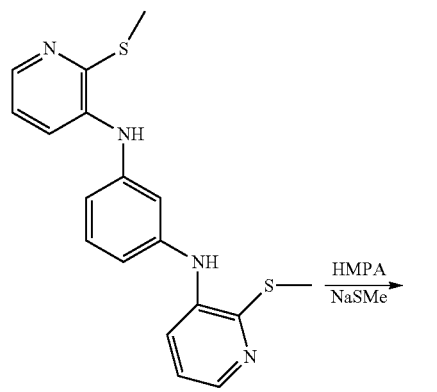

A 250 mL round bottom flask is charged with sodium methanethiolate (5.18 g, 73.8 mmol), $N^1,N^3$-bis(2-(methylthio)pyridine-3-yl)benzene-1,3-diamine (13.25 g, 61.5 mmol) and Hexamethyl phosphoramide(HMPA) (100 mL). The reaction mixture is heated up to 100° C. for 7 h. The reaction is cooled to room temperature, and 100 mL of 1N HCl is added. The reaction mixture is extracted with 3×100 mL ethyl acetate. The organic portion is washed with 3×50 mL Brien, dried over sodium sulfate and evaporated to yield the desired compound.

Synthesis of 1,1'-(1,3-phenylene)bis(thiazolo[5,4-b]pyridine-1-ium) Perchlorate salt

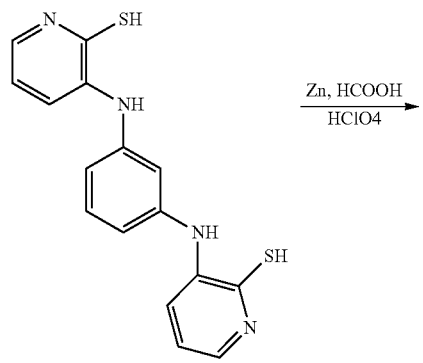

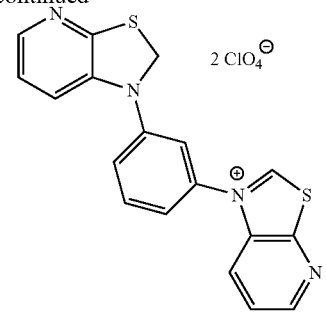

A 250 mL round bottom flask is charged with zinc dust (2.339 g, 35.8 mmol), 3,3'-(1,3-phenylenebis(azanediyl))bis(pyridine-2-thiol) and Formic Acid (100 mL). The reaction mixture is refluxed under $N_2$ for 6 h. The reaction mixture is filtered off to get rid of insoluble material. Hypochloric acid (35.9 mL, 59.9 mmol) is added to the filtrate and stirred for 20 minutes. 200 mL of water is added and the precipitation is collected. The precipitation is washed with $H_2O$ and Ether to yield the desired product.

Synthesis of Copper Carbene Complex

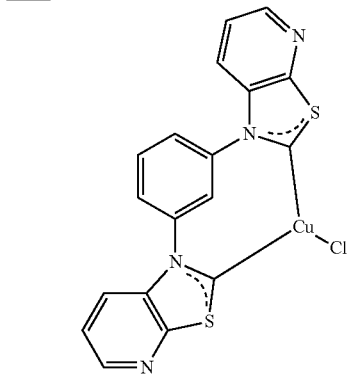

A 500 mL round bottom flask is charged with CuCl (3.9 g, 39.4 mmol), Lithium tert-butoxide (3.15 g, 39.4 mmol) and anhydrous THF (400 mL). The reaction mixture is stirred inside the glove box overnight. The perchloride salt (4.05 g, 7.41 mmol) is added into the reaction mixture and stirred overnight. The reaction mixture is removed from the glove box, and filtered. The filtrate is concentrated to dryness and re-suspended in dichloromethane. The suspension is filtered and filtrate is concentrated to dryness to yield the desired compound.

Synthesis of Osmium Carbene Complex

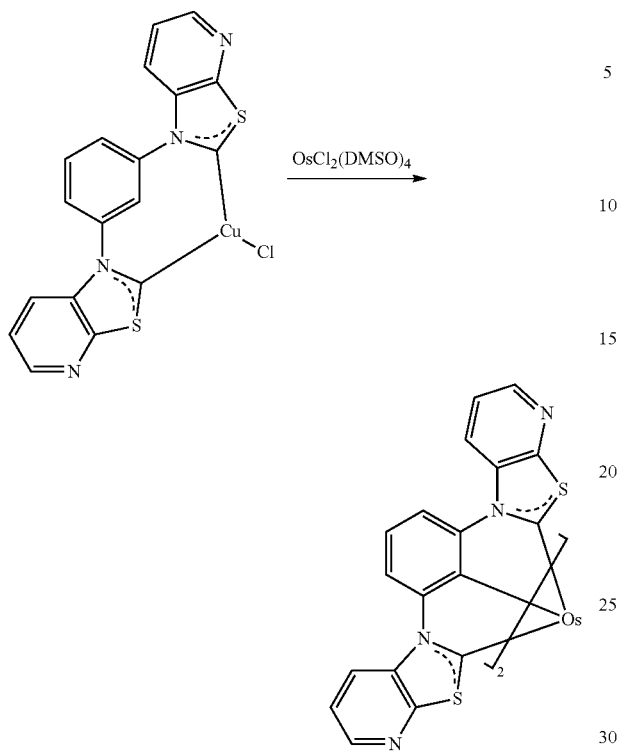

A 250 mL round-bottomed flask is charged with OsCl$_2$(DMSO)$_4$ (250 mg, 0.436 mmol), copper carbene complex (584 mg, 1.3 mmol) in 2-ethoxyethanol (125 mL) to give a tan suspension. The reaction mixture is vacuumed and back filled with N$_2$; then the reaction mixture is heated to reflux for 1 h. The reaction mixture is filtered though celite, and the filtrate is subject to column chromatography (SiO$_2$, Et$_3$N pretreated, 60% EtOAC in hexanes) to yield the desired compound.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound comprising a ligand having the structure:

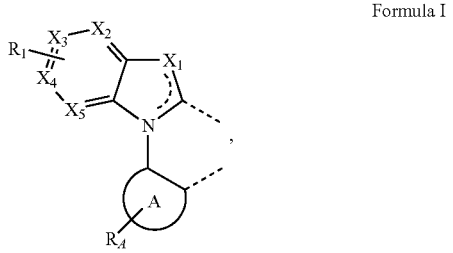

Formula I wherein $X_1$ is S or O;
wherein $X_2$, $X_3$, $X_4$, and $X_5$ are independently C or N;
wherein at least one of $X_2$, $X_3$, $X_4$, and $X_5$ is N;
wherein $R_1$ may represent mono, di, or tri substitutions;
wherein each $R_1$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein two adjacent substituents of $R_1$ are optionally joined to form a fused ring;
wherein $R_A$ may represent mono, di, tri, or tetra substitutions;
wherein each $R_A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein two adjacent substituents of $R_A$ are optionally joined to form a fused ring;
wherein A is a 6-membered carbocyclic or heterocyclic ring;
wherein the ligand L is coordinated to Os;
wherein the compound is homoleptic; and
wherein one $R_A$ is also coordinated to Os and ligand L is a tridentate ligand.

2. The compound of claim 1, wherein A is benzene.

3. The compound of claim 1, wherein the ligand L has the formula:

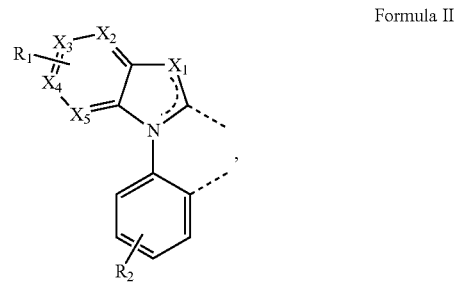

Formula II wherein at least one of $X_2$, $X_3$, $X_4$, and $X_5$ is N;
wherein $R_2$ has the same meaning as $R_A$ in Formula I.

4. The compound of claim 1, wherein the ligand L has the formula:

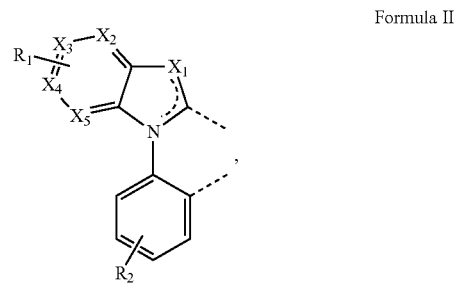

Formula II wherein at least two of $X_2$, $X_3$, $X_4$, and $X_5$ are N;
wherein $R_2$ has the same meaning as $R_A$ in Formula I.

5. The compound of claim 1, wherein the compound is selected from the group consisting of:

Compound 8G
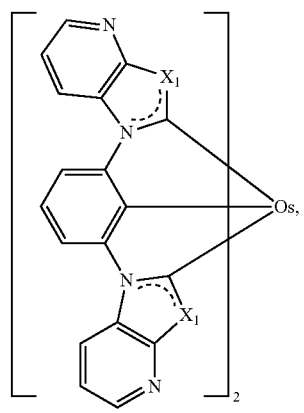
Compound 9G
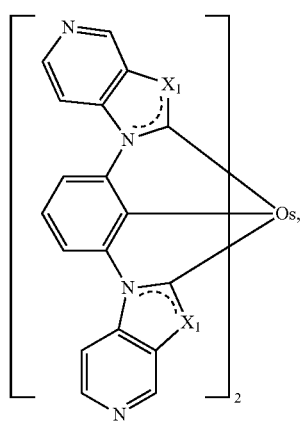
Compound 10G
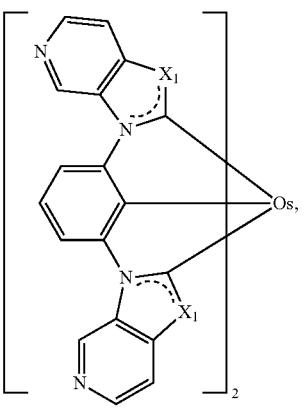
Compound 11G
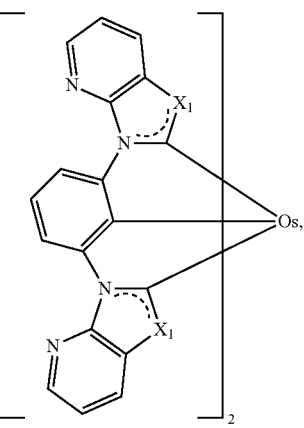
Compound 12G
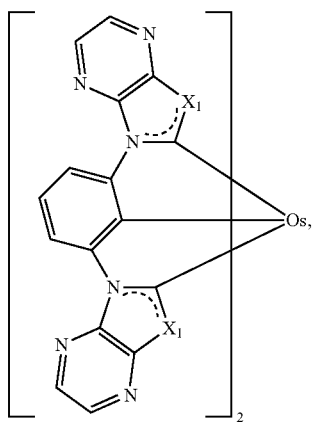
Compound 13G
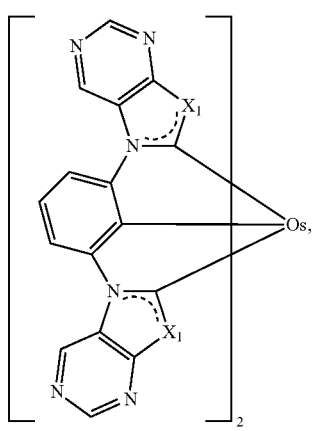
Compound 14G
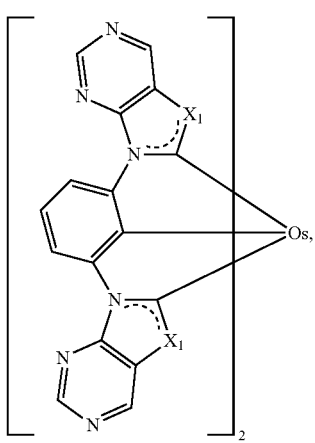

-continued
Compound 15G
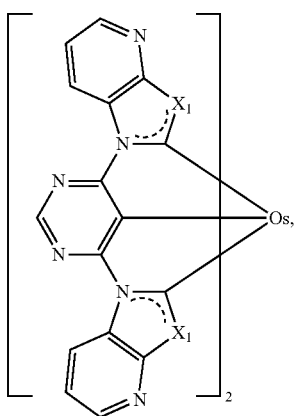
Compound 16G
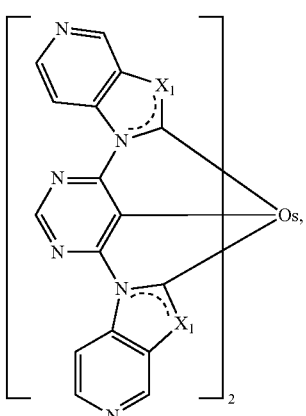
Compound 17G
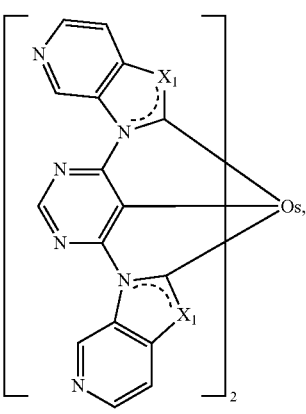
Compound 18G
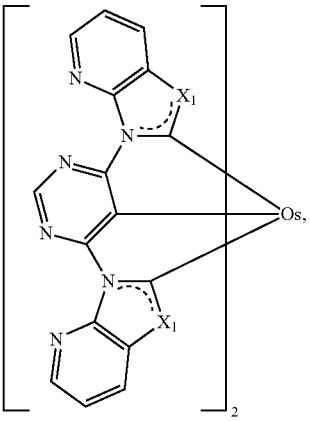
-continued
Compound 19G
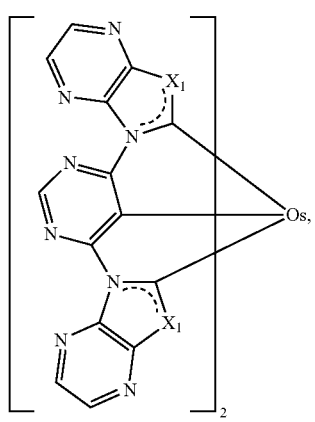
Compound 20G
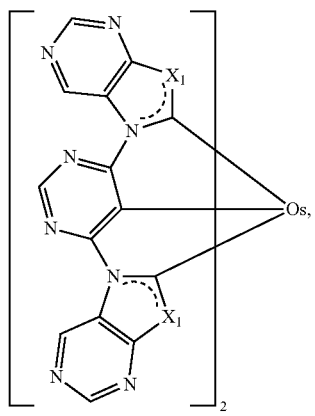
Compound 21G
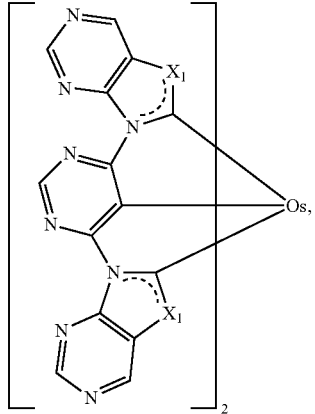

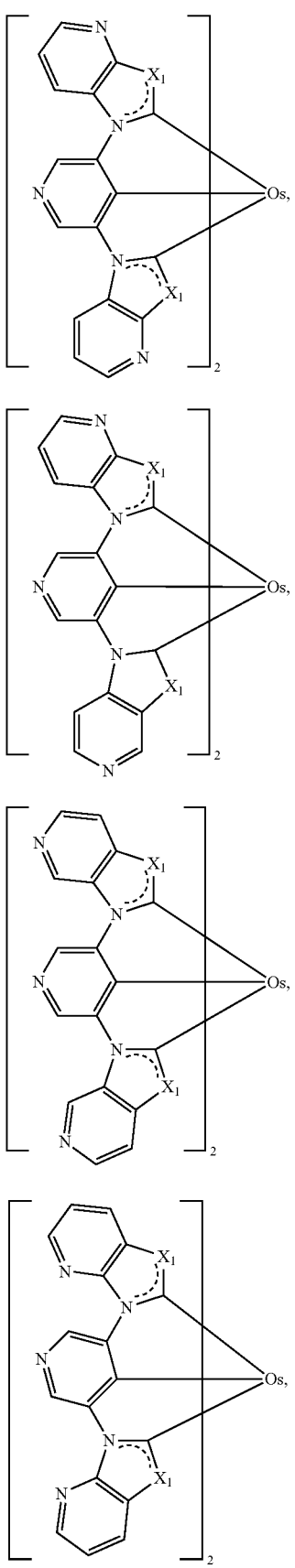
Compound 22G
Compound 23G
Compound 24G
Compound 25G
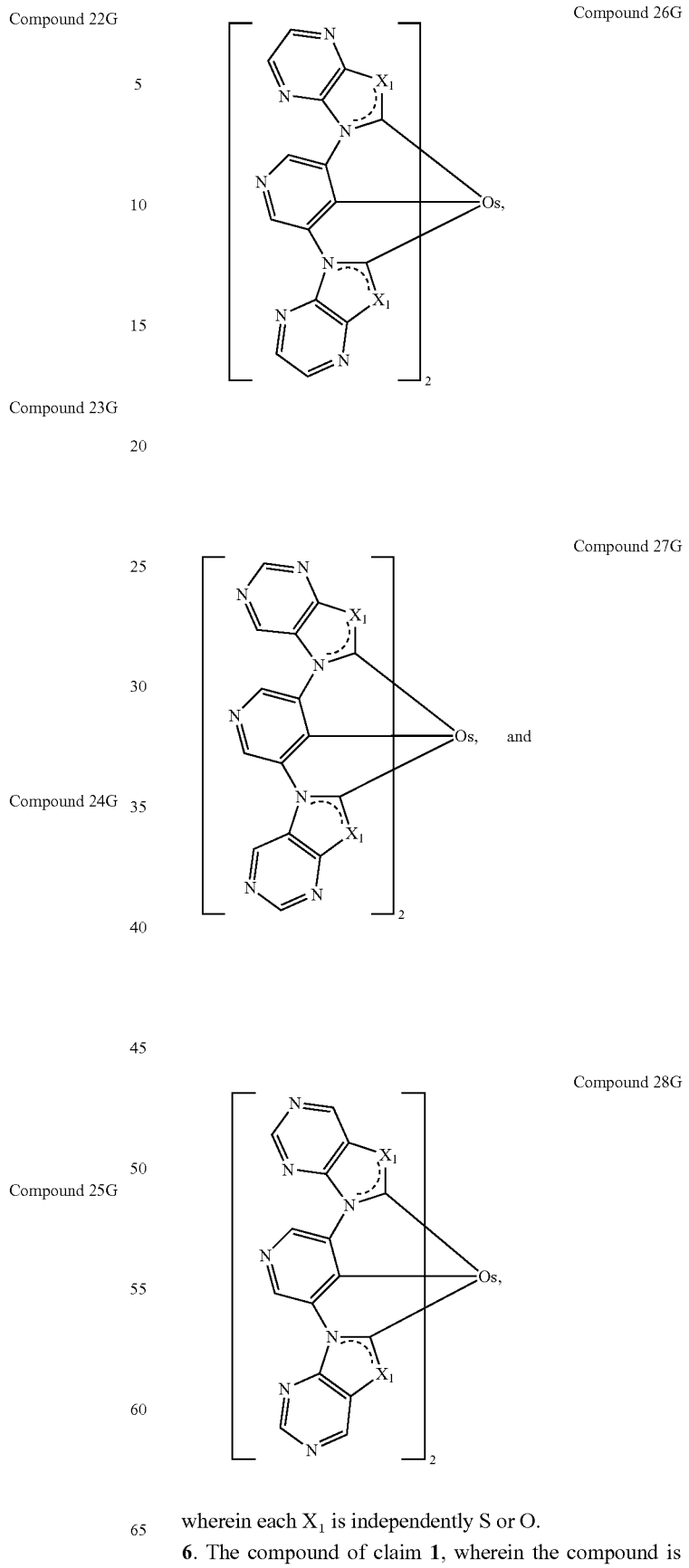
Compound 26G
Compound 27G
and
Compound 28G
wherein each $X_1$ is independently S or O.
6. The compound of claim 1, wherein the compound is selected from the group consisting of:

Compound 11
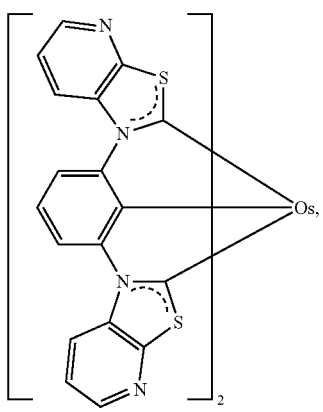
Compound 12
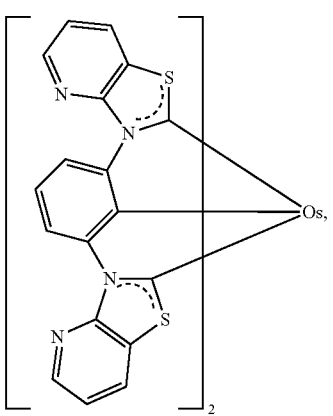
Compound 13
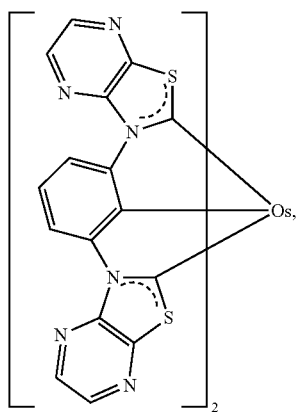
Compound 14
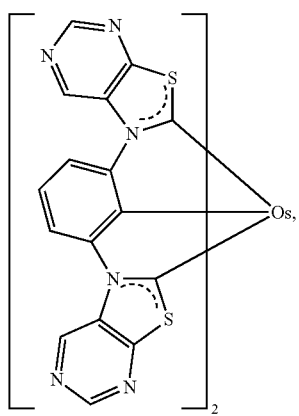
Compound 15
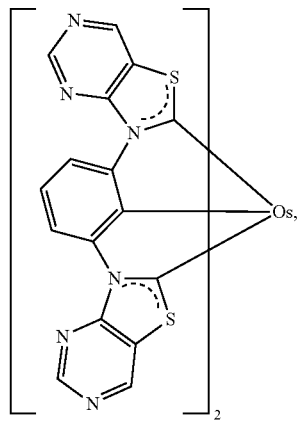
Compound 16
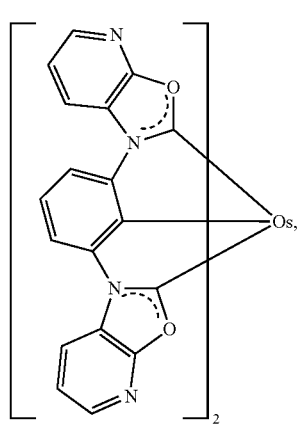
Compound 17
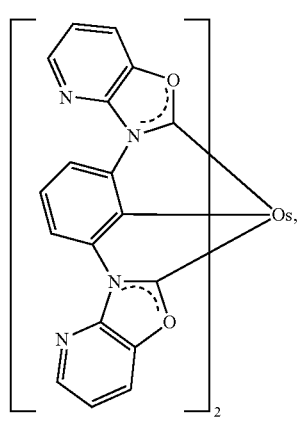
Compound 18
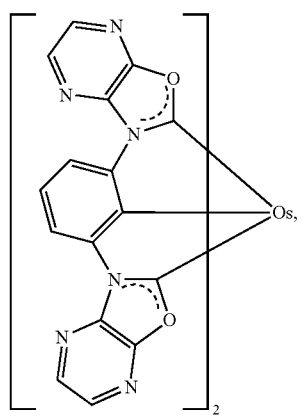

-continued

Compound 19

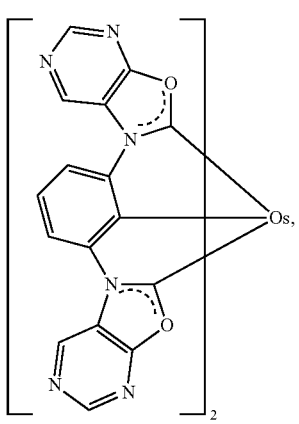

and

Compound 20

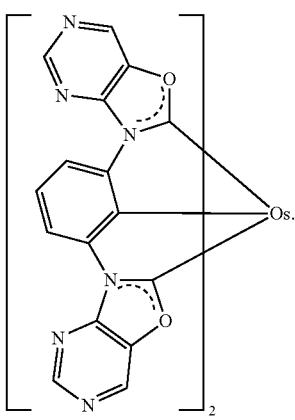

7. A first device comprising an organic light emitting device comprising:
an anode;
a cathode; and
an organic layer, disposed between the anode and the cathode, comprising a compound comprising a ligand L having the structure:

Formula I

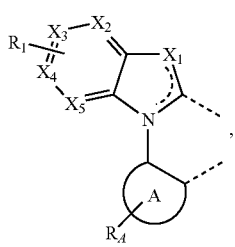

wherein $X_1$ is S or O;
wherein $X_2$, $X_3$, $X_4$, and $X_5$ are independently C or N;
wherein at least one of $X_2$, $X_3$, $X_4$, and $X_5$ is N;
wherein $R_1$ may represent mono, di, or tri substitutions;
wherein each $R_1$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein two adjacent substituents of $R_1$ are optionally joined to form a fused ring;
wherein $R_A$ may represent mono, di, tri, or tetra substitutions;
wherein each $R_A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein two adjacent substituents of $R_A$ are optionally joined to form a fused ring;
wherein A is a 6-membered carbocyclic or heterocyclic ring;
wherein the ligand L is coordinated to Os;
wherein the compound is homoleptic; and
wherein one $R_A$ is also coordinated to Os and ligand L is a tridentate ligand.

8. The first device of claim 7, wherein A is benzene.

9. The first device of claim 7, wherein the ligand L has the formula:

Formula II

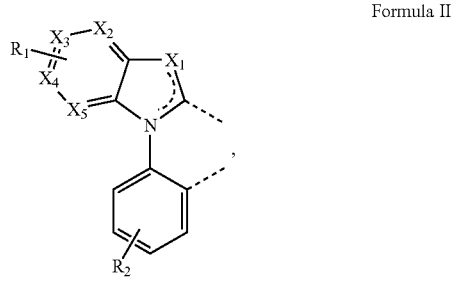

wherein at least one of $X_2$, $X_3$, $X_4$, and $X_5$ is N;
wherein $R_2$ has the same meaning as $R_A$ in Formula I.

10. The first device of claim 7, wherein the ligand L has the formula:

Formula II

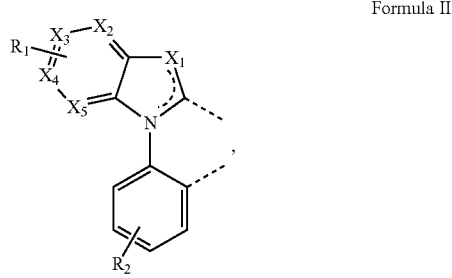

wherein at least two of $X_2$, $X_3$, $X_4$, and $X_5$ are N;
wherein $R_2$ has the same meaning as $R_A$ in Formula I.

11. The first device of claim 7, wherein the compound is selected from the group consisting of:

Compound 8G
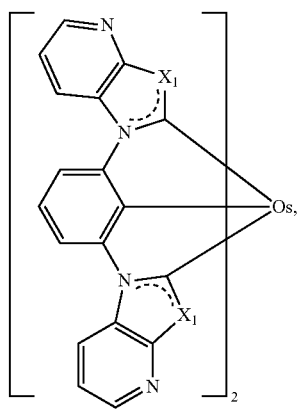
Compound 9G
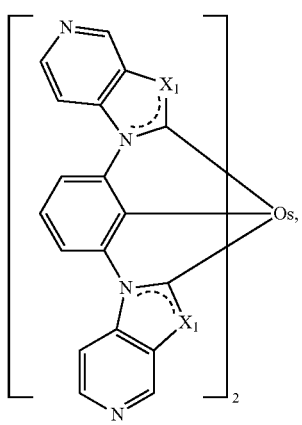
Compound 10G
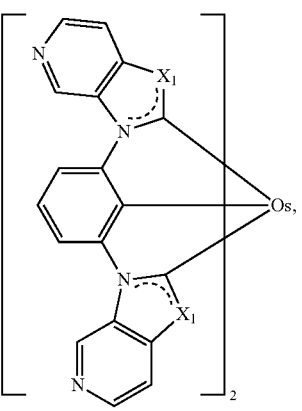
Compound 11G
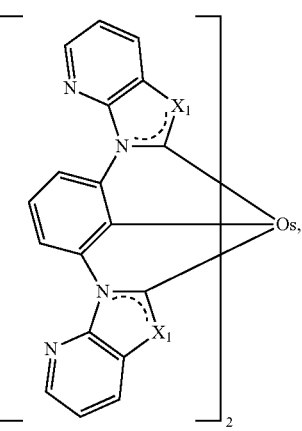
Compound 12G
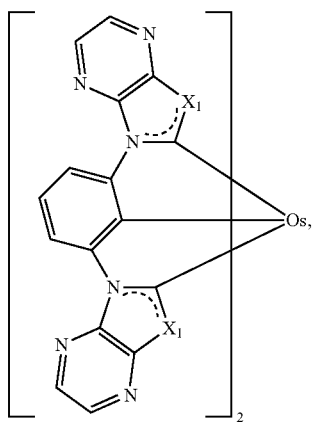
Compound 13G
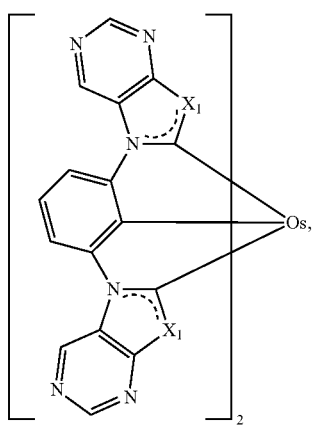
Compound 14G
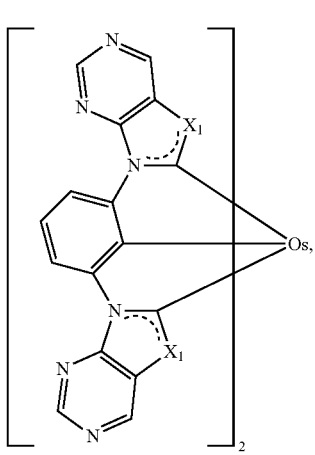

Compound 15G
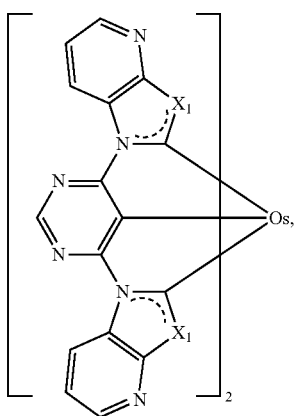
Compound 16G
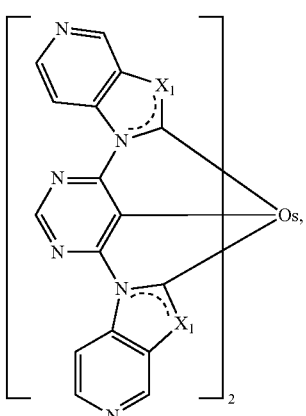
Compound 17G
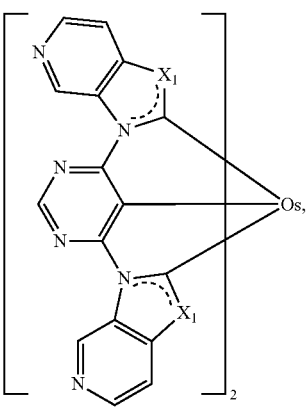
Compound 18G
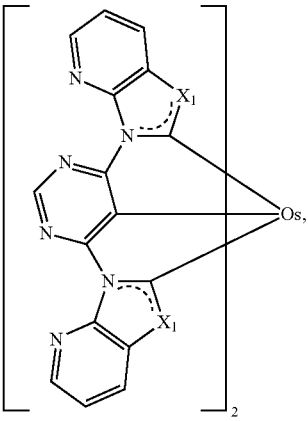
Compound 19G
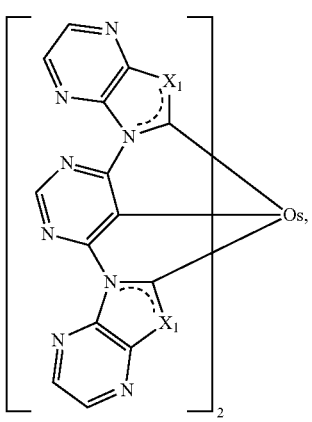
Compound 20G
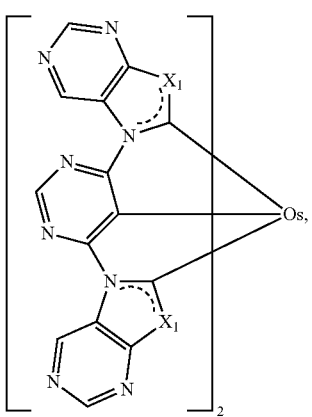
Compound 21G
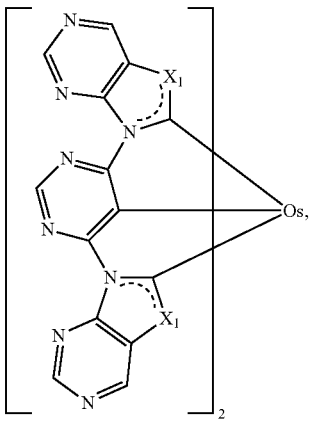

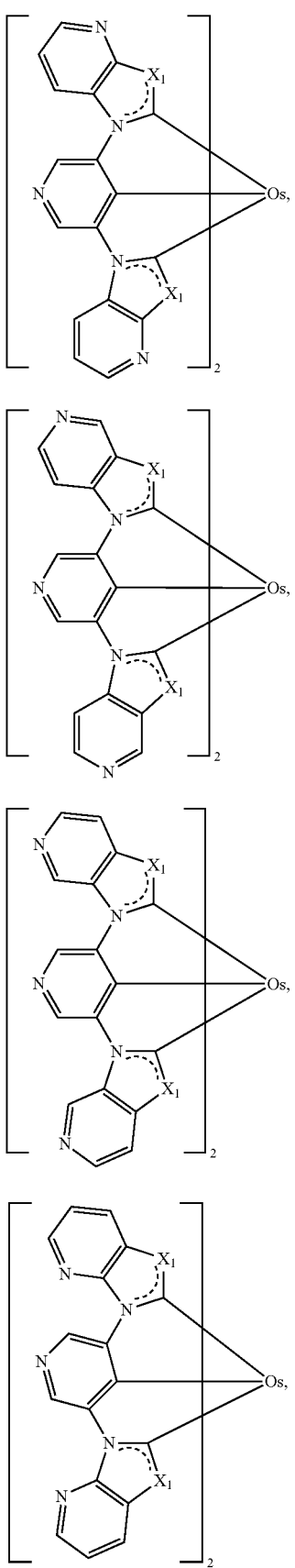
Compound 22G
Compound 23G
Compound 24G
Compound 25G
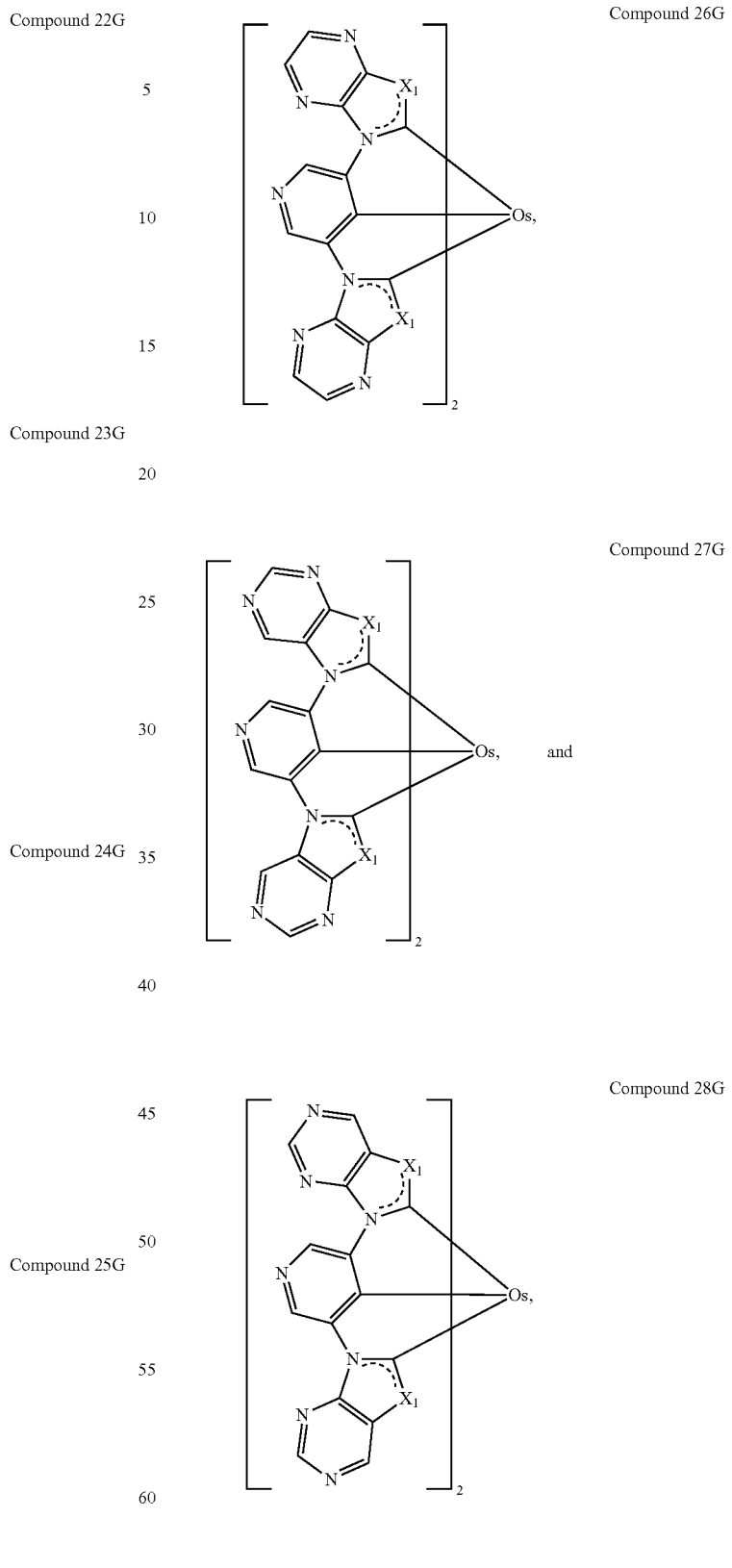
Compound 26G
Compound 27G and
Compound 28G
wherein each $X_1$ is independently S or O.
12. The first device of claim 7, wherein the compound is selected from the group consisting of:

Compound 11
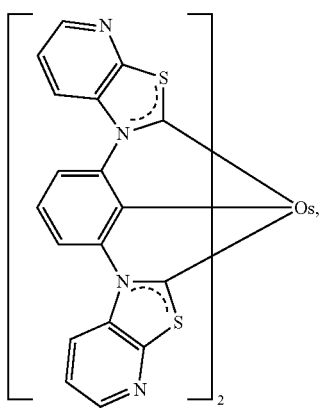
Compound 12
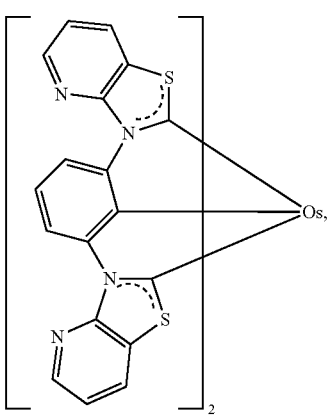
Compound 13
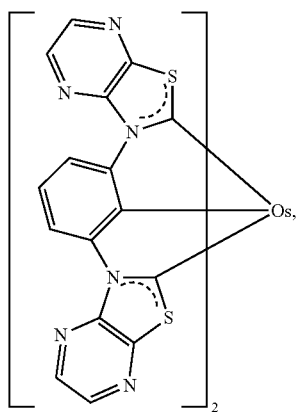
Compound 14
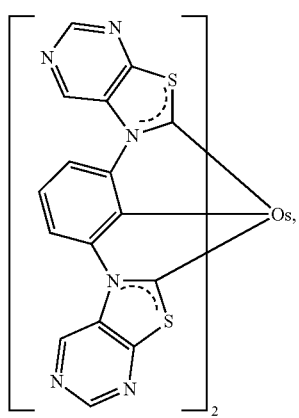
-continued
Compound 15
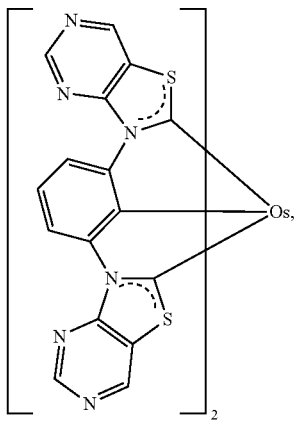
Compound 16
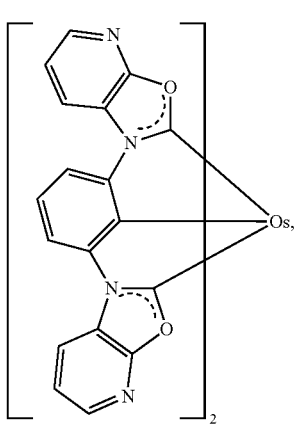
Compound 17
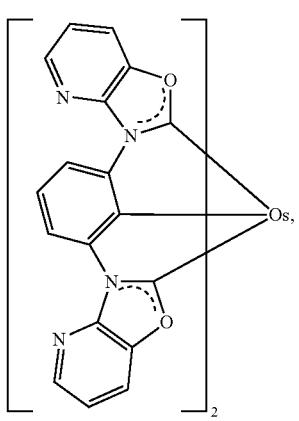
Compound 18
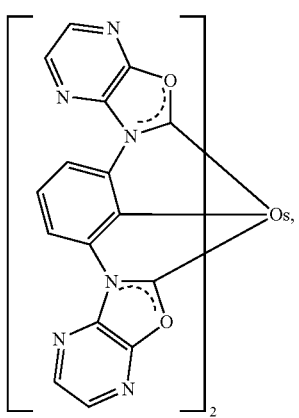

-continued

Compound 19

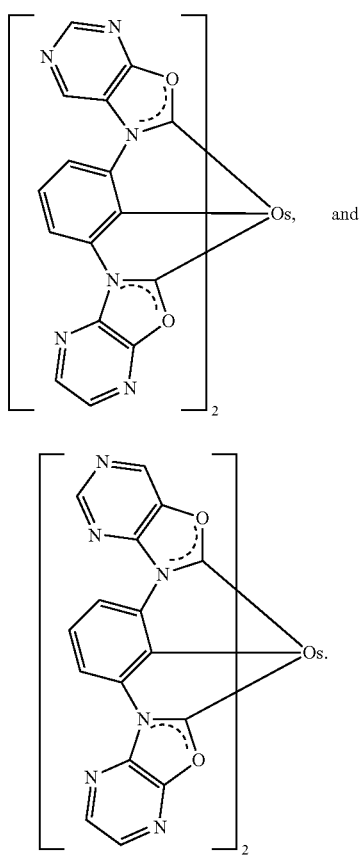

Compound 20

13. The first device of claim 7, wherein the organic layer is an emissive layer and the compound is an emissive dopant.

14. The first device of claim 13, wherein the organic layer further comprises a host.

15. The first device of claim 14, wherein the host is a compound that comprises at least one of the chemical groups selected from the group consisting of:

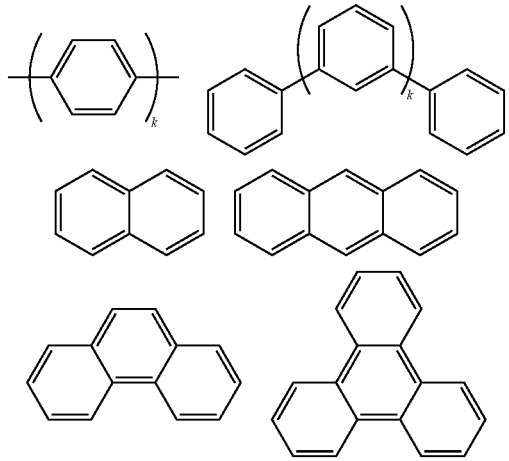

-continued

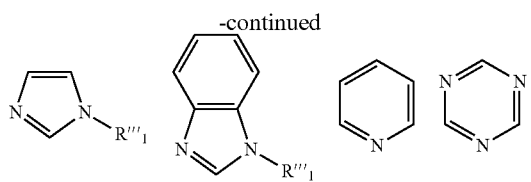

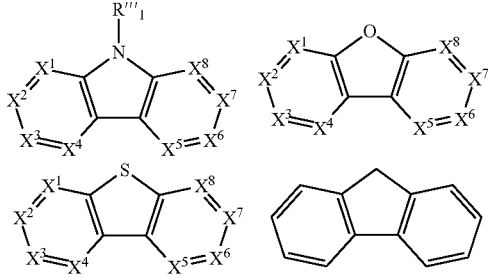

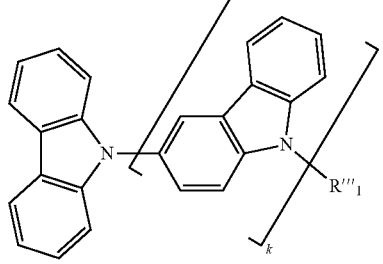

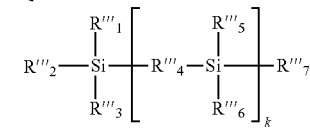

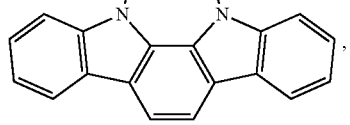

wherein each of $R'''_1$, $R'''_2$, $R'''_3$, $R'''_5$, $R'''_6$ and $R'''_7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein $R'''_4$ is selected from the group consisting of alkylene, cycloalkylene, heteroalkylene, arylalkylene, alkylene ether, arylene ether, amine, silylene, alkenylene, cycloalkenylene, heteroalkenylene, alkynylene, arylene, heteroarylene, acyl, carbonyl, ester, sulfinyl, sulfonyl, phosphino, and combinations thereof;

wherein two adjacent substituents are optionally joined to form a fused ring;

wherein $k^1$ is an integer from 1 to 20 and k is an integer from 0 to 20; and wherein each of $X^1$, $X^2$, $X^3$, $X^4$, $X^5$, $X^6$, $X^7$ and $X^8$ is independently selected from the group consisting of CH and N.

16. The first device of claim 14, wherein the host is a metal complex.

17. The first device of claim 16, wherein the metal complex is selected from the group consisting of:

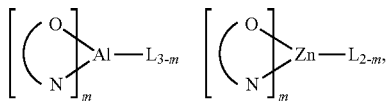

wherein (O—N) is a bidentate ligand having metal coordinated to atoms O and N;
wherein L is an ancillary ligand; and
wherein m is an integer value from 1 to the maximum number of ligands that may be attached to the metal.

18. The first device of claim 7, wherein the first device is a consumer product.

19. A process for making a carbene metal complex, comprising:
reacting a copper chloride carbene complex with an osmium precursor to yield the carbene metal complex comprising a ligand L having the structure:

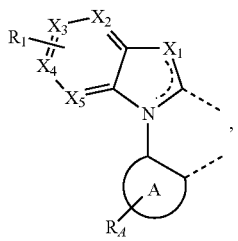

Formula I wherein $X_1$ is S or O;
wherein $X_2$, $X_3$, $X_4$, and $X_5$ are independently C or N;
wherein at least one of $X_2$, $X_3$, $X_4$, and $X_5$ is N;
wherein $R_1$ may represent mono, di, or tri substitutions;
wherein each $R_1$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein two adjacent substituents of $R_1$ are optionally joined to form a fused ring;
wherein $R_A$ may be mono, di, tri, or tetra substitutions;
wherein each $R_A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein two adjacent substituents of $R_A$ are optionally joined to form a fused ring;
wherein A is a 6-membered carbocyclic or heterocyclic ring;
wherein the ligand L is coordinated to Os;
wherein the compound is homoleptic; and
wherein one $R_A$ is also coordinated to Os and ligand L is a tridentate ligand.

20. The process of claim 19, further comprising reacting a carbene salt with copper-t-butoxide to yield a copper chloride carbene complex, prior to reacting the copper chloride carbene complex with the osmium precursor.

21. The process of claim 19, wherein the osmium precursor is $OsCl_2(DMSO)_4$.

22. The process of claim 19, wherein X is S.

23. The process of claim 19, wherein X is O.

24. The compound of claim 1, wherein $R_A$ represents a mono substitution of the A ring at a position ortho to the A ring carbon that coordinates to Os.

25. The first device of claim 7, wherein $R_A$ represents a mono substitution of the A ring at a position ortho to the A ring carbon that coordinates to Os.

* * * * *

UNITED STATES PATENT AND TRADEMARK OFFICE
CERTIFICATE OF CORRECTION

PATENT NO. : 9,005,772 B2  
APPLICATION NO. : 13/033287  
DATED : April 14, 2015  
INVENTOR(S) : Jui-Yi Tsai et al.

Page 1 of 3

It is certified that error appears in the above-identified patent and that said Letters Patent is hereby corrected as shown below:

In the Claims:

Claim 12, Column 141, Lines 1-18 – delete

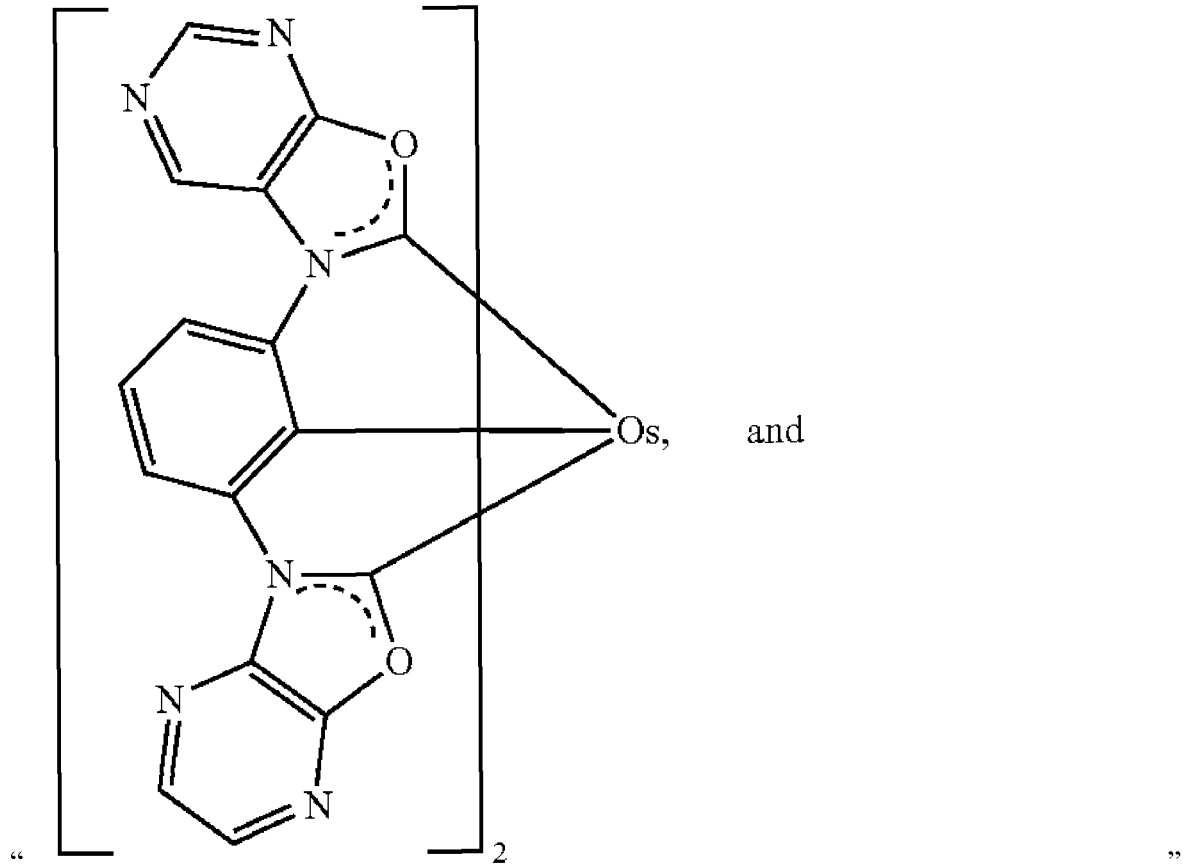

Signed and Sealed this
Twenty-seventh Day of October, 2015

Michelle K. Lee
*Director of the United States Patent and Trademark Office*

CERTIFICATE OF CORRECTION (continued)
U.S. Pat. No. 9,005,772 B2

Page 2 of 3

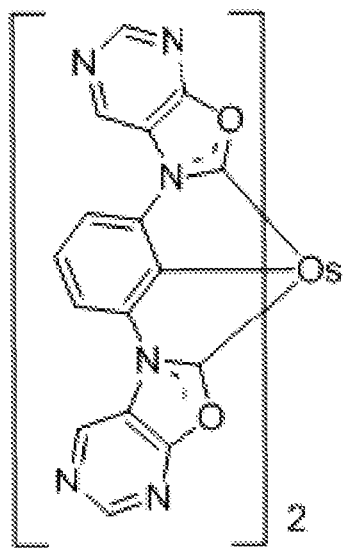

Compound 19 and insert --

Claim 12, Column 141, Lines 19-35 – delete

"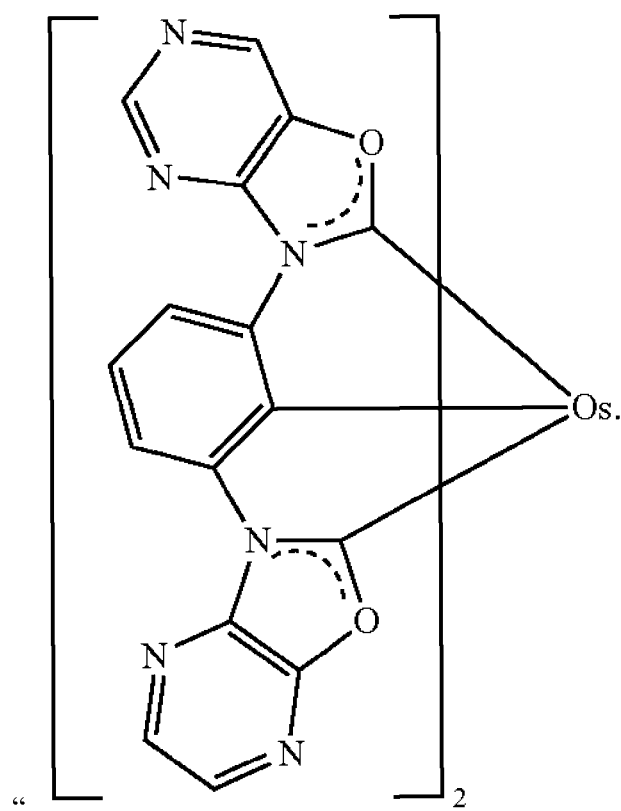"

Compound 20

CERTIFICATE OF CORRECTION (continued)
U.S. Pat. No. 9,005,772 B2

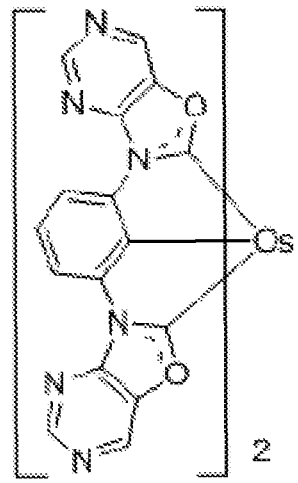

and insert -- Compound 20 --

Claim 15, Column 141, Lines 50-54 – delete

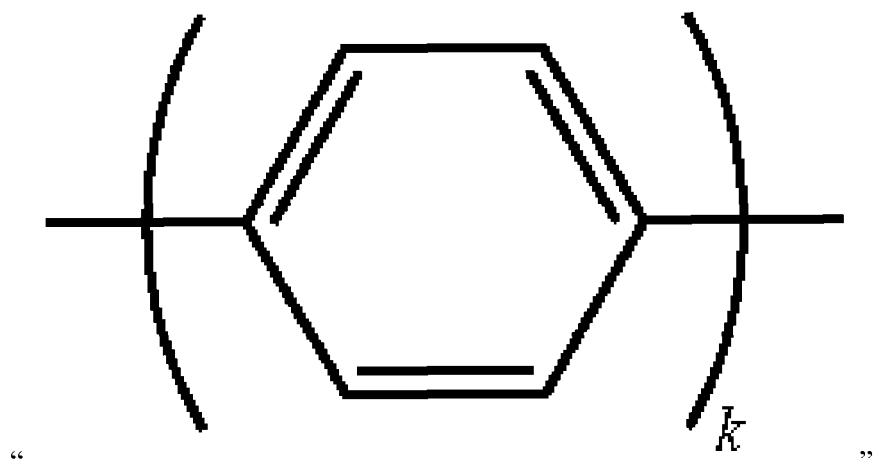

"

"

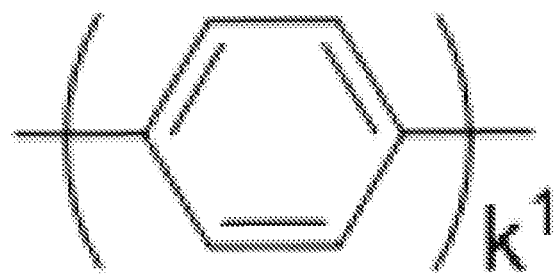

and insert -- --